United States Patent
Kono et al.

(10) Patent No.: US 8,524,505 B2
(45) Date of Patent: Sep. 3, 2013

(54) BLOOD ANALYZER AND BLOOD ANALYZING METHOD

(75) Inventors: Mari Kono, Kobe (JP); Yuri Takagi, Kobe (JP); Shoichiro Asada, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 13/381,052

(22) PCT Filed: Jun. 30, 2010

(86) PCT No.: PCT/JP2010/004323
§ 371 (c)(1),
(2), (4) Date: Dec. 27, 2011

(87) PCT Pub. No.: WO2011/001681
PCT Pub. Date: Jan. 6, 2011

(65) Prior Publication Data
US 2012/0115159 A1 May 10, 2012

(30) Foreign Application Priority Data
Jul. 3, 2009 (JP) ................................. 2009-159203

(51) Int. Cl.
*G01N 21/00* (2006.01)
*C12M 1/34* (2006.01)

(52) U.S. Cl.
USPC ....... 436/164; 422/73; 422/82.05; 422/82.08; 422/82.09; 436/546; 436/10; 436/64; 436/171; 436/172; 436/56; 435/6; 435/7.24; 435/372.2; 435/372.3; 435/287.1; 435/287.2

(58) Field of Classification Search
USPC .................. 435/6, 372.2, 372.3, 287.2, 7.24, 435/287.1; 436/546, 10, 64, 164, 171, 172, 436/800, 56; 422/73, 82.05, 82.08, 82.09
See application file for complete search history.

(56) References Cited

U.S. PATENT DOCUMENTS

| | | | |
|---|---|---|---|
| 4,284,412 A | 8/1981 | Hansen et al. | |
| 4,581,223 A * | 4/1986 | Kass | 435/34 |
| 6,004,816 A | 12/1999 | Mizukami et al. | |
| 7,354,727 B2 * | 4/2008 | Yoshida et al. | 435/7.24 |
| 2005/0042688 A1 * | 2/2005 | Hashemi | 435/7.2 |
| 2005/0069959 A1 | 3/2005 | Yoshida et al. | |
| 2007/0109530 A1 * | 5/2007 | Ueno et al. | 356/39 |
| 2007/0178597 A1 | 8/2007 | Tsuji et al. | |
| 2008/0131898 A1 * | 6/2008 | Tsuji et al. | 435/6 |
| 2010/0248247 A1 * | 9/2010 | Kataoka et al. | 435/6 |

FOREIGN PATENT DOCUMENTS

| | | |
|---|---|---|
| CN | 1967244 A | 5/2007 |
| JP | 57-161550 A | 10/1982 |
| JP | 10-319010 A | 12/1998 |

(Continued)

*Primary Examiner* — Gail R Gabel
(74) *Attorney, Agent, or Firm* — Sughrue Mion, PLLC

(57) ABSTRACT

The present invention provides a blood analyzer and a blood analyzing method capable of obtaining information regarding B lymphocytes and T lymphocytes without using a fluorescence-labeled antibody. The blood analyzer of the present invention includes a blood specimen supplying portion, a sample preparation portion that prepares a measurement sample without using a fluorescence-labeled antibody by mixing a blood specimen supplied from the blood specimen supplying portion, a hemolyzing agent, and a fluorescent dye that stains nucleic acid, a light source, a first detector that detects fluorescence, a second detector that detects scattered light, and information processing portion that classifies lymphocytes based on the intensity of fluorescence and scattered light, and based on the fluorescence intensity of the classified lymphocytes, obtains information regarding B-lymphocytes and T-lymphocytes.

13 Claims, 50 Drawing Sheets

(56) References Cited

FOREIGN PATENT DOCUMENTS

| JP | 2004-028615 A | 1/2004 |
| JP | 2005-106484 A | 4/2005 |
| JP | 2007-225595 A | 9/2007 |
| JP | 2008-134062 A | 6/2008 |

* cited by examiner

FIG. 12

BLOOD ANALYZER AND BLOOD ANALYZING METHOD

CROSS REFERENCE TO RELATED APPLICATIONS

This application is a National Stage of International Application No. PCT/JP2010/004323 filed Jun. 30, 2010, claiming priority based on Japanese Patent Application No. 2009-159203 filed Jul. 3, 2009, the contents of all of which are incorporated herein by reference in their entirety.

TECHNICAL FIELD

The present invention relates to a blood analyzer and a blood analyzing method for optically measuring a blood specimen and classifying hemocytes contained in the blood specimen into a plurality of types.

BACKGROUND ART

There are different types of leucocytes in the peripheral blood of a healthy person, i.e., lymphocyte, monocyte, neutrophil, eosinophil, and basophil. Furthermore, lymphocyte is roughly classified into three types referred to as subsets (T-lymphocyte, B-lymphocyte, NK-lymphocyte).

B-lymphocyte is a bone marrow-derived lymphocyte and has immunoglobulin on its surface. B-lymphocyte plays a very important role in the immune function of a human body, for example, it differentiates into a plasma cell and produces an antibody. T-lymphocyte is a thymus-derived lymphocyte and does not have an immunoglobulin on its surface. T-lymphocyte plays an important role in regulating the immune system, and it is known that a T-lymphocyte defect often causes immunodeficient, autoimmune, allergic, and proliferative immune disorders.

As described above, B-lymphocytes and T-lymphocytes are greatly involved in the immune system. Therefore, checking an increase or decrease in B-lymphocyte and T-lymphocyte allows a change in immune function to be known. B-lymphocytes and T-lymphocytes are present in a specific ratio, but it can change due to the presence of a disease. Therefore, measuring the ratio of B-lymphocytes to T-lymphocytes allows useful information regarding the presence of a disease to be obtained.

Examples of diseases that show increased B-lymphocytes include multiple myeloma, B-lymphocytic chronic lymphocytic leukemia, infectious mononucleosis, Burkitt's lymphoma, and the like. Examples of diseases that decrease B-lymphocytes include AIDS, advanced cancer, Hodgkin's lymphoma, alymphocytic hypoimmunoglobulinemia, agammaglobulinemia, reticular dysgenesis, measles, varicella, herpes, and the like.

Examples of diseases that show increased T-lymphocytes include ATL, Sezary syndrome, infectious mononucleosis, agammaglobulinemia, and the like. Examples of diseases that decrease T-lymphocytes include AIDS, advanced cancer, alymphocytic hypoimmunoglobulinemia, and the like.

As a leucocyte classification method that uses flow cytometry, Patent Document 1 discloses a method for classifying leucocytes into five types and counting the number thereof in which a blood sample is treated with a hemolyzing agent that contains a cationic surfactant and a nonionic surfactant and a fluorescent dye that stains nucleic acid. However, Patent Document 1 completely fails to describe measurement of B-lymphocytes and T-lymphocytes.

Lymphocyte classification/counting attained by performing flow cytometry on lymphocytes that are labeled with a fluorescence-labeled antibody is already known as a technique for classifying/counting lymphocytes (Patent Document 2).

CITATION LIST

Patent Documents

Patent Document 1: JP H10-319010A
Patent Document 2: JP S56-16872A

SUMMARY OF INVENTION

Problem to be Solved by the Invention

However, the technique disclosed in Patent Document 2 above is problematic in the following points: An expensive fluorescence-labeled antibody needs to be used in measurement, and thus the measurement cost is high; and operations are complex, and thus the measurement takes a long period of time.

An object of the present invention is to provide a blood analyzer and a blood analyzing method capable of obtaining information regarding B lymphocytes and T lymphocytes without using an expensive fluorescence-labeled antibody.

Means for Solving Problem

That is, the blood analyzer of one aspect of the present invention includes: a blood specimen supplying portion for supplying a blood specimen; a sample preparation portion for preparing a measurement sample without using a fluorescence-labeled antibody by mixing the blood specimen supplied from the blood specimen supplying portion, a hemolyzing agent, and a fluorescent dye that stains nucleic acid; a light source for irradiating light onto the measurement sample prepared by the sample preparation portion; a first detector for detecting fluorescence emitted from the measurement sample irradiated with light by the light source; a second detector for detecting scattered light emitted from the measurement sample irradiated with light by the light source; an information processing portion for obtaining an indicator representing a particle size distribution of fluorescence intensity of lymphocytes based on intensity of fluorescence detected by the first detector and intensity of scattered light detected by the second detector, and obtaining information regarding a ratio of a B-lymphocyte count to a T-lymphocyte count based on the obtained indicator representing the particle size distribution of fluorescence intensity of lymphocytes; and an output portion for outputting the information regarding the ratio of the B-lymphocyte count to the T-lymphocyte count obtained by the information processing portion.

In this aspect, the information processing portion may be configured to obtain, as the information regarding the ratio of the B-lymphocyte count to the T-lymphocyte count, a value representing a ratio of a B-lymphocyte count to a total B-lymphocyte and T-lymphocyte count; a value representing of a ratio of a T-lymphocyte count to a total B-lymphocyte and T-lymphocyte count; information indicating that a ratio of a B-lymphocyte count to a total B-lymphocyte and T-lymphocyte count is in a predetermined range; information indicating that a ratio of a T-lymphocyte count to a total B-lymphocyte and T-lymphocyte count is in a predetermined range; or information indicating the presence or absence of an abnormal ratio of a T-lymphocyte count to a B-lymphocyte count.

In the foregoing aspect, the information processing portion may be configured to obtain, as the indicator representing the particle size distribution of fluorescence intensity of lymphocytes, a measure of central tendency of fluorescence intensity of lymphocytes, and based on the obtained measure of central tendency, obtain the information regarding the ratio of the B-lymphocyte count to the T-lymphocyte count.

In the foregoing aspect, the information processing portion may be configured to obtain, as the indicator representing the particle size distribution of fluorescence intensity of lymphocytes, a dispersion of fluorescence intensity of lymphocytes, and based on the obtained dispersion, obtain the information regarding the ratio of the B-lymphocyte count to the T-lymphocyte count.

In the foregoing aspect, the information processing portion may be configured to obtain, as the indicator representing the particle size distribution of fluorescence intensity of lymphocytes, a value representing a bias in a distribution of fluorescence intensity of lymphocytes, and based on the value representing the bias in the distribution, obtain the information regarding the ratio of the B-lymphocyte count to the T-lymphocyte count.

In the foregoing aspect, the information processing portion may be configured to obtain, as the value representing the bias in the distribution, kurtosis or skewness of the distribution of fluorescence intensity of lymphocytes, and based on the obtained kurtosis or skewness, obtain the information regarding the ratio of the B-lymphocyte count to the T-lymphocyte count.

In the foregoing aspect, the information processing portion may be configured to compare the indicator representing the particle size distribution of fluorescence intensity of lymphocytes with a predetermined threshold value to determine whether the ratio of the B-lymphocyte count to the T-lymphocyte count is abnormal or not, and the output portion is configured to, in the case where the ratio of the B-lymphocyte count to the T-lymphocyte count is determined to be abnormal by the information processing portion, output information indicating that the ratio of the B-lymphocyte count to the T-lymphocyte count is abnormal as the information regarding the ratio of the B-lymphocyte count to the T-lymphocyte count.

In the foregoing aspect, the information processing portion is configured to obtain a value representing a ratio of a B-lymphocyte count to a total B-lymphocyte and T-lymphocyte count based on the indicator representing the particle size distribution of fluorescence intensity of lymphocytes, and compare the obtained value with a predetermined threshold value to determine whether the ratio of the B-lymphocyte count to the T-lymphocyte count is abnormal or not and the output portion is configured to, in the case where the ratio of the B-lymphocyte count to the T-lymphocyte count is determined to be abnormal by the information processing portion, output information indicating that the ratio of the B-lymphocyte count to the T-lymphocyte count is abnormal as the information regarding the ratio of the B-lymphocyte count to the T-lymphocyte count.

In the foregoing aspect, the information processing portion is configured to obtain a value representing a ratio of a T-lymphocyte count to a total B-lymphocyte and T-lymphocyte count based on the indicator representing the particle size distribution of fluorescence intensity of lymphocytes, and compare the obtained value with a predetermined threshold value to determine whether the ratio of the B-lymphocyte count to the T-lymphocyte count is abnormal or not, and the output portion is configured to, in the case where the B-lymphocyte count to T-lymphocyte count ratio is determined to be abnormal by the information processing portion, output information indicating that the ratio of the B-lymphocyte count to the T-lymphocyte count is abnormal as the information regarding the ratio of the B-lymphocyte count to the T-lymphocyte count.

In the foregoing aspect, the information processing portion may be configured to distinguish lymphocytes contained in the measurement sample from other leucocytes based on the intensity of fluorescence detected by the first detector and the intensity of scattered light detected by the second detector, and obtain the indicator representing the particle size distribution of fluorescence intensity of lymphocytes.

In the foregoing aspect, the information processing portion may be configured to distinguish lymphocytes contained in the measurement sample from other leucocytes to classify leucocytes, and the output portion is configured to output a result of leucocyte classification performed by the information processing portion.

In the foregoing aspect, the information processing portion may be configured to classify leucocytes contained in the measurement sample into at least four groups including lymphocytes.

In the foregoing aspect, the sample preparation portion may be configured to prepare the measurement sample by mixing a blood specimen supplied from the blood specimen supplying portion, a hemolyzing agent containing a cationic surfactant and a nonionic surfactant, and a fluorescent dye that stains nucleic acid.

The blood analyzing method of one aspect of the present invention includes the steps of preparing a measurement sample without using a fluorescence-labeled antibody by mixing a blood specimen, a hemolyzing agent, and a fluorescent dye that stains nucleic acid; irradiating light onto the prepared measurement sample; detecting both fluorescence and scattered light emitted from the measurement sample irradiated with light; obtaining an indicator representing a particle size distribution of fluorescence intensity of lymphocytes based on intensity of fluorescence and intensity of scattered light detected; obtaining information regarding a ratio of a B-lymphocyte count to a T-lymphocyte count based on the obtained indicator representing the particle size distribution of fluorescence intensity of lymphocytes; and outputting the obtained information regarding the ratio of the B-lymphocyte count to the T-lymphocyte count.

Effect of the Invention

According to the blood analyzer and the blood analyzing method of the present invention, it is possible to obtain information regarding B-lymphocytes and T-lymphocytes without using a fluorescence-labeled antibody.

BRIEF DESCRIPTION OF DRAWINGS

FIG. 12 is a picture showing a screen displaying results of analyzing a blood specimen A having an abnormal ratio of a B-lymphocyte count to a T-lymphocyte count in Embodiment 1.

DESCRIPTION OF EMBODIMENTS

Preferred embodiments of the present invention will now be described below with reference to the drawings.

Embodiment 1

This embodiment is directed to a blood analyzer that prepares a measurement sample by mixing a blood specimen, a hemolyzing agent, and a fluorescent dye that stains nucleic acid, measures the measurement sample with an optical flow cytometer, and obtains information regarding B-lymphocytes and T-lymphocytes present in the blood specimen.

[Configuration of Blood Analyzer]

Figure 1:
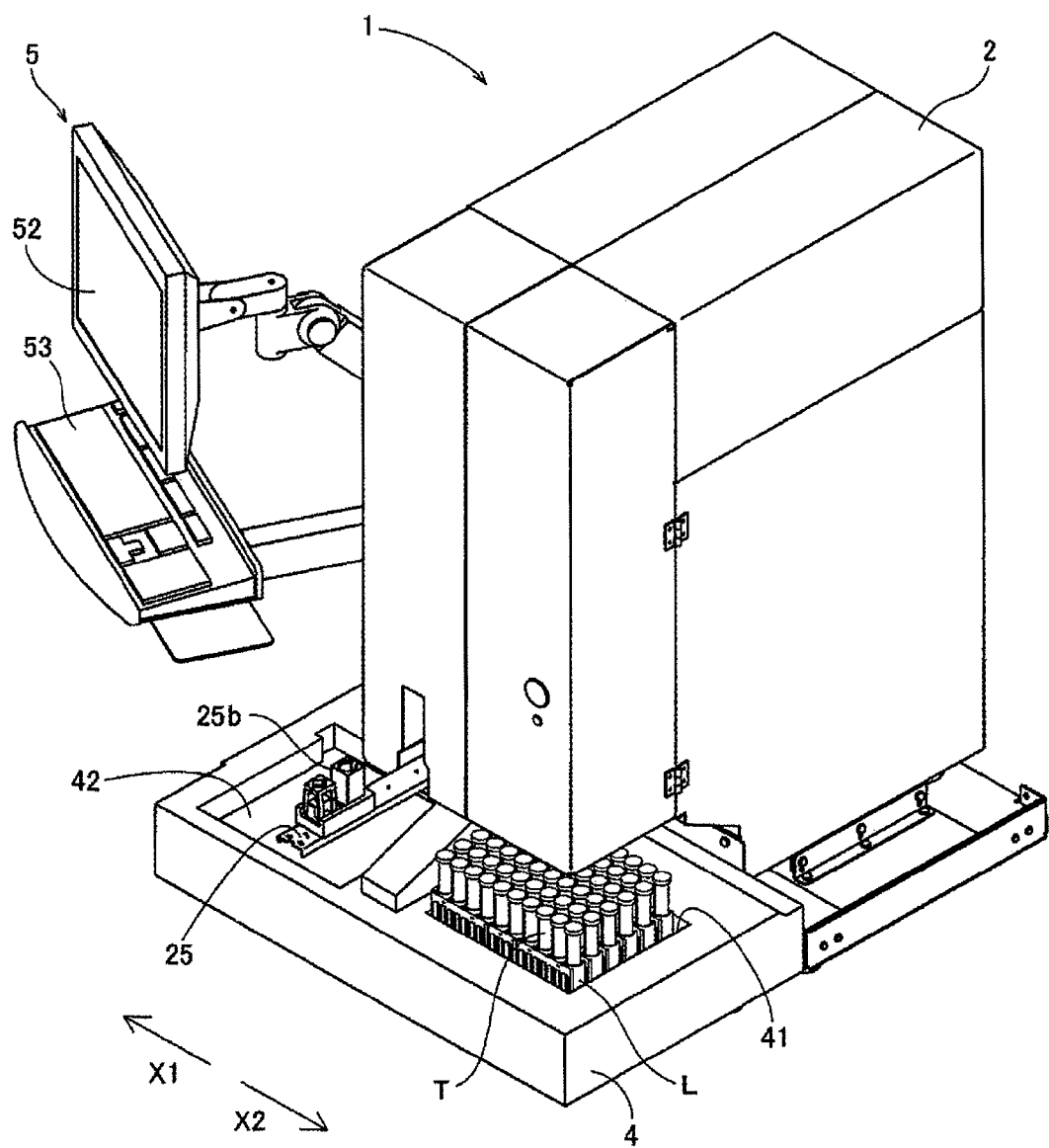
FIG. 1 is a perspective view showing the appearance of a blood analyzer according to Embodiment 1.

FIG. 1 is a perspective view showing the appearance of a blood analyzer of this embodiment. A blood analyzer 1 of this embodiment is a multiple-item hemocyte analysis apparatus for detecting hemocytes contained in a blood specimen, such as leukocytes, erythrocytes, and platelets, and counting each type of hemocytes. As shown in FIG. 1, the blood analyzer 1 includes a measurement unit 2, a specimen carrying unit 4 disposed on the front side of the measurement unit 2, and an information processing unit 5 capable of controlling the measurement unit 2 and the specimen carrying unit 4.

Figure 2:
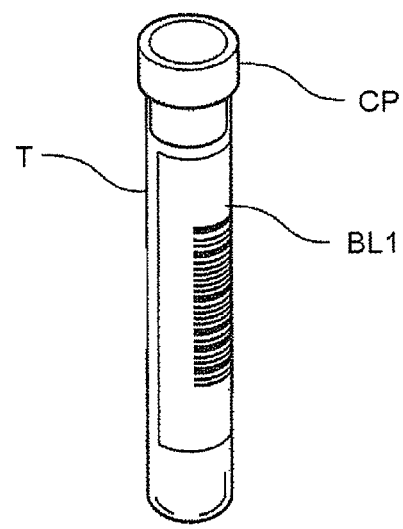
FIG. 2 is a perspective view showing the appearance of a specimen container.
Figure 3:
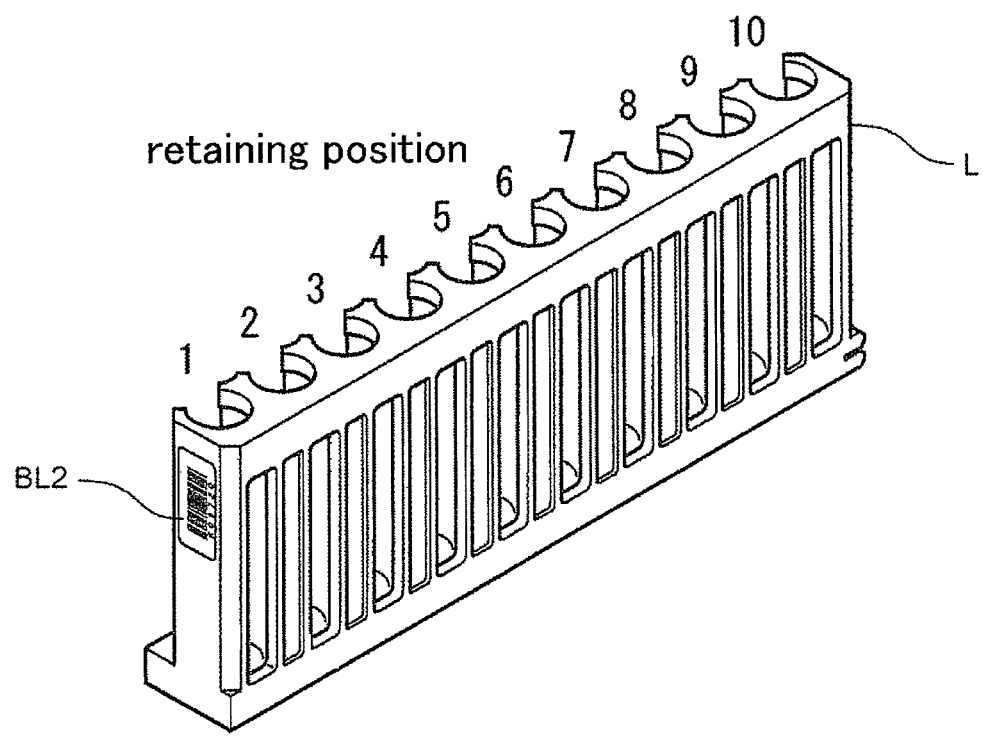
FIG. 3 is a perspective view showing the appearance of a sample rack.

FIG. 2 is a perspective view showing the appearance of a specimen container for accommodating a specimen. FIG. 3 is a perspective view showing the appearance of a sample rack for retaining a plurality of specimen containers. As shown in FIG. 2, a specimen container T is tubular, and its top is open. A blood specimen collected from a patient is accommodated therein, and the opening at the top is sealed by a cap CP. The specimen container T is composed of translucent glass or synthetic resin so that the blood specimen therein is visible. A bar code label BL1 is applied to the side of the specimen container T. A bar code that shows a specimen ID is printed on the bar code label BL1. A sample rack L is capable of retaining 10 specimen containers T in line. In the sample rack L, each specimen container T is retained upright (standing state). A bar code label BL2 is applied to the side of the sample rack L. A bar code that shows a rack ID is printed on the bar code label BL2.

<Configuration of Measurement Unit>

Figure 4:
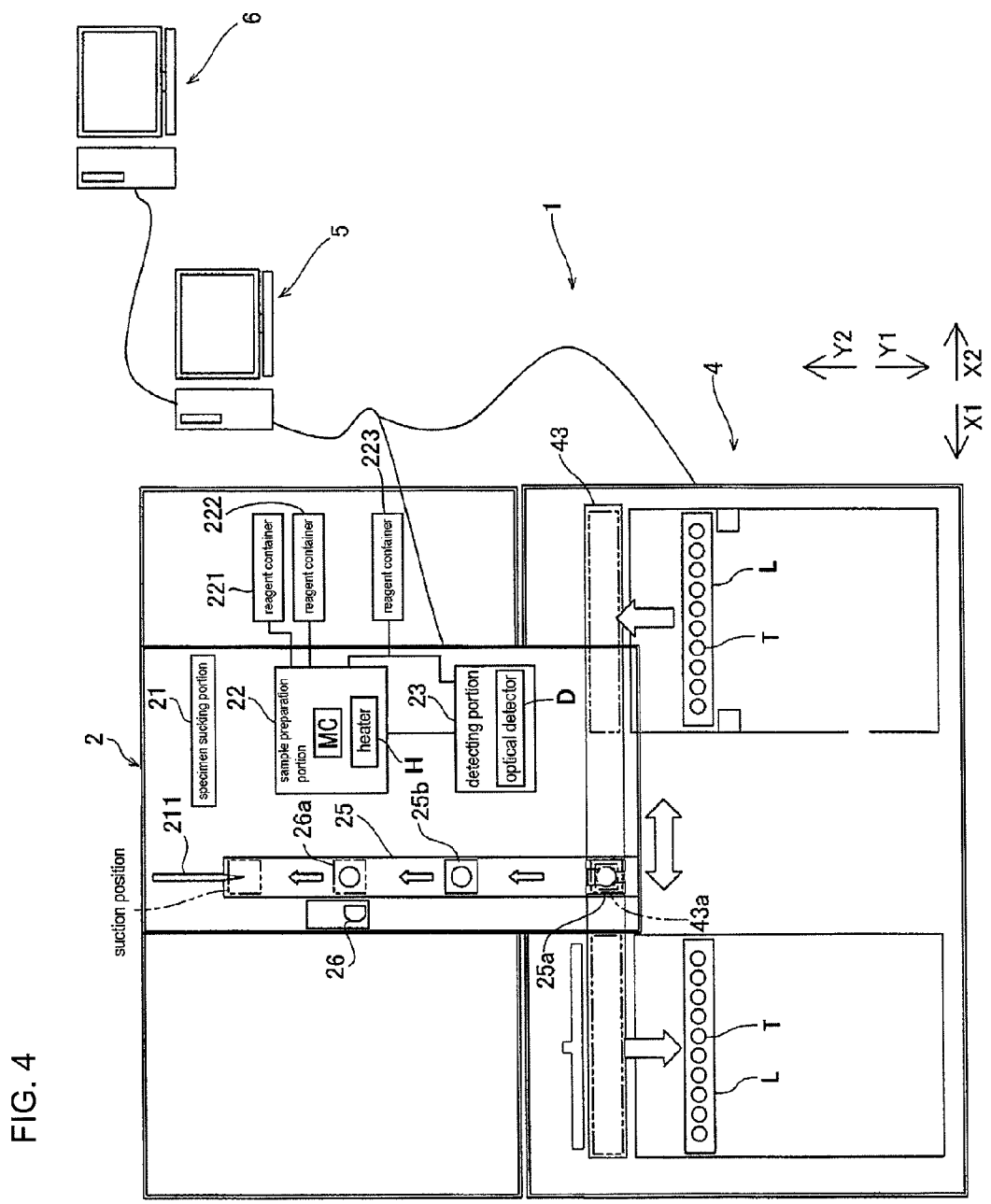
FIG. 4 is a block diagram showing the configuration of a measurement unit according to Embodiment 1.

Next, the configuration of the measurement unit will now be described. FIG. 4 is a block diagram showing the configuration of the measurement unit. As shown in FIG. 4, the measurement unit 2 includes a specimen suction portion 21 that sucks blood as a specimen from the specimen container (blood collecting tube) T, a sample preparation portion 22 that prepares a measurement sample used for measurement from the blood sucked by the specimen suction portion 21, and a detecting portion 23 that detects hemocytes in the measurement sample prepared by the sample preparation portion 22. The measurement unit 2 further includes an inlet (see FIG. 1) for taking, into the measurement unit 2, the specimen container T accomodated in the sample rack L carried by a rack carrying portion 43 of the specimen carrying unit 4, and a specimen container carrying portion 25 that takes the specimen container T from the sample rack L into the measurement unit 2 and carries the specimen container T to a suction position where blood is sucked by the specimen suction portion 21.

As shown in FIG. 4, the specimen suction portion 21 includes a suction tube 211. The specimen suction portion 21 also includes a syringe pump (not shown). Furthermore, the suction tube 211 is vertically movable, and is configured such that once the suction tube 211 is moved downward, the suction tube penetrates the cap CP of the specimen container T that has been carried to the suction position and sucks the blood therein.

The sample preparation portion 22 includes mixing chambers MC. The suction tube 211 sucks a predetermined amount of a whole blood specimen from the specimen container T using the syringe pump (not shown). The specimen thus sucked is transferred to the position of the mixing chambers MC, and a predetermined amount of the whole blood specimen is dispensed to each chamber MC using the syringe pump. The sample preparation portion 22 also includes a heater H for heating the mixing chambers MC.

The sample preparation portion 22 is connected via a tube to a reagent container 221 for accommodating a first reagent, a reagent container 222 for accommodating a second reagent, a reagent container 223 for accommodating a third reagent that is a sheath fluid (diluting fluid). The sample preparation portion 22 is also connected to a compressor (not shown), and the respective reagents can be drawn from the corresponding reagent containers 221, 222, and 223 with the pressure generated by the compressor.

The first reagent is a reagent containing a hemolyzing agent for hemolyzing erythrocytes. A known hemolyzing agent used in leucocyte measurement can be used as such a hemolyzing agent contained in the first reagent. More specifically, it is preferable to use a hemolyzing agent that contains a cationic surfactant and a nonionic surfactant.

Here, a quaternary ammonium salt surfactant or a pyridinium salt surfactant is preferable as a cationic surfactant. More specifically, surfactants having a total of 9 to 30 carbon atoms represented by:

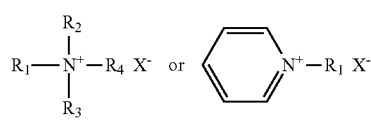

Formula 1 wherein $R_1$ is an alkyl or alkenyl group having 6 to 18 carbon atoms; $R_2$ and $R_3$ each are an alkyl or alkenyl group having 1 to 4 carbon atoms; $R_4$ is an alkyl or alkenyl group having 1 to 4 carbon atoms or a benzyl group; and X is a halogen atom.

$R_1$ is preferably an alkyl or alkenyl group having 6, 8, 10, 12, or 14 carbon atoms, with a linear alkyl group being particularly preferable. More specific examples of $R_1$ include an octyl group, a decyl group, and a dodecyl group. $R_2$ and $R_3$ each are particularly preferably a methyl group, an ethyl group, or a propyl group. $R_4$ is preferably a methyl group, an ethyl group, or a propyl group.

The nonionic surfactant is preferably a polyoxyethylene-based nonionic surfactant represented by structural formula (II) below:

Formula 2

$R_1\text{-}R_2\text{—}(CH_2CH_2O)n\text{-}H$ (II)

wherein $R_1$ is an alkyl, alkenyl, or alkynyl group having 8 to 25 carbon atoms; $R_2$ is O, Formula 3

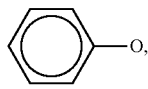

or COO: and n represents an integer of 10 to 50.

The hemolyzing agent may contain components other than the cationic surfactants and the nonionic surfactants mentioned above. Examples of such other components that may be contained in the hemolyzing agent include organic acids, buffers, and the like.

Here, as such organic acids, organic acids that have at least one aromatic ring in the molecule or salts thereof are preferable. More specific examples include benzoic acid, phthalic acid, hippuric acid, salicylic acid, p-aminobenzenesulfonic acid, benzenesulfonic acid, salts thereof, and the like.

Examples of buffers include citric acid salts, HEPES, phosphoric acid salts, and the like. Preferable buffers maintain the pH of the hemolyzing agent at 4.5 to 11.0 and preferably 5.0 to 10.0.

An example of such a preferable first reagent may be Stromatolyser 4DL, a commercially available hemolyzing reagent for leukocyte measurement manufactured by Sysmex Corporation.

The second reagent is a reagent for fluorescently staining nucleated cells in a blood sample. A fluorescent dye capable of staining nucleic acid is contained in the second reagent. Such a dye barely stains erythrocytes, which do not have nucleic acid, but stains nucleated hemocytes such as leukocytes having nucleic acid and nucleated erythrocytes. The fluorescent dye capable of staining nucleic acid can be suitably selected according to the light irradiated from a light source.

Specific examples of fluorescent dyes capable of staining nucleic acid include propidium iodide, ethidium bromide, ethidium-acridine heterodimer, ethidium diazide, ethidium homodimer-1, ethidium homodimer-2, ethidium monoazide, trimethylenebis[[3-[[4-[[(3-methylbenzothiazol-3-ium)-2-yl]methylene]-1,4-dihydroquinoline]-1-yl]propyl]dimethylaminium]tetraiodide (TOTO-1), 4-[(3-methylbenzothiazol-2(3H)-ylidene)methyl]-1-[3-(trimethylaminio)propyl]quinolinium diiodide (TO-PRO-1), N,N,N',N'-tetramethyl-N,N'-bis[3-[4-[3-[(3-methylbenzothiazol-3-ium)-2-yl]-2-propenylidene]-1,4-dihydroquinolin-1-yl]propyl]-1,3-propandiaminium tetraiodide (TOTO-3), 2-[3-[[1-[3-(trimethylaminio)propyl]-1,4-dihydroquinolin]-4-ylidene]-1-propenyl]-3-methylbenzothiazol-3-ium diiodide (TO-PRO-3), and fluorescent dyes represented by structural formula (I) below. Among these examples, the fluorescent dyes represented by structural formula (I) below are preferable.

Formula 4

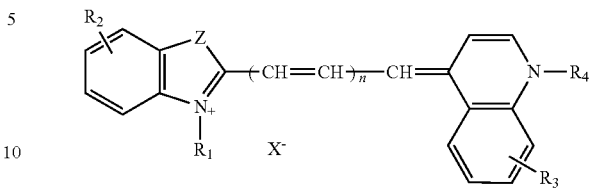

wherein, $R_1$ and $R_4$ each represent a hydrogen atom, an alkyl group, or a benzyl group optionally having a substituent; $R_2$ and $R_3$ each are a hydrogen atom, an alkyl group, an alkenyl group, an alkynyl group, or an alkoxy group; Z is sulfur, oxygen, or carbon having a methyl group; n is 0, 1, 2, or 3; and $X^-$ is an anion.

Here, it is preferable that when one of $R_1$ and $R_4$ in structural formula (I) is an alkyl group having 6 to 18 carbon atoms, the other is a hydrogen atom or an alkyl group having fewer than 6 carbon atoms. The alkyl group having 6 to 18 atoms is preferably an alkyl group having 6, 8, or 10 carbon atoms. Examples of substituents of the benzyl group represented by $R_1$ and $R_4$ include alkyl groups having 1 to 20 carbon atoms, alkenyl groups having 2 to 20 carbon atoms, and alkynyl groups having 2 to 20 carbon atoms. Examples of alkyl groups represented by $R_2$ and $R_3$ include alkyl groups having 1 to 20 carbon atoms, with a methyl group or an ethyl group being particularly preferable. Examples of alkenyl groups represented by $R_2$ and $R_3$ include alkenyl groups having 2 to 20 carbon atoms. Examples of alkynyl groups represented by $R_2$ and $R_3$ include alkynyl groups having 2 to 20 carbon atoms. Examples of alkoxy groups represented by $R_2$ and $R_3$ include alkoxy groups having 1 to 20 carbon atoms, with a methoxy group or an ethoxy group being particularly preferable. Examples of anions represented by $X^-$ include $F^-$, $Cl^-$, $Br^-$, $I^-$, $CF_3SO_3^-$, $BF_4^-$, and the like.

The concentration of fluorescent dye capable of staining nucleic acid in the second reagent can be suitably determined according to the kind of fluorescent dye. For example, the concentration of fluorescent dye represented by structural formula (I) is preferably 0.2 to 0.6 pg/µL and particularly preferably 0.3 to 0.5 pg/µL. The second reagent may contain one or two or more fluorescent dyes capable of staining nucleic acid.

An example of such a preferable second reagent may be Stromatolyser 4DS, a commercially available staining reagent for leukocyte measurement manufactured by Sysmex Corporation.

The third reagent is a sheath fluid supplied to a sheath flow cell, which will be described below. The sheath fluid is also used as a diluting fluid. An example of the sheath fluid may be Cellpack (II) manufactured by Sysmex Corporation.

The detecting portion 23 includes an optical detecton portion D capable of performing WBC measurement (leucocyte counting) and DIFF measurement (leucocyte classification). The optical detector D is configured to be able to detect WBCs (mature leucocytes), NRBCs (nucleated erythrocytes), and lymphoblasts (L-Blasts) by flow cytometry that uses a semiconductor laser. Use of the detecting portion 23 enables leukocytes to be classified into four types: LYMPH (lymphocyte), EO (eosinophil), NEUT+BASO (neutrophil+basophil), and MONO (monocyte); or five types: NEUT (neutrophil), LYMPH (lymphocyte), EO (eosinophil), BASO (basophil), and MONO (monocyte). When measuring B-lymphocytes and T-lymphocytes, a measurement sample in which a blood specimen, a first reagent, and a second reagent are mixed (a B•T-lymphocyte measurement sample) is supplied to the optical detector D. In the case where Stromatolyser 4DL is used as a first reagent and Stromatolyser 4DS is used as a second reagent, DIFF measurement and measurement of B-lymphocytes and T-lymphocytes can be performed with the same sample.

Figure 5:
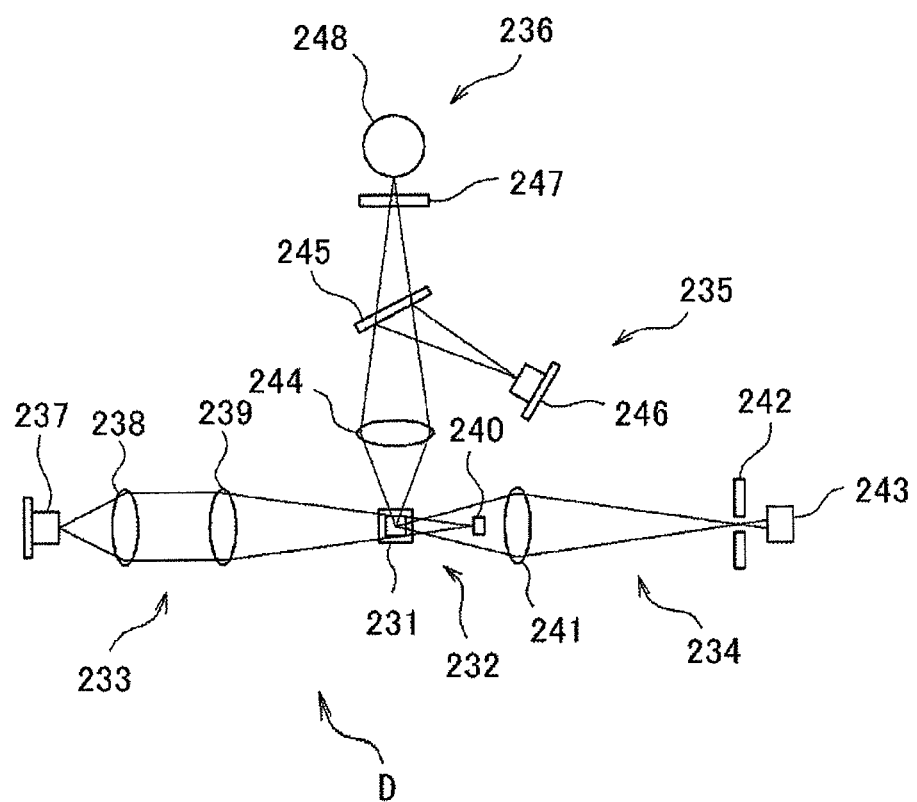
FIG. 5 is a schematic diagram showing a configuration outline of an optical detector.

FIG. 5 shows a configuration outline of the optical detector D. The optical detector D feeds a measurement sample and a sheath fluid to the flow cell 231 to generate a fluid current in the flow cell 231, and measures hemocytes contained in the fluid current flowing through the flow cell 231 by irradiating semiconductor laser light onto the hemocytes. The optical detector D includes a sheath flow system 232, a beam spot formation system 233, a forward scattered light receiving system 234, a side scattered light receiving system 235, and a fluorescence light receiving system 236.

The sheath flow system 232 is configured to cause a measurement sample to flow inside the flow cell 231 while being enclosed in the sheath fluid in the flow cell 231. The beam spot formation system 233 is configured to allow light irradiated from a semiconductor laser 237 to be irradiated onto the flow cell 231 through a collimator lens 238 and a condenser lens 239. Furthermore, the beam spot formation system 233 includes a beam stopper 240.

The forward scattered light receiving system 234 is configured to focus forward scattered light with a forward focusing lens 241, and receive the light that has passed through a pinhole 242 with a photodiode (forward scattered light receiving portion) 243.

The side scattered light receiving system 235 is configured to focus side scattered light with a side focusing lens 244, reflect a portion of the light at a dichroic mirror 245, and receive the reflected light with a photodiode (side scattered light receiving portion) 246.

Light scattering is a phenomenon that occurs when light changes the direction of its travel due the presence of particles such as hemocytes in the direction of travel as impediments. Information regarding the size and the material of the particles can be obtained by detecting such scattered light. In particular, information regarding the size of the particles (hemocytes) can be obtained from forward scattered light. Meanwhile, information regarding the interior of the particles can be obtained from side scattered light. When laser light is irradiated onto hemocyte particles, the intensity of side scattered light is dependent on the complexity of the cell interior (the shape, size, density, and the granular amount of the nucleus). Therefore, the intensity of scattered light can be used for leukocyte classification and like purposes.

The fluorescence light receiving system 236 is configured to allow the light that has transmitted through the dichroic mirror 245 to further transmit through a spectral filter 247, and receive the transmitted light with an avalanche photodiode (fluorescence light receiving portion) 248.

When light is irradiated onto a hemocyte that has been stained by a fluorescent substance, the hemocyte emits light having a wavelength longer than the wavelength of the irradiated light. The intensity of fluorescence is increased if the hemocyte has been stained well, and information regarding the staining degree of the hemocyte can be obtained by measuring the fluorescence intensity. Accordingly, the difference in (side) fluorescence intensity can be used for measuring B-lymphocytes and T-lymphocytes, classifying leukocytes, and the like.

Referring back to FIG. 4, the configuration of the specimen container carrying portion 25 will now be described next. The specimen container carrying portion 25 includes a hand portion 25a capable of gripping the specimen container T. The hand portion 25a includes a pair of gripping members arranged so as to face each other, and can move the gripping members toward and away from each other. The specimen container T can be gripped by the gripping members by moving the gripping members toward each other with the specimen container T interposed therebetween. Further, the specimen container carrying portion 25 can move the hand portion 25a in the up-down directions and the front-back directions (Y directions), and also can oscillate the hand portion 25a. This allows the specimen container T housed in the sample rack L and located at the specimen supply position 43a to be gripped by the hand portion 25a. In this state, the hand portion 25a is moved upward to pull out the specimen container T from the sample rack L. Then, the specimen in the specimen container T can be agitated by oscillating the hand portion 25a.

The specimen container carrying portion 25 also includes a specimen container setting portion 25b having a hole into which the specimen container T can be inserted. After completion of agitation, the specimen container T gripped by the above-described hand portion 25a is moved such that the gripped specimen container T is inserted into the hole of the specimen container setting portion 25b. Then, the gripping members are moved away from each other, thereby releasing the specimen container T from the hand portion 25a and setting the specimen container T in the specimen container setting portion 25b. The specimen container setting portion 25b can be moved horizontally in Y1 and Y2 directions in FIG. 4 by the power of a stepping motor (not shown).

A bar code reading portion 26 is provided inside the measurement unit 2. The specimen container setting portion 25b can be moved to a bar code reading position 26a in the vicinity of the bar code reading portion 26 and to the suction position 21a where the specimen is sucked by the specimen suction portion 21. When the specimen container setting portion 25b is moved to the bar code reading position 26a, the set specimen container T is horizontally rotated by a rotating mechanism (not shown), and the bar code of the specimen is read by the bar code reading portion 26. Accordingly, even when the bar code label BL1 of the specimen container T faces the side opposite the bar code reading portion 26, the bar code label BL1 can face the bar code reading portion 26 by rotating the specimen container T, thus enabling the bar-code reading portion 26 to read the specimen barcode. When the specimen container setting portion 25b is moved to the suction position, the specimen is sucked by the specimen suction portion 21 from the specimen container T that has been set.

<Configuration of Information Processing Unit>

Figure 6:
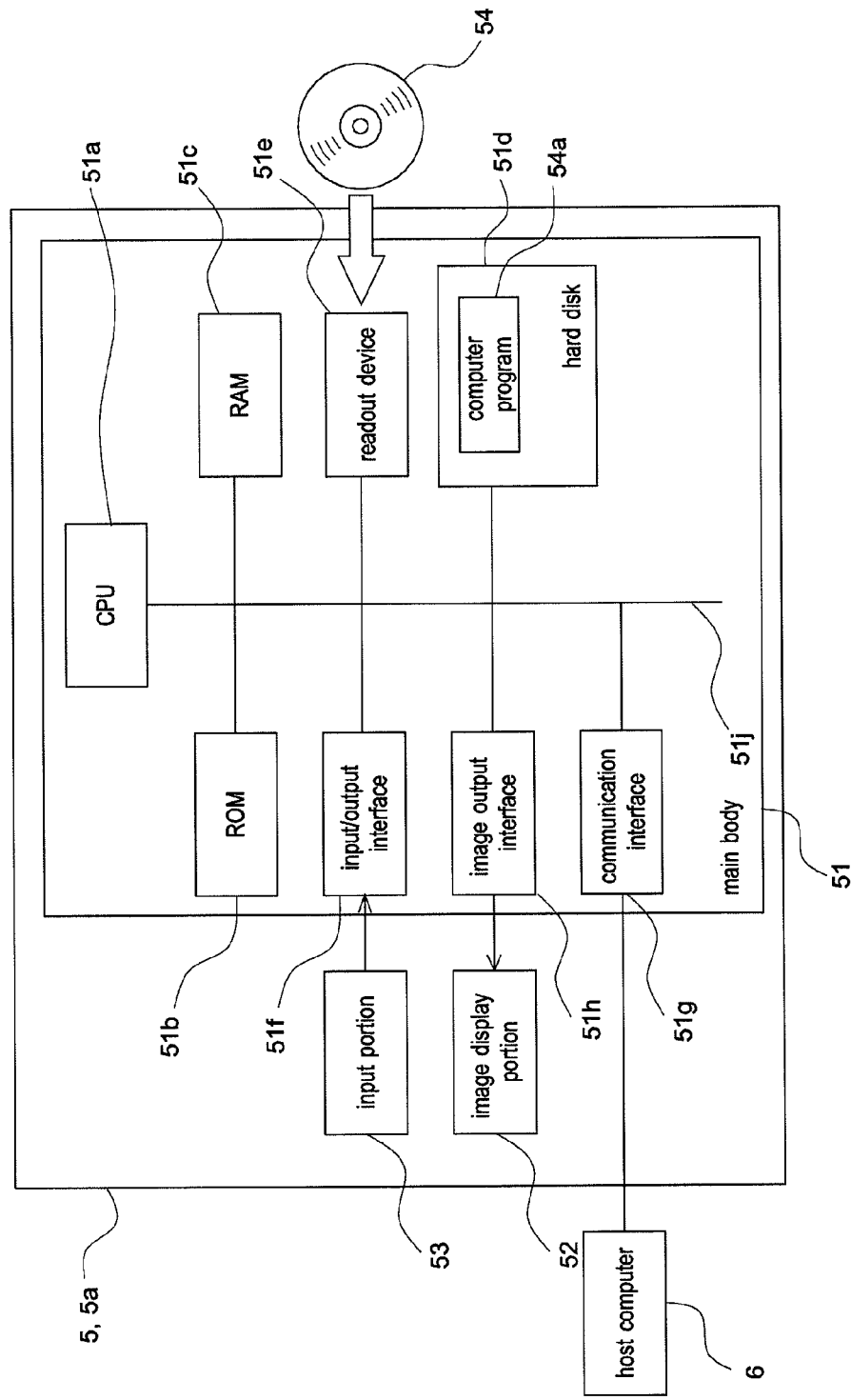
FIG. 6 is a block diagram showing the configuration of an information processing unit according to Embodiment 1.

Next, the configuration of the information processing unit 5 will now be described. The information processing unit 5 is composed of a computer. FIG. 6 is a block diagram showing the configuration of the information processing unit 5. The information processing unit 5 can be implemented by a computer 5a. As shown in FIG. 6, the computer 5a includes a main body 51, an image display portion 52, and an input portion 53. The main body 51 includes a CPU 51a, a ROM 51b, a RAM 51c, a hard disk 51d, a readout device 51e, an input/output interface 51f, a communication interface 51g, and an image output interface 51h. The CPU 51a, the ROM 51b, the RAM 51c, the hard disk 51d, the readout device 51e, the input/output interface 51f, the communication interface 51g, and the image output interface 51h are connected by a bus 51j.

The CPU 51a can execute a computer program loaded into the RAM 51c. The computer 5a functions as the information processing unit 5 by the CPU 51a executing a computer program 54a for a blood analysis and control of the measurement unit 2 and the specimen carrying unit 4 as will be described later.

The ROM 51b is composed of mask ROM, PROM, EPROM, EEPROM, or the like, and a computer program executed by the CPU 51a, data used therefor, and the like are stored thereon.

The RAM 51c is composed of SRAM, DRAM, or the like. The RAM 51c is used for reading out the computer program 54a stored on the hard disk 51d. When the CPU51a executes a computer program, the RAM 51c is used as a work area of the CPU51a.

Various computer programs, including, for example, an operating system and application programs, for being executed by the CPU 51a, and the data used for execution of such computer programs are installed on the hard disk 51d. The computer program 54a, which will be described later, is also installed on the hard disk 51d. The computer program 54a is an event-driven computer program.

The readout device 51e is configured by a flexible disk drive, a CD-ROM drive, a DVD-ROM drive, or the like, and can read out the computer programs or data stored on a portable recording medium 54. The computer program 54a for enabling the computer to function as the information processing unit 5 is stored on the portable recording medium 54. The computer 5a can read out the computer program 54a from the portable recording medium 54, and install the computer program 54a on the hard disk 51d.

The computer program 54a is not only provided by the portable recording medium 54 but it may also be provided through an electric telecommunication line from an external apparatus communicatively connected to the computer 5a via the electric telecommunication line (regardless of being wired or wireless). For example, it is possible that the computer program 54a is stored on the hard disk of a server computer on the Internet, and the computer 5a accesses the server computer, downloads the computer program, and installs the computer program on the hard disk 51d.

For example, a multitasking operating system such as Windows (registered trademark) manufactured and sold by Microsoft Corporation, US is installed on the hard disk 51d. The following description is given assuming that the computer program 54a of this embodiment runs on the aforementioned operating system.

The input/output interface 51f is composed of, for example, a serial interface such as USB, IEEE1394, or RS-232C, a parallel interface such as SCSI, IDE, or IEEE1284, and an analog interface made up of a D/A converter, an A/D converter, and the like. An input portion 53 made up of a keyboard and a mouse is connected to the input/output interface 51f, and the user can input data into the computer 5a using the input portion 53. Furthermore, the input/output interface 51f is connected to the measurement unit 2 and the specimen carrying unit 4. This enables the information processing unit 5 to control both the measurement unit 2 and the specimen carrying unit 4.

The communication interface 51g is an Ethernet (registered trademark) interface. The communication interface 51g is connected to a host computer 6 via a LAN (see FIG. 4). The computer 5a can transmit and receive data via the communication interface 51g to and from the host computer 6 connected to the LAN using a predetermined communications protocol.

The image output interface 51h is connected to the image display portion 52 composed of an LCD, a CRT, or the like, and is configured to output to the image display portion 52 an image signal that corresponds to the image data provided by the CPU 51a. The image display portion 52 displays an image (screen) according to the input image signal.

[Measuring Operation of Blood Analyzer 1]

Below, the operation of the blood analyzer 1 of this embodiment will now be described.

<Specimen Measuring Operation>

First, the specimen measuring operation of the blood analyzer 1 of this embodiment will now be described. The blood analyzer 1 can execute measurement of B-lymphocytes and T-lymphocytes using the optical detector D. The steps of this measurement include a measurement step of measuring a B•T-lymphocyte measurement sample and a data processing step of analysis-processing the measurement data obtained in the measurement step.

First, the sample rack L retaining the specimen container T is placed on a pre-analysis rack retaining portion 41 by the operator. A rack delivering portion 41b is engaged with the sample rack L placed on the pre-analysis rack retaining portion 41, and the sample rack L is carried rearward and delivered to a rack carrying portion 43. Thereafter, the sample rack L is carried by the rack carrying portion 43, and the specimen container T in which a specimen to be measured is accommodated is positioned in the specimen supply position 43a. Next, the specimen container T is gripped by the hand portion 25a of the measurement unit 2, and the specimen container T is removed from the sample rack L. The hand portion 25a then performs oscillating movement, thereby agitating the specimen inside the specimen container T. Next, the specimen container T is inserted into the specimen container setting portion 25b, and the specimen container setting portion 25b is moved in the Y direction. After the bar code of the specimen is read by the bar code reading portion 26, the specimen container T reaches the suction position. Then, the measurement step described below is performed.

Measurement Step

First, the measurement step will now be described. In the measurement step, the blood analyzer 1 mixes a whole blood specimen, a first reagent, and a second reagent to prepare a B•T-lymphocyte measurement sample, and measures the B•T-lymphocyte measurement sample by flow cytometry with the optical detector D.

Here, the aforementioned Stromatolyser 4DL was used as the first reagent. The aforementioned Stromatolyser 4DS was used as the second reagent.

Figure 7:
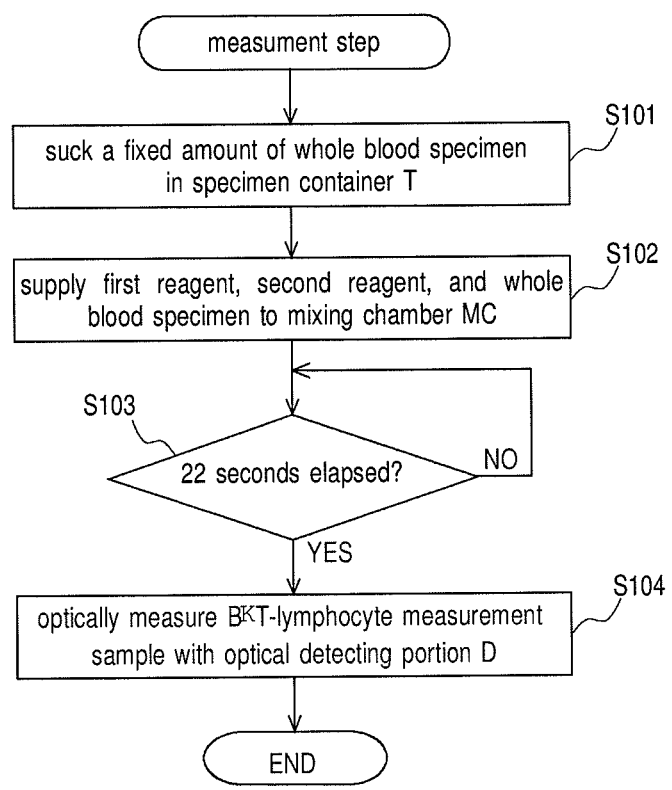
FIG. 7 is a flowchart illustrating the procedure of operation in a measurement step performed by the blood analyzer according to Embodiment 1.

FIG. 7 is a flowchart illustrating the procedure of operation performed by the blood analyzer 1 in the measurement step. First, the CPU 51a controls the specimen suction portion 21 to suck a fixed amount of the whole blood specimen in the specimen container T with the suction tube 211 (step S101). Specifically, in the processing of step S101, the suction tube 211 is inserted into the specimen container T, and a fixed amount (39.0 μL) of the whole blood specimen is sucked by driving the syringe pump.

Next, the CPU 51a controls the measurement unit 2 so as to supply, to the mixing chamber MC, the first reagent (1 mL) from the reagent container 221, the first reagent (30 μL) from the reagent container 222, and the whole blood specimen (11 μL) from the suction tube 211. More specifically, the whole blood specimen is supplied to the chamber MC, and then the first reagent and the second reagent are supplied to the chamber MC (Step S102). Next, the CPU 51a waits for 22 seconds and determines whether 22 seconds have elapsed since the supply of the first reagent and the second reagent to the mixing chamber MC (step S103). Here, the mixing chamber MC has been heated to 35° C. by the heater. Thus, the mixture of the first reagent, the second reagent, and the blood specimen is heated at 35° C. for 22 seconds, preparing the B•T-lymphocyte measurement sample.

Then, optical measurement is performed on the B•T-lymphocyte measurement sample with the optical detector D (step S104). Specifically, in the processing of step S104, the B•T-lymphocyte measurement sample and the sheath fluid are simultaneously supplied to the flow cell 231 of the optical detector D. At this time, forward scattered light is received by the photodiode 243, side scattered light is received by the photodiode 246 and is received by the avalanche photodiode 248. Output signals (analog signals) output from these various light-receiving elements of the optical detector D are converted into digital signals by an A/D converter (not shown), and then converted into digital measurement data through predetermined signal processing performed by a signal processing circuit (not shown). The measurement data is transmitted to the information processing unit 5. In this signal processing, a forward scattered light signal (forward scattered light intensity), a side scattered light signal (side scattered light intensity), and a fluorescence signal (fluorescence intensity) are obtained as feature parameters contained in the measurement data. This completes the measurement step. As will be described later, the CPU 51a of the information processing unit 5 performs predetermined analysis-processing on the measurement data to generate analysis result data containing numerical data for NEUT, LYMPH, EO, BASO, MONO, WBC, and the like, and stores the analysis result data in the hard disk 51d.

Data Processing Step

Figure 8:
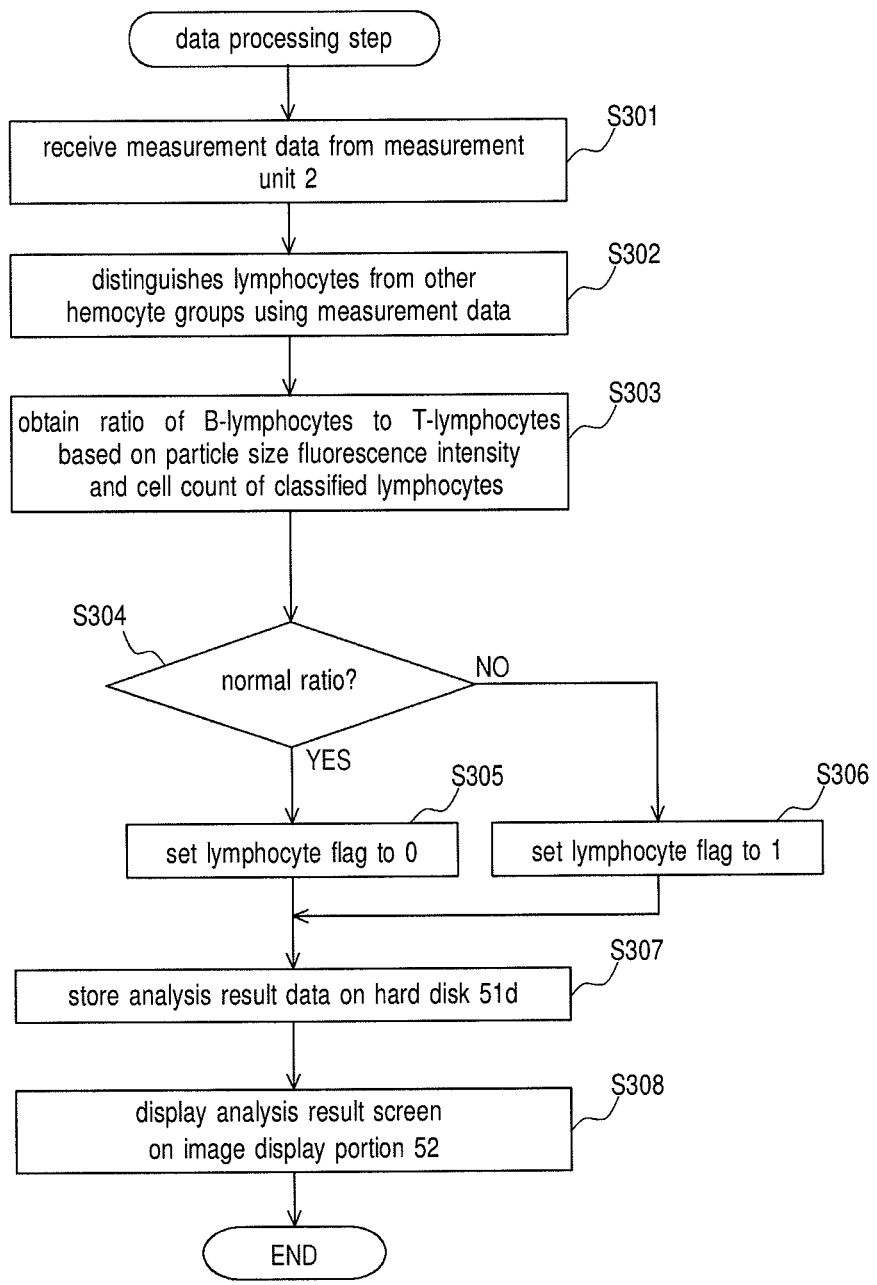
FIG. 8 is a flowchart illustrating the procedure of processing in a data processing step performed by the blood analyzer according to Embodiment 1.

Next, the data processing step will now be described. FIG. 8 is a flowchart illustrating the procedure of processing in the data processing step performed by the blood analyzer 1. The information processing unit 5 of the blood analyzer 1 receives measurement data from the measurement unit 2 (step S301). The computer program 54a, which is executed by the CPU 51a, is an event-driven program, and the processing of step S302 is invoked upon occurrence of an event of receiving the measurement data.

In step S302, the CPU 51a distinguishes lymphocytes from other hemocyte groups using the measurement data (step S302). Next, the ratio of B-lymphocytes to T-lymphocytes is measured based on the fluorescence intensity and the cell count of the classified lymphocytes (step S303). This processing will now be described in detail.

Figure 9:
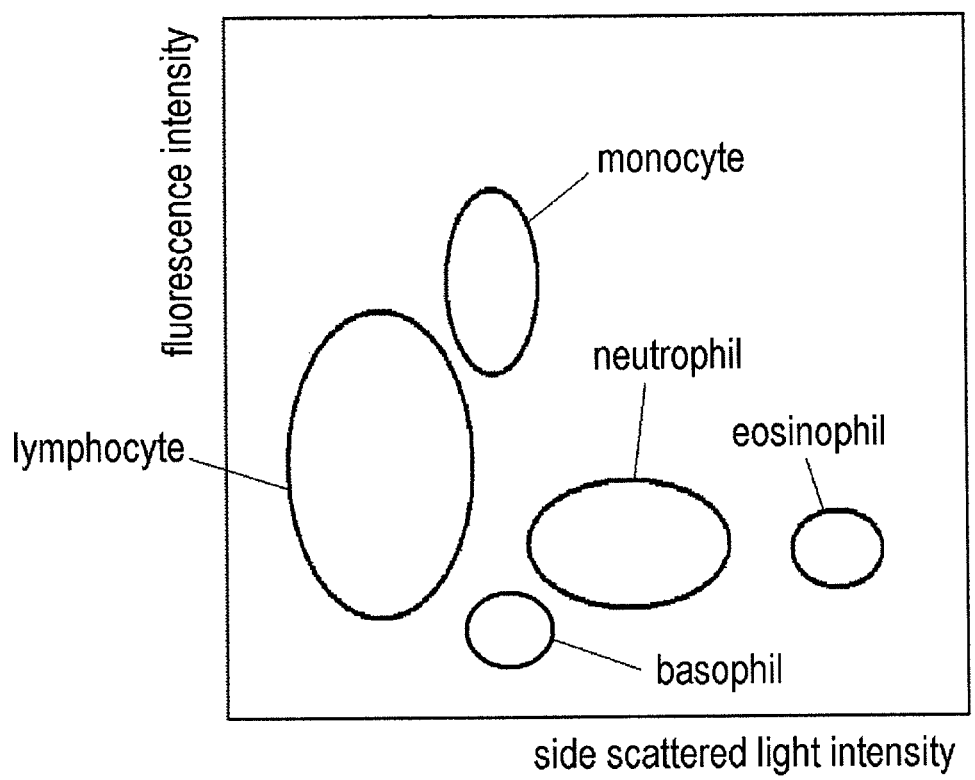
FIG. 9 is a scattergram representing side scattered light intensity and fluorescence intensity in measurement data.
Figure 10:
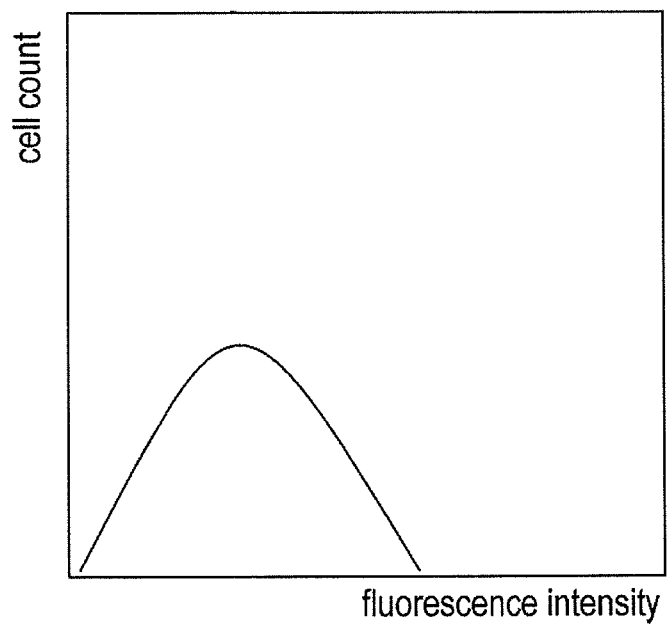
FIG. 10 is a histogram representing fluorescence intensity and cell count in a blood specimen having a large number of B-lymphocytes.
Figure 11:
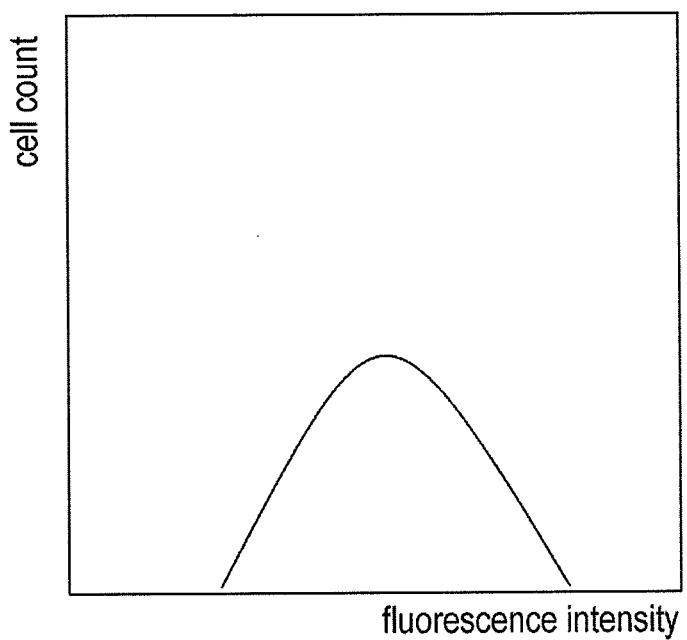
FIG. 11 is a histogram representing fluorescence intensity and cell count in a blood specimen having a large number of T-lymphocytes.

FIG. 9 is a scattergram representing side scattered light intensity and fluorescence intensity in the measurement data. FIGS. 10 and 11 each show a histogram representing the fluorescence intensity and the cell count of the classified lymphocytes.

A cluster of monocytes, a cluster of lymphocytes, a cluster of neutrophils, and a cluster of eosinophils appear in the scattergram representing side scattered light intensity and fluorescence intensity in the measurement data shown in FIG. 9. FIG. 9 is a scattergram of leucocytes classified into five types: NEUT (neutrophil), LYMPH (lymphocyte), EO (eosinophil), BASO (basophil), and MONO (monocyte). In the processing of step S302, the CPU 51a distinguishes the lymphocyte cluster from other clusters using the side scattered light intensity and the fluorescence intensity in the measurement data. FIG. 10 is a histogram representing the fluorescence intensity and the cell count of a blood specimen having a large number of B-lymphocytes. FIG. 11 is a histogram representing the fluorescence intensity and the cell count of a blood specimen having a large number of T-lymphocytes. The histograms representing fluorescence intensity and cell count show that the fluorescence intensity of the B-lymphocyte peak is lower than that of the T-lymphocyte peak. In other words, the fluorescence intensity of the T-lymphocyte peak is higher than that of the B-lymphocyte peak. In the processing of step S303, the CPU 51a obtains the ratio of B-lymphocytes to T-lymphocytes in the lymphocyte cluster distinguished in step S302 based on information regarding a particle size distribution representing fluorescence intensity and cell count.

Next, in step S304, the CPU 51a determines whether the ratio of B-lymphocytes to T-lymphocytes obtained in step S303 is within a predetermined range (normal range) (step S304). Here, the normal range can be set in advance based on the ratio of B-lymphocytes to T-lymphocytes in a plurality of blood specimens. Therefore, in the case where the ratio of B-lymphocytes to T-lymphocytes is in the normal range in this processing (YES in step S304), it can be judged that there is no abnormality of lymphocytes in the blood specimen. Therefore, in this case, the CPU 51a sets a lymphocyte flag provided in the RAM 51c to "0" (step S305). Here, the lymphocyte flag is a flag that indicates the presence or absence of an abnormality of lymphocytes in a blood specimen. The lymphocyte flag when set to "1" indicates that lymphocytes are abnormal, and when set to "0" indicates that lymphocytes are normal. Then, the processing executed by the CPU 51a advances to step S307.

On the other hand, in the case where the ratio of B-lymphocytes to T-lymphocytes is not within the normal range in step S304 (NO in step S304), it can be judged that there is an abnormality of lymphocytes in a blood specimen. Therefore, in this case, the CPU 51a sets the lymphocyte flag to "1" (step S306). Then, the processing executed by the CPU 51a advances to step S307.

In step S307, the CPU 51a stores the analysis result thus obtained on the hard disk 51d (step S307). Next, the CPU 51a causes the image display portion 52 to show a screen displaying the analysis result stored on the hard disk 51d (step S308), and terminates data processing.

Figure 12:
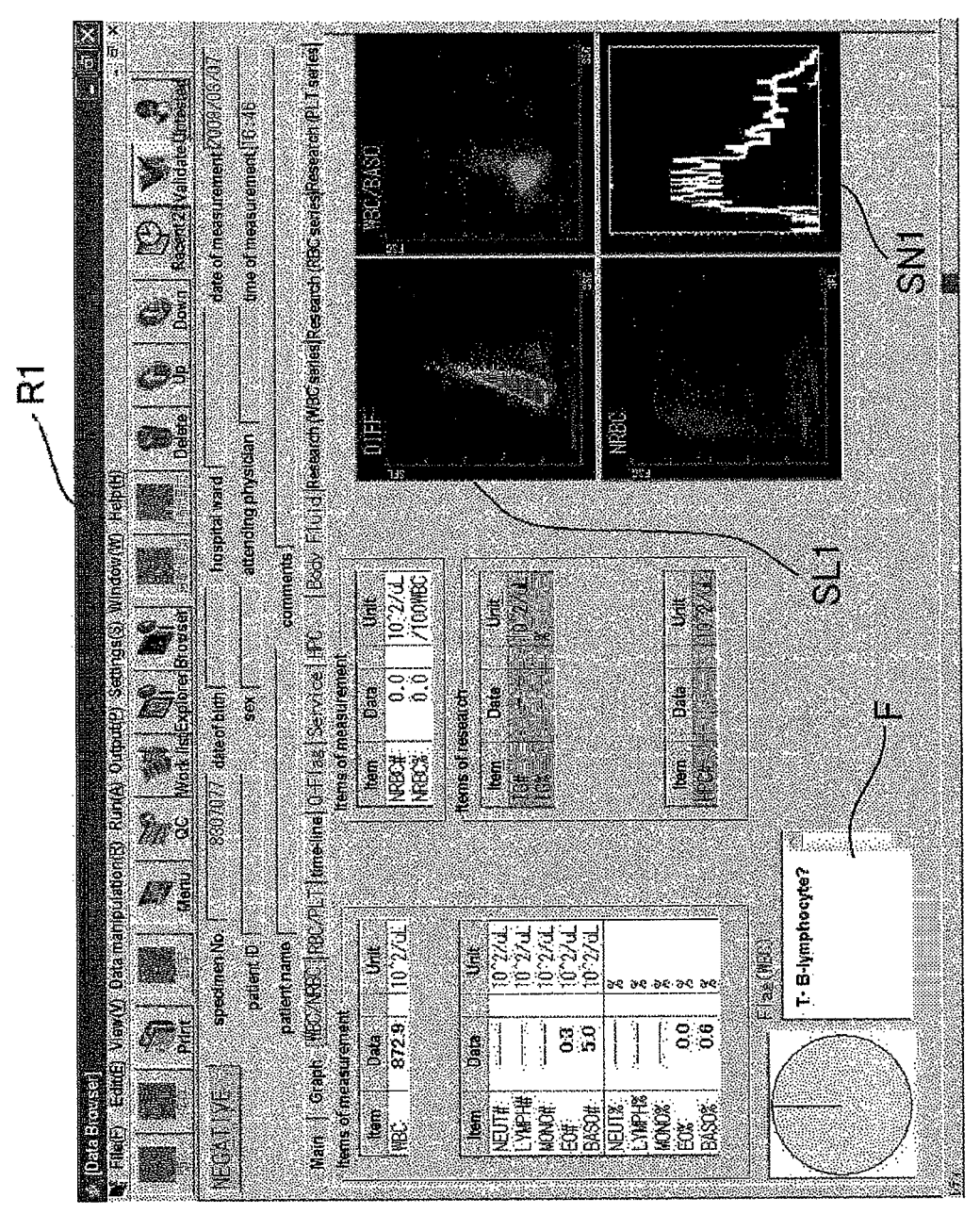
Figure 13:
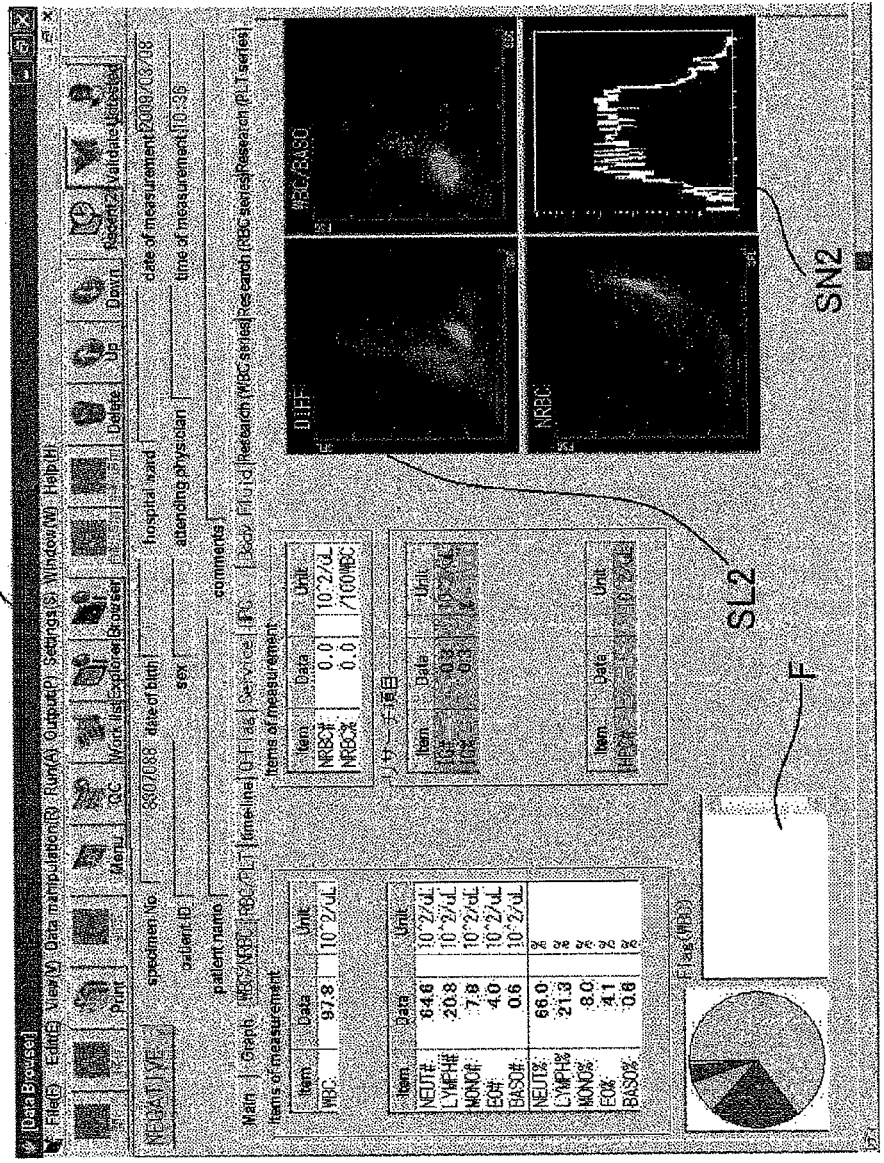
FIG. 13 is a picture showing a screen displaying results of analyzing a blood specimen B having a normal ratio of a B-lymphocyte count to a T-lymphocyte count in Embodiment 1.

FIGS. 12 and 13 are diagrams showing screens of the blood analyzer 1 displaying analysis results. FIG. 12 shows a screen displaying results of analyzing a blood specimen A. FIG. 13 shows a screen displaying results of analyzing a blood specimen B. As shown in FIGS. 12 and 13, numerical data of the measured measurement items (WBC, RBC, PLT, NRBC, etc.) is displayed on analysis result screens R1 and R2. The blood specimen A is a specimen having an abnormal B-lymphocyte to T-lymphocyte ratio, and in the analysis result data of the blood specimen A, the lymphocyte flag is set to "1". Accordingly, on the analysis result screen R1 for the blood specimen A, as shown in FIG. 12, the "T•B-lymphocyte?", which is information indicating a possibility of the presence of a lymphocyte abnormality, is displayed in a Flag field F. On the other hand, the blood specimen B is a specimen having a normal B-lymphocyte to T-lymphocyte ratio, and in the analysis result data of the blood specimen B, the lymphocyte flag is set to "0". Therefore, on the analysis result screen R2 for the blood specimen B, the aforementioned "T•B-Lymphocyte?" is not displayed in the Flag field F of FIG. 13. In addition, scattergrams SL1 and SL2 representing side scattered light intensity and fluorescence intensity of the measurement data appear on the analysis result screens R1 and R2, respectively. Furthermore, histograms SN1 and SN2 representing fluorescence intensity of lymphocytes and cell count appear on the analysis result screens R1 and R2, respectively. By referring to these scattergrams, the operator can obtain the basis of the detection result that indicates the presence or absence of a lymphocyte abnormality provided by the blood analyzer 1. Also, the operator can determine whether the detection result that indicates the presence or absence of a lymphocyte abnormality provided by the blood analyzer 1 is reasonable or not.

With the configuration described above, the blood analyzer 1 can measure the ratio of B-lymphocytes to T-lymphocytes by measuring, with the optical detector D, a B•T-lymphocyte measurement sample prepared by mixing a second reagent containing a hemolyzing agent, a blood specimen, and a second reagent containing a fluorescent dye for staining nucleic acid. That is, the ratio of B-lymphocytes to T-lymphocytes can be measured without using a fluorescence-labeled antibody, and thus a cost reduction can be attained. Moreover, use of the blood analyzer 1 enables a lymphocyte abnormality to be determined without using a fluorescence-labeled antibody.

Embodiment 2

The blood analyzer of this embodiment includes a measurement unit 2 and an information processing unit 5, and the measurement unit 2 includes a detecting portion 23 having an optical detector D that can perform WBC measurement (leucocyte counting) and DIFF measurement (leucocyte classification). The optical detector D of this embodiment is configured to be capable of detecting WBCs (mature leucocytes), NRBCs (nucleated erythrocytes), and lymphoblasts (L-Blasts) by flow cytometry using a semiconductor laser. Use of the detecting portion 23 enables leukocytes to be classified into four types: LYMPH (lymphocyte), EO (eosinophil), NEUT+BASO (neutrophil+basophil), and MONO (monocyte); or five types: NEUT (neutrophil), LYMPH (lymphocyte), EO (eosinophil), BASO (basophil), and MONO (monocyte). When measuring B-lymphocytes and T-lymphocytes, a measurement sample (a B•T-lymphocyte measurement sample) in which a blood specimen, a first reagent, and a second reagent are mixed is supplied to the optical detector D.

In the blood analyzer of this embodiment, a computer program for causing the CPU 51a to execute processing, which will be described later, is installed on the hard disk 51d. Other configurations of the blood analyzer of this embodiment are identical to those of the blood analyzer of Embodiment 1. Therefore, the same components are given the same reference numbers, and the description thereof is omitted.

Next, the operation of the blood analyzer according to this embodiment will now be described. The blood analyzer according to this embodiment is capable of performing a specimen measuring operation including a measurement step and a data processing step. The measurement step for the specimen analyzer according to this embodiment is identical to the measurement step of the specimen analyzer 1 according to Embodiment 1. Therefore, the description thereof is omitted.

Figure 14:
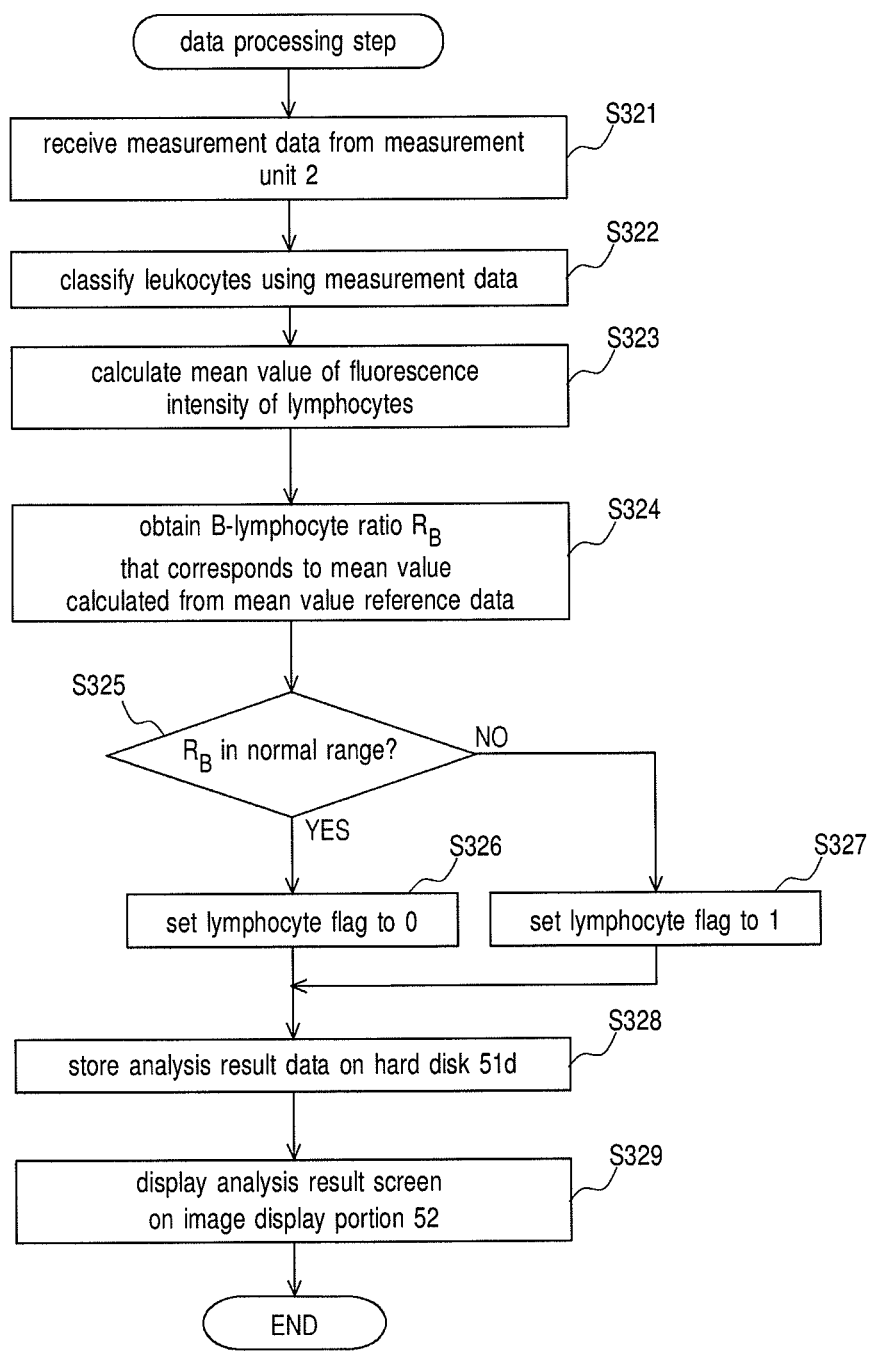
FIG. 14 is a flowchart illustrating the procedure of operation in a measurement step performed by a blood analyzer according to Embodment 2.

FIG. 14 is a flowchart showing the procedure of processing in the data processing step performed by the blood analyzer according to this embodiment. The information processing unit 5 of the blood analyzer receives measurement data from the measurement unit 2 (step S321). The computer program according to this embodiment, which is executed by the CPU 51a, is an event-driven program, and the processing of step S322 is invoked upon occurrence of an event of receiving the measurement data.

In step S322, the CPU51a classifies leucocytes into four groups (LYMPH, EO, NEUT+BASO, and MONO) using the measurement data (step S322). Next, the CPU51a calculates the mean value of the fluorescence intensity of the classified lymphocytes (step S323).

As will be described in detail below, the mean value, the median value, the difference between the mean value and the median value, and the root-mean-square (RMS), which are measures of central tendency of the fluorescence intensity of lymphocytes (numerical values that serve as objective scales showing the characteristics or the tendency of data), monotonically change relative to the ratio of B-lymphocytes to T-lymphocytes. That is, the mean value, the median value, the difference between the mean value and the median value, and the RMS of the fluorescence intensity of lymphocytes each correspond to the ratio of B-lymphocytes to T-lymphocyteares. More specifically, the mean value, the median value, the difference between the mean value and the median value, and RMS of the fluorescence intensity of lymphocytes each linearly change as the B-lymphocyte ratio (ratio of the B-lymphocyte count to the total T-lymphocyte and B-lymphocyte count) is increased (see FIGS. 25A, 25B, 25C, and 25I). In the blood analyzer according to this embodiment, mean value reference data that is a look-up table showing the relationship between the mean value of the fluorescence intensity of lymphocytes and the B-lymphocyte ratio is stored on the hard disk 51d. By referring to the mean value reference data, the CPU 51a obtains a B-lymphocyte ratio $R_B$ that corresponds to the calculated mean value of the fluorescence intensity of lymphocytes (step S324). Here, the mean value reference data is a look-up table, but a configuration may be adopted in which a mathematical expression showing the relationship between the mean value of the fluorescence intensity of lymphocytes and the B-lymphocyte ratio is stored as the mean value reference data in advance, and a B-lymphocyte ratio $R_B$ that corresponds to the mean value of the fluorescence intensity of lymphocytes is obtained using the mathematical expression.

Next, the CPU 51a determines whether the B-lymphocyte ratio $R_B$ is in a predetermined normal range (step S325). Here, the normal range is set in advance according to the B-lymphocyte ratios of blood specimens collected from healthy people and patient blood specimens from patients exhibiting abnormal B-lymphocyte ratios, and is stored on the hard disk 51d. In this embodiment, the normal range of the B-lymphocyte ratio is "5% to 20%". In the case where the B-lymphocyte ratio $R_B$ is in the normal range (YES in step S325), the CPU 51a sets a lymphocyte flag provided in the RAM 51c to "0" (step S326). Then, the processing executed by the CPU 51a advances to step S328. The lymphocyte flag is the same as in Embodiment 1, and therefore the description thereof is omitted.

On the other hand, in the case where the B-lymphocyte ratio $R_B$ is not in the normal range (NO in step S325), the CPU 51a sets the lymphocyte flag to "1" (step S327). Then, the processing executed by the CPU 51a advances to step S328.

In step S328, the CPU 51a stores the analysis result thus obtained on the hard disk 51d (step S328). Next, the CPU 51a causes the image display portion 52 to show a screen displaying the analysis result stored on the hard disk 51d (step S329), and terminates data processing.

Figure 15:
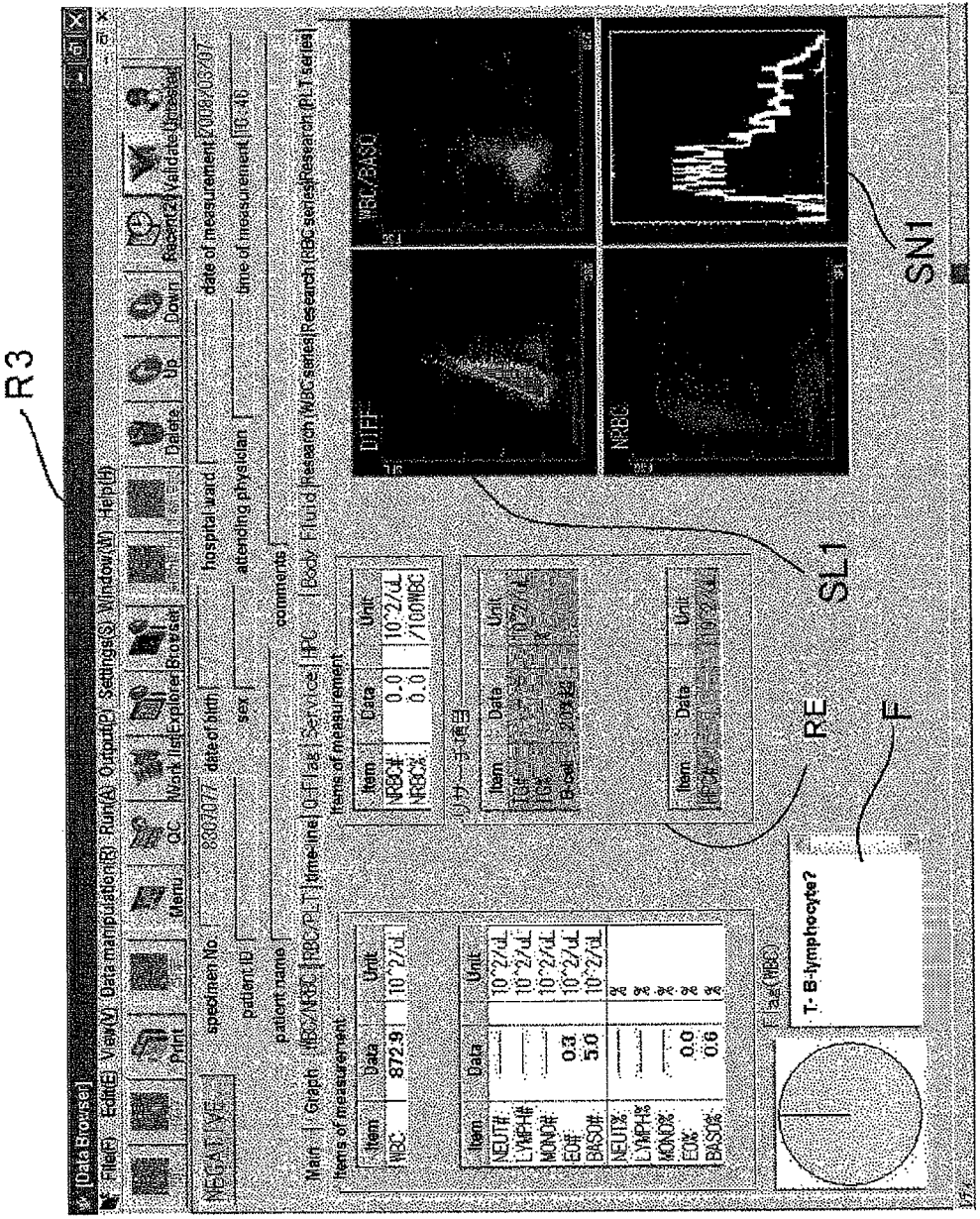
FIG. 15 is a picture showing a screen displaying results of analyzing a blood specimen A having an abnormal ratio of a B-lymphocyte count to a T-lymphocyte count in Embodiment 2.

FIG. 15 is a diagram showing an example of the analysis result screen of the blood analysis apparatus according to this embodiment. As shown in FIG. 15, the B-lymphocyte ratio $R_B$ is displayed on an analysis result screen R3 as a research item used for a reference for diagnosis. Specifically, the term "B-cell" that indicates the B-lymphocyte ratio is displayed in an item field provided in a research item display area RE, and the phrase "more than 20%" that is numerical data of the B-lymphocyte ratio $R_B$ is displayed in a data field. In the blood analyzer according to this embodiment, a range to which the B-lymphocyte ratio $R_B$ belongs is displayed, for example, in the case where the B-lymphocyte ratio $R_B$ exceeds 20%, the phrase "more than 20%" is displayed, in the case of 5 to 20%, "5 to 20%", and in the case of less than 5%, "less than 5%". By referring to this B-lymphocyte ratio $R_B$, the operator can find out the ratio of B-lymphocytes present in the lymphocytes provided by the blood analyzer 1. Other configurations of the analysis result screen R3 of the blood analyzer according to this embodiment are the same as the analysis result screen R1 of the blood analyzer according to Embodiment 1. Therefore, the description thereof is omitted.

Embodiment 3

In the blood analyzer of this embodiment, a computer program for causing the CPU 51a to execute processing, which will be described later, is installed on the hard disk 51d. Other configurations of the blood analyzer of this embodiment are identical to those of the blood analyzer of Embodiment 2. Therefore, the same components are given the same reference numbers, and the description thereof is omitted.

Next, the operation of the blood analyzer according to this embodiment will now be described. The blood analyzer according to this embodiment is capable of performing a specimen measuring operation including a measurement step and a data processing step. The measurement step for the specimen analyzer according to this embodiment is identical to the measurement step of the specimen analyzer 1 according to Embodiment 1. Therefore, the description thereof is omitted.

Figure 16:
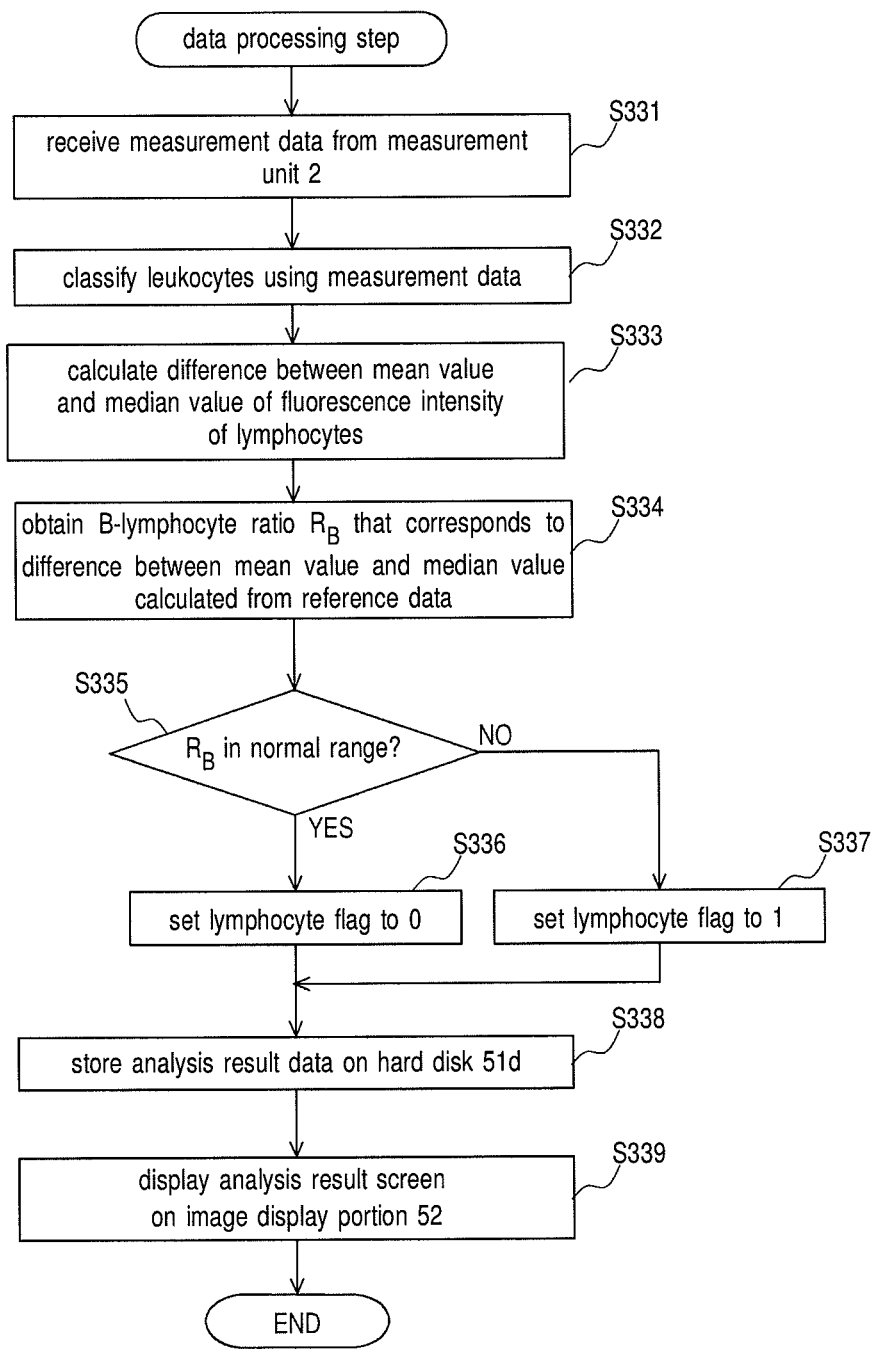
FIG. 16 is a flowchart illustrating the procedure of operation in a measurement step performed by a blood analyzer according to Embodiment 3.

FIG. 16 is a flowchart showing the procedure of processing in the data processing step performed by the blood analyzer according to this embodiment. The processing of steps S331 and S332 is the same as that of steps S321 and S322 described in Embodiment 2, and therefore the description thereof is omitted. In step S333, the CPU 51a calculates both the mean value and the median value of the fluorescence intensity of the classified lymphocytes, and calculates the difference between the mean value and the median value obtained (step S333).

In the blood analyzer according to this embodiment, reference data that is a look-up table showing the relationship between the B-lymphocyte ratio and the difference between the calculated mean value and median value of the fluorescence intensity of lymphocytes is stored on the hard disk 51d. By referring to the reference data, the CPU 51a obtains a B-lymphocyte ratio $R_B$ that corresponds to the difference between the mean value and the median value of the fluorescence intensity of lymphocytes (step S334). Here, the reference data is a look-up table, but a configuration may be adopted in which a mathematical expression showing the relationship between the B-lymphocyte ratio and the difference between the mean value and the median value of the fluorescence intensity of lymphocytes is stored as the reference data in advance, and a B-lymphocyte ratio $R_B$ that corresponds to the difference between the mean value and the median value of the fluorescence intensity of lymphocytes is obtained using the mathematical expression.

The processing of steps S335 to S339 is the same as that of steps S325 to S329 described in Embodiment 2, and therefore the description thereof is omitted.

Embodiment 4

In the blood analyzer of this embodiment, a computer program for causing the CPU 51a to execute processing, which will be described later, is installed on the hard disk 51d. Other configurations of the blood analyzer of this embodiment are identical to those of the blood analyzer of Embodiment 2. Therefore, the same components are given the same reference numbers, and the description thereof is omitted.

Next, the operation of the blood analyzer according to this embodiment will now be described. The blood analyzer according to this embodiment is capable of performing a specimen measuring operation including a measurement step and a data processing step. The measurement step for the specimen analyzer 1 according to this embodiment is identical to the measurement step of the specimen analyzer according to Embodiment 1. Therefore, the description thereof is omitted.

Figure 17:
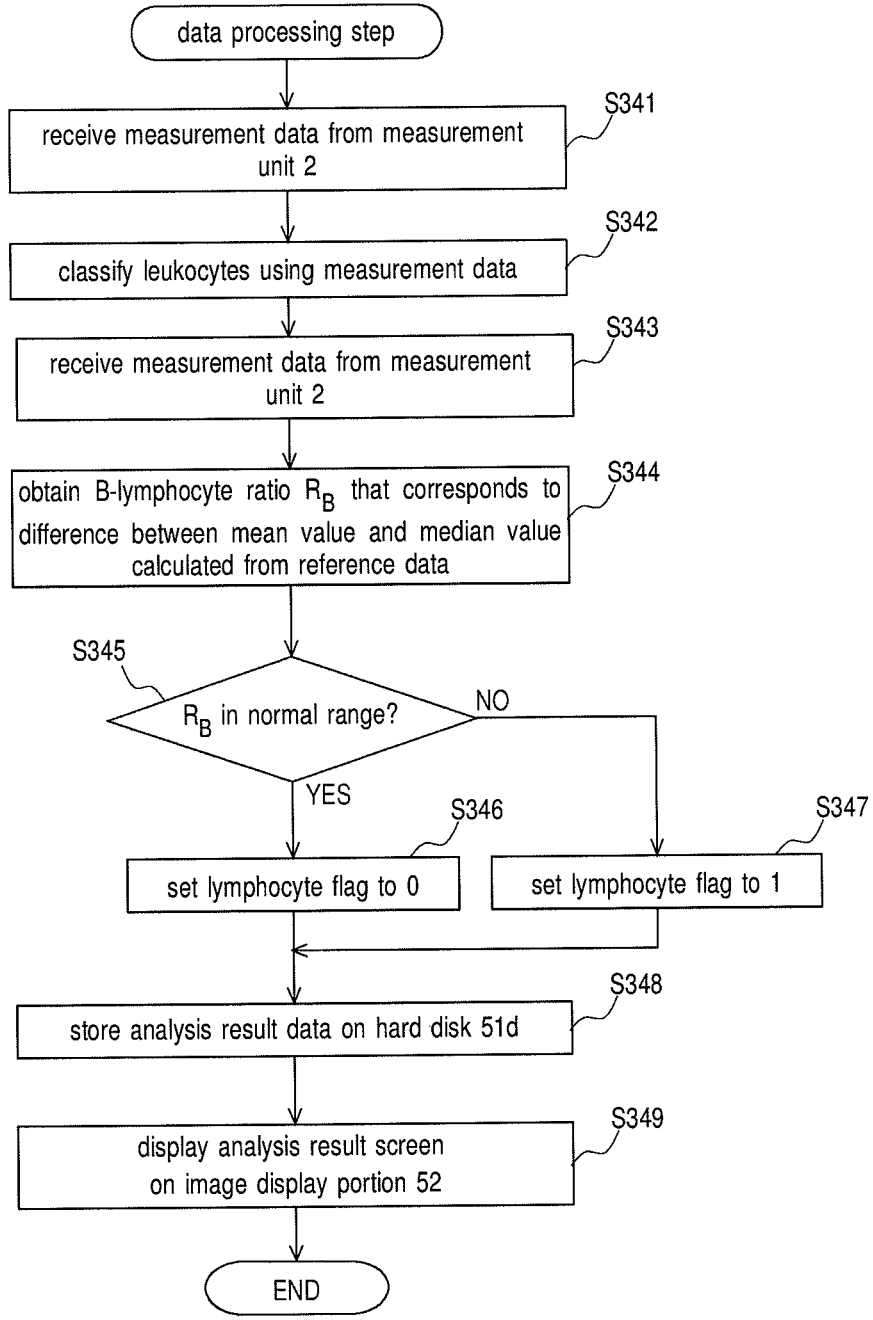
FIG. 17 is a flowchart illustrating the procedure of operation in a measurement step performed by a blood analyzer according to Embodiment 4.

FIG. 17 is a flowchart showing the procedure of processing in the data processing step performed by the blood analyzer according to this embodiment. The processing of steps S341 and S342 is the same as that of steps S321 and S322 described in Embodiment 2, and therefore the description thereof is omitted. In step S343, the CPU 51a calculates the skewness of the fluorescence intensity of the classified lymphocytes (step S343).

As will be described later, the skewness of the fluorescence intensity of lymphocytes is monotonously changed relative to the ratio of B-lymphocytes to T-lymphocytes. That is, the skewness of the fluorescence intensity of lymphocytes corresponds to the ratio of B-lymphocytes to T-lymphocyteares. More specifically, the skewness of the fluorescence intensity of lymphocytes is linearly increased as the B-lymphocyte ratio is increased (see FIG. 25D). The position where B-lymphocytes appear and the position where T-lymphocytes appear according to the fluorescence intensity are different. Accordingly, as the B-lymphocyte ratio is increased, the position (peak) where fluorescence intensity is concentrated approaches the position where B-lymphocytes appear, and as the T-lymphocyte ratio is increased, the position (peak) where fluorescence intensity is concentrated approaches the position where T-lymphocytes appear (see FIGS. 24A to 24I). Therefore, when the ratio of B-lymphocytes to T-lymphocytes is changed, the shape of the distribution of the fluorescence intensity of lymphocytes is changed, and according to this change, the skewness is changed. That is, it can be said that skewness shows characteristics of the distribution of the fluorescence intensity of lymphocytes, and represents a bias in the distribution of the fluorescence intensity of lymphocytes. In the blood analyzer according to this embodiment, skewness reference data that is a look-up table showing the relationship between the skewness of the fluorescence intensity of lymphocytes and the B-lymphocyte ratio is stored on the hard disk 51d. By referring to the skewness reference data, the CPU 51a obtains a B-lymphocyte ratio that corresponds to the calculated skewness of the fluorescence intensity of lymphocytes (step S344). Here, the skewness reference data is a look-up table, but a configuration may be adopted in which a mathematical expression showing the relationship between the skewness of the fluorescence intensity of lymphocytes and the B-lymphocyte ratio is stored as the skewness reference data in advance, and a B-lymphocyte ratio that corresponds to the skewness of the fluorescence intensity of lymphocytes is obtained using the mathematical expression.

Embodiment 5

In the blood analyzer of this embodiment, a computer program for causing the CPU 51a to execute processing, which will be described later, is installed on the hard disk 51d. Other configurations of the blood analyzer of this embodiment are identical to those of the blood analyzer of Embodiment 2. Therefore, the same components are given the same reference numbers, and the description thereof is omitted.

Next, the operation of the blood analyzer according to this embodiment will now be described. The blood analyzer according to this embodiment is capable of performing a specimen measuring operation including a measurement step and a data processing step. The measurement step for the specimen analyzer according to this embodiment is identical to the measurement step of the specimen analyzer 1 according to Embodiment 1. Therefore, the description thereof is omitted.

Figure 18:
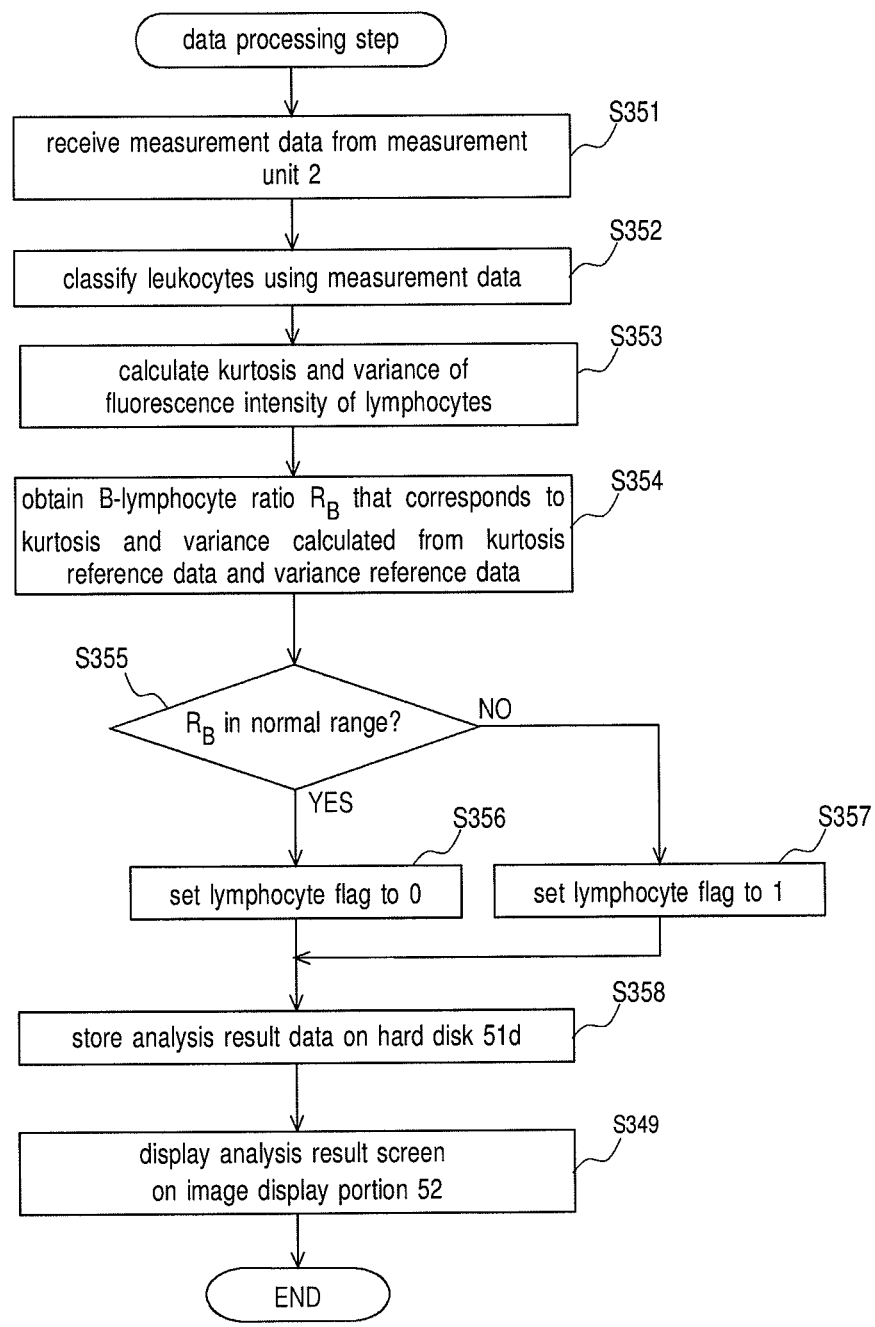
FIG. 18 is a flowchart illustrating the procedure of operation in a measurement step performed by a blood analyzer according to Embodiment 5.

FIG. 18 is a flowchart showing the procedure of processing in the data processing step performed by the blood analyzer according to this embodiment. The processing of steps S351 and S352 is the same as that of steps S321 and S322 described in Embodiment 2, and therefore the description thereof is omitted. In step S353, the CPU 51a calculates the kurtosis and the dispersion of the fluorescence intensity of the classified lymphocytes (step S353).

As will be described later, the kurtosis of the fluorescence intensity of lymphocytes is monotonically changed relative to the ratio of B-lymphocytes to T-lymphocytes. As the ratio of B-lymphocytes is increased, the distribution of fluorescence intensity is concentrated near the position where B-lymphocytes appear in fluorescence intensity. As the ratio of T-lymphocytes is increased, the distribution of fluorescence intensity is concentrated near the position where T-lymphocytes appear in fluorescence intensity (see FIGS. 24A to 24I). When the B-lymphocyte ratio is increased, a bias in the distribution of fluorescence intensity is increased, and when the ratio of T-lymphocytes is increased, a bias in the distribution of fluorescence intensity is increased. Therefore, when the ratio of B-lymphocytes to T-lymphocytes is changed, the shape of the distribution of the fluorescence intensity of lymphocytes is changed, and according to this change, the kurtosis is changed. That is, it can be said that kurtosis shows characteristics of the distribution of the fluorescence intensity of lymphocytes, and represents a bias in the distribution of the fluorescence intensity of lymphocytes. For example, the kurtosis shown in FIG. 25E is changed mostly linearly in the region where the B-lymphocyte ratio is 30% or greater. That is, the kurtosis of the fluorescence intensity of lymphocytes corresponds to the B-lymphocyte ratio in the aforementioned region.

The dispersion, the standard deviation, and the standard error, which are dispersions of the fluorescence intensity of lymphocytes (numerical values representing the degree of scatter in statistical data), are changed relative to the ratio of B-lymphocytes to T-lymphocytes. Here, combining the dispersion, the standard deviation, or the standard error with the aforementioned kurtosis enables the B-lymphocyte ratio to be identified. For example, the dispersion, the standard deviation, and the standard error shown in FIGS. 25F, 25G, and 25H, respectively, are monotonically increased in the region where the B-lymphocyte ratio is 40% or less, and shows a substantially constant value in the region where the B-lymphocyte ratio is 40% or greater. That is, the dispersion, the standard deviation, and the standard error of the fluorescence intensity of lymphocytes each correspond to the B-lymphocyte ratio in the region where the ratio of B-lymphocytes is 40% or greater. Therefore, in the case where the B-lymphocyte ratio is 40% or greater, the B-lymphocyte ratio can be identified using kurtosis, and in the case where the B-lymphocyte ratio is less than 40%, the B-lymphocyte ratio can be identified using dispersion, standard deviation, or standard error.

In the blood analyzer according to this embodiment, kurtosis reference data that is a look-up table showing the relationship between the kurtosis of the fluorescence intensity of lymphocytes and the B-lymphocyte ratio is stored on the hard disk 51d. Also, dispersion reference data that is a look-up table showing the relationship between the dispersion of the fluorescence intensity of lymphocytes and the B-lymphocyte ratio is stored on the hard disk 51d. In this embodiment, the relationship between the kurtosis of fluorescence intensity and the B-lymphocyte ratio shown in FIG. 25E is stored as kurtosis reference data, and the relationship between the dispersion of fluorescence intensity and the B-lymphocyte ratio shown in FIG. 25F is stored as dispersion reference data. By referring to the kurtosis reference data and the dispersion reference data, the CPU 51a obtains a B-lymphocyte ratio that corresponds to the calculated kurtosis and dispersion of the fluorescence intensity of lymphocytes (step S354). In this processing, the CPU 51a refers to, first, the dispersion reference data, and identifies a B-lymphocyte ratio that corresponds to the obtained dispersion. The dispersion of the fluorescence intensity of lymphocytes shows a substantially constant value in the region where the B-lymphocyte ratio is 40% or greater as described above, and therefore it is difficult to precisely identify the B-lymphocyte ratio in the case where the obtained dispersion is near this constant value. Therefore, in the case where the B-lymphocyte ratio identified using the dispersion reference data is a value less than 40%, the CPU 51a adopts this B-lymphocyte ratio. On the other hand, in the case where the B-lymphocyte ratio identified using the dispersion reference data is a value 40% or greater, the CPU 51a refers to the kurtosis reference data and identifies a B-lymphocyte ratio that corresponds to the obtained kurtosis, and adopts this B-lymphocyte ratio. Here, the dispersion reference data is a look-up table, but a configuration may be adopted in which a mathematical expression showing the relationship between the dispersion of the fluorescence intensity of lymphocytes and the B-lymphocyte ratio is stored as the dispersion reference data in advance, and a B-lymphocyte ratio that corresponds to the dispersion of the fluorescence intensity of lymphocytes is obtained using the mathematical expression. Moreover, a configuration may be adopted in which a mathematical expression showing the relationship between the kurtosis of the fluorescence intensity of lymphocytes and the B-lymphocyte ratio is stored as the kurtosis reference data in advance, and a B-lymphocyte ratio that corresponds to the kurtosis of the fluorescence intensity of lymphocytes is obtained using the mathematical expression.

The processing of steps S355 to S359 is the same as that of steps S325 to S329 described in Embodiment 2, and therefore the description thereof is omitted.

Other Embodiments

The reaction temperature and the reaction time during mixing of the blood specimen, the first reagent, and the second reagent in the sample preparation portion 22 may be suitably set according to the state of damage and staining of the hemocytes contained in the blood specimen, without any particular limitation. Specifically, the reaction time and the reaction temperature may be adjusted such that the reaction time is short when the reaction temperature is high and the reaction time is long when the reaction temperature is low. More specifically, it is preferable that the blood specimen, the first reagent, and the second reagent are mixed at a temperature of 20° C. to 40° C. for 3 to 180 seconds.

Although Embodiments 1 to 5 described above have addressed a configuration in which the first reagent containing a hemolyzing agent and the second reagent containing a fluorescent dye that can stain nucleic acid are used to perform the measurement step, the present invention is not limited thereto. It is possible to prepare the B/T-lymphocyte measurement sample by mixing the blood specimen with a reagent containing both a hemolyzing agent and a nucleic acid staining dye.

Moreover, in Embodiments 1 to 5 described above, a whole blood specimen is used as the blood specimen, but the blood specimen is not limited thereto. Any blood specimen may be used as long as it contains lymphocytes. For example, a sample obtained by collecting a lymphocyte-containing fraction using specific-gravity centrifugation can also be used as the blood specimen. In the case where a sample obtained by collecting a lymphocyte-containing fraction is used as the blood specimen, the ratio of B-lymphocytes to T-lymphocytes can also be measured using fluorescence intensity only.

Although Embodiments 1 to 5 described above have addressed a configuration in which the control of the measurement unit 2 and the processing of measurement data are performed by the CPU 51a executing the aforementioned computer program 54a, the present invention is not limited thereto. It is also possible to adopt a configuration in which the control of the measurement unit 2 and the processing of measurement data are performed by dedicated hardware such as FPGA or ASIC that can perform the same processing as that performed by the aforementioned computer program 54a.

Although Embodiments 1 to 5 described above have addressed a configuration in which the computer 5a singly executes all the processing of the computer program 54a, the present invention is not limited thereto. It is also possible to adopt a distributed system in which the same processing as that of the above-described computer program 54a is executed by a plurality of devices (computers) in a distributed manner.

Although Embodiments 2 to 5 described above have addressed a configuration in which a B-lymphocyte ratio that corresponds to the mean value of the fluorescence intensity of lymphocytes, to the difference between the mean value and the median value of the fluorescence intensity of lymphocytes, to the skewness of the fluorescence intensity of lymphocytes, and to the combination of the kurtosis and the dispersion of the fluorescence intensity of lymphocytes is obtained, the present invention is not limited thereto. A configuration may be adopted in which data showing the relationship between the T-lymphocyte ratio (ratio of T-lymphocytes to the total B-lymphocyte and T-lymphocyte count) and the mean value of the fluorescence intensity of lymphocytes, the difference between the mean value and the median value of the fluorescence intensity of lymphocytes, the skewness of the fluorescence intensity of lymphocytes, or the combination of the kurtosis and the dispersion of the fluorescence intensity of lymphocytes is stored in advance, the mean value, the difference between the mean value and the median value, the skewness, or the combination of the kurtosis and the dispersion of the fluorescence intensity of lymphocytes is obtained, and the T-lymphocyte ratio is obtained by reference to the aforementioned data. In this case, by determining whether the T-lymphocyte ratio is in a normal range or not, an abnormal ratio of B-lymphocytes to T-lymphocytes can be detected. Also, it is possible that the T-lymphocyte ratio is displayed as an analysis result.

Although Embodiments 2 to 5 described above have addressed a configuration in which a B-lymphocyte ratio that corresponds to the mean value of the fluorescence intensity of lymphocytes, to the difference between the mean value and the median value of the fluorescence intensity of lymphocytes, to the skewness of the fluorescence intensity of lymphocytes, and to the combination of the kurtosis and the dispersion of the fluorescence intensity of lymphocytes is obtained, the present invention is not limited thereto. A configuration may be adopted in which the ratio of B-lymphocytes to T-lymphocytes is obtained using statistical data of the fluorescence intensity of lymphocytes other than the aforementioned statistical data. Since the measures of central tendency of the statistical data each correspond to the ratio of B-lymphocytes to T-lymphocytes, a configuration in which the ratio of B-lymphocytes to T-lymphocytes is obtained using either the median value or the root-mean-square (RMS) may be adopted. In more detail, a configuration may be adopted in which the median value or the RMS of the fluorescence intensity of lymphocytes is obtained, and in reference to data that show the correspondence relationship between B-lymphocyte ratio and median value or RMS, a B-lymphocyte ratio that corresponds to the obtained median value or the RMS is obtained.

The dispersion included in the statistical data is monotonically changed relative to the ratio of B-lymphocytes to T-lymphocytes over a specific range, and mostly has a constant value relative to the ratio of B-lymphocytes to T-lymphocytes in other ranges. Described more specifically, the dispersion and the standard deviation are monotonically increased mostly linearly when the B-lymphocyte ratio is in the range of 0 to 40%, and each mostly has a constant value when the B-lymphocyte ratio is in the range of 40 to 100% (see FIGS. 25F and 25G). Also, the dispersion and the standard deviation exhibit a large rate of change (inclination) when the B-lymphocyte ratio is in the range of 0 to 40%, and in this range, a B-lymphocyte ratio that corresponds to the dispersion or the standard deviation can be highly precisely identified. Generally, a normal range of the B-lymphocyte ratio is said to be 5 to 20%. Therefore, when only determining the presence or absence of an abnormal ratio of B-lymphocytes to T-lymphocytes, the dispersion or the standard deviation can be used singly.

Figure 25A:
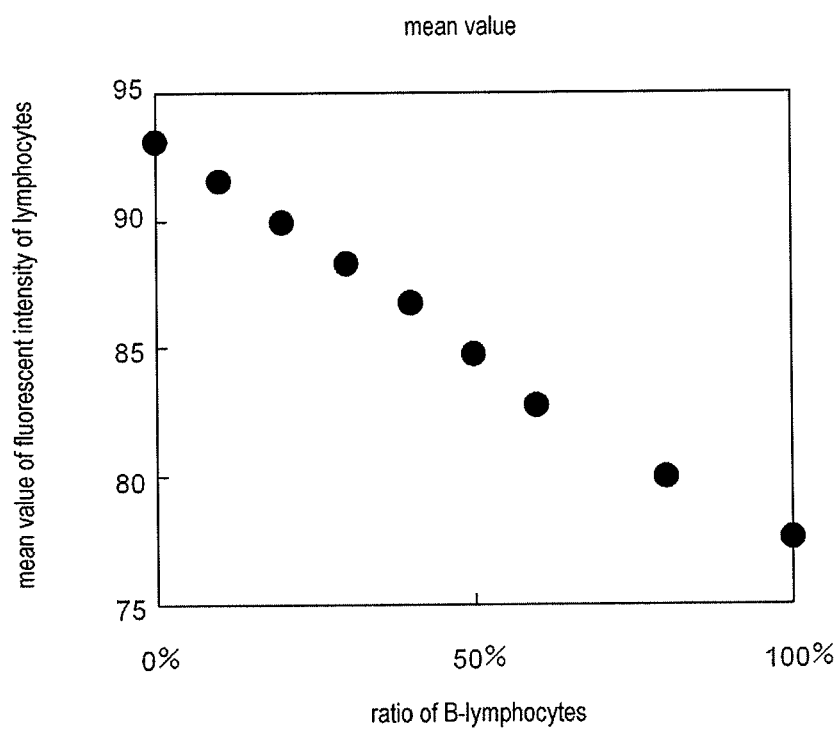
FIG. 25A is a graph showing the mean value of the fluorescence intensity of lymphocytes at the respective T/B-lymphocyte ratios.
Figure 25B:
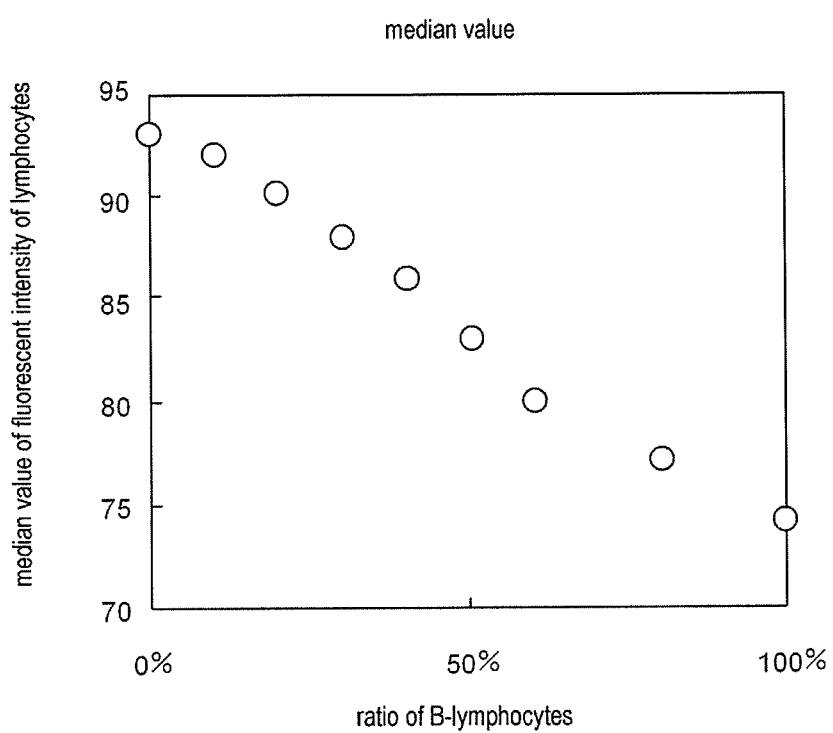
FIG. 25B is a graph showing the median value of the fluorescence intensity of lymphocytes at the respective T/B-lymphocyte ratios.
Figure 25C:
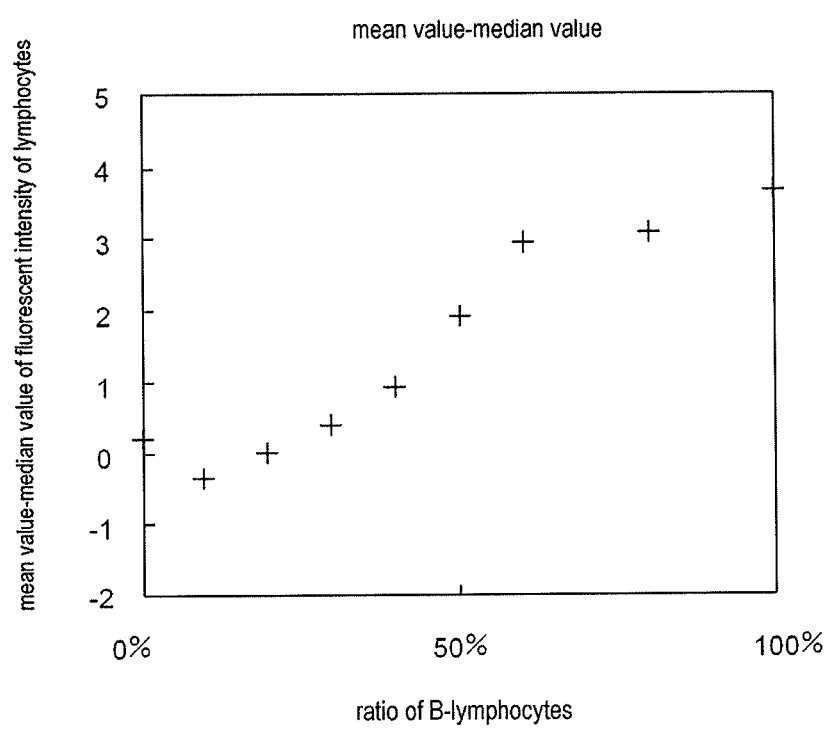
FIG. 25C is a graph showing the mean-median value of the fluorescence intensity of lymphocytes at the respective T/B-lymphocyte ratios.
Figure 25D:
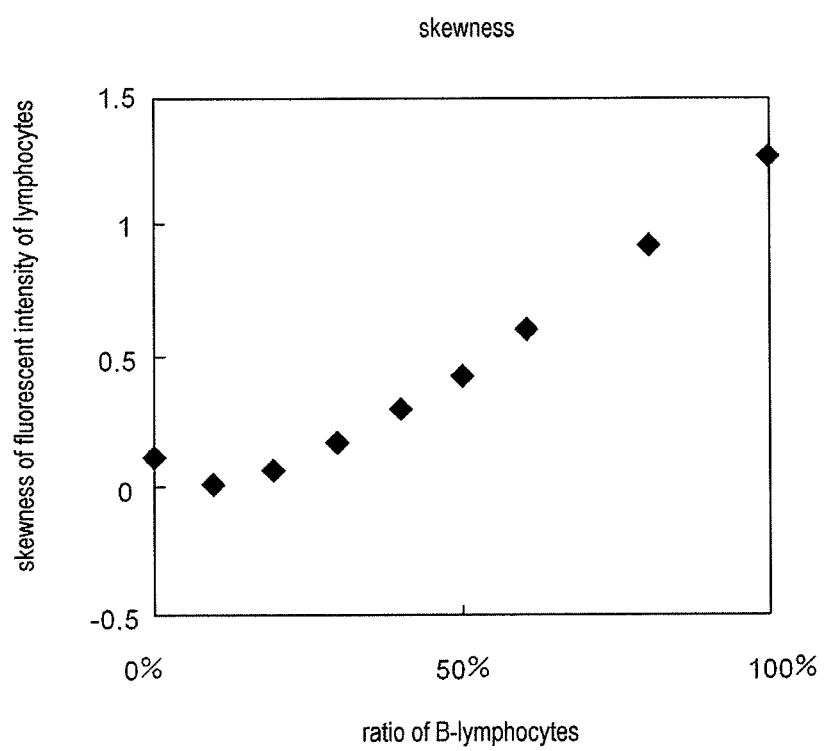
FIG. 25D is a graph showing the skewness of the fluorescence intensity of lymphocytes at the respective T/B-lymphocyte ratios.
Figure 25E:
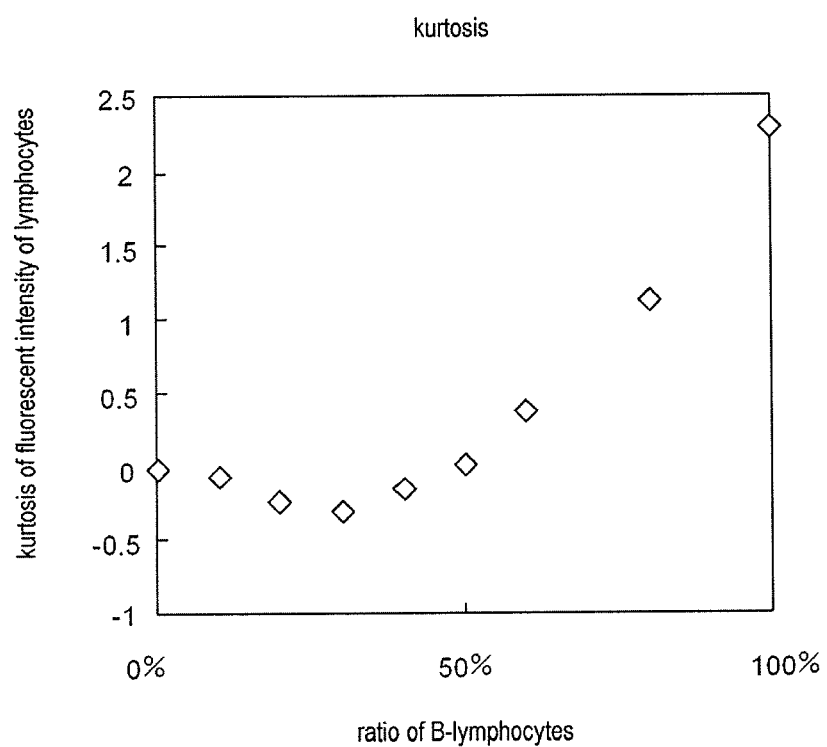
FIG. 25E is a graph showing the kurtosis values of the fluorescence intensity of lymphocytes at the respective T/B-lymphocyte ratios.
Figure 25F:
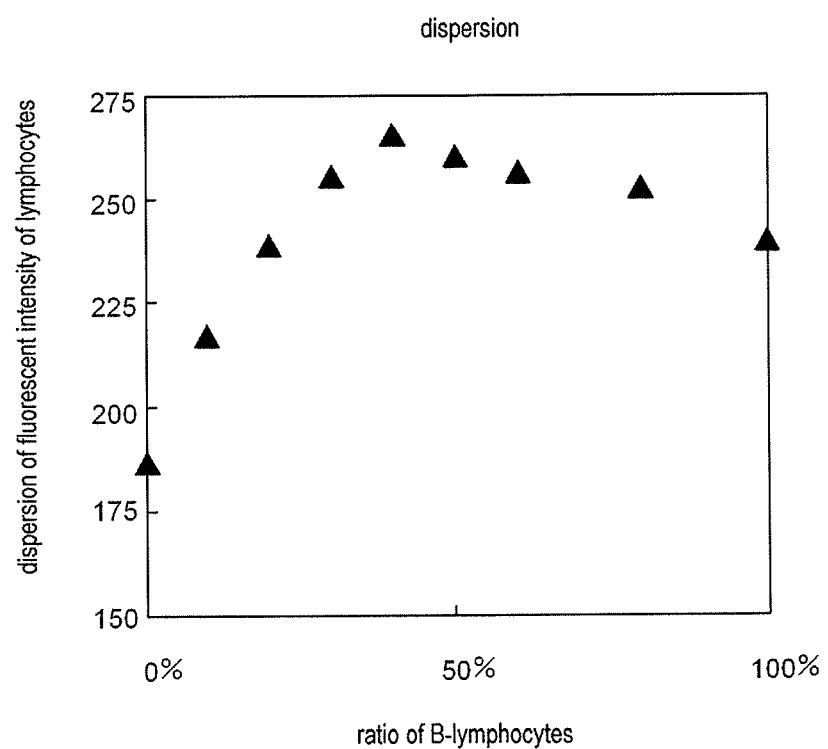
FIG. 25F is a graph showing the dispersion of the fluorescence intensity of lymphocytes at the respective T/B-lymphocyte ratios.
Figure 25G:
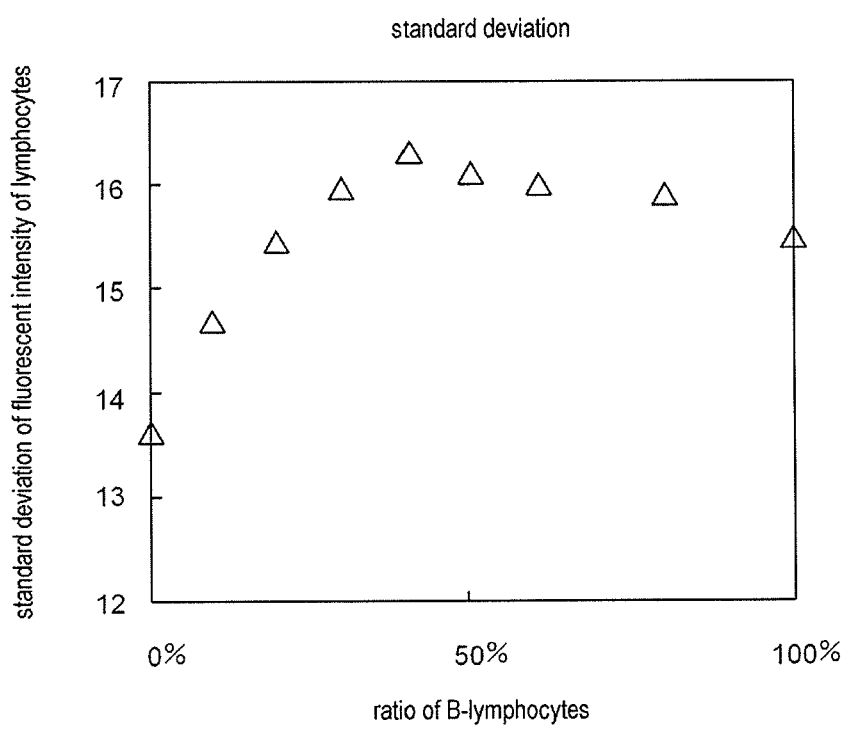
FIG. 25G is a graph showing the standard deviation of the fluorescence intensity of lymphocytes at the respective T/B-lymphocyte ratios.
Figure 25H:
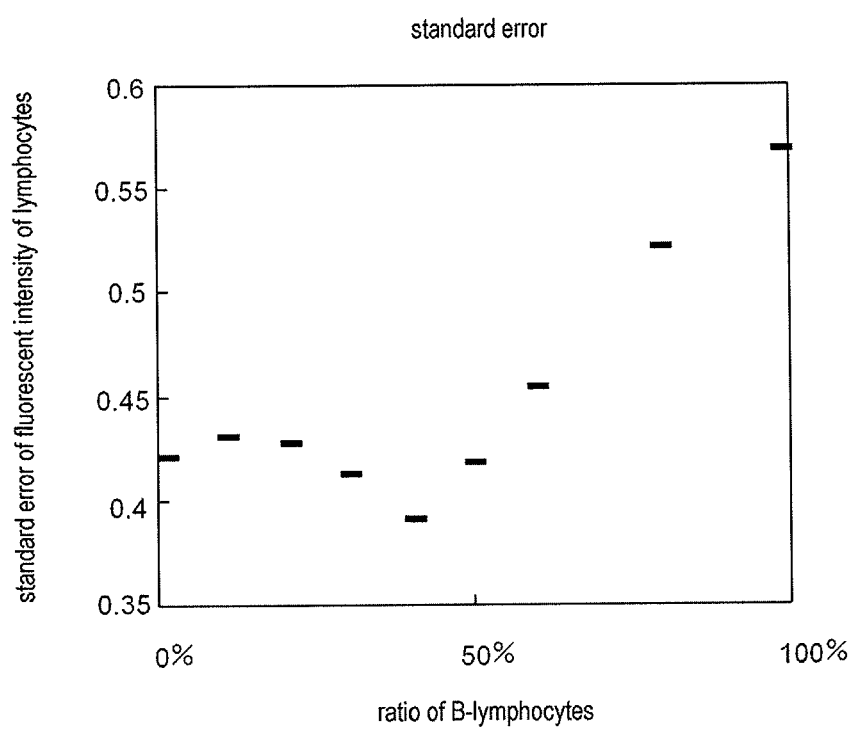
FIG. 25H is a graph showing the standard error of the fluorescence intensity of lymphocytes at the respective T/B-lymphocyte ratios.

On the other hand, the standard error mostly has a constant value when the B-lymphocyte ratio is in the range of 0 to 40%, and is monotonically increased mostly linearly when the B-lymphocyte ratio is in the range of 0 to 40% (see FIG. 25H). The standard error exhibits a large rate of change (inclination) when the B-lymphocyte ratio is in the range of 40 to 100%, and in this range, a B-lymphocyte ratio that corresponds to the standard error can be highly precisely identified. Therefore, combining the standard error and the dispersion or standard deviation enables the B-lymphocyte ratio to be obtained highly precisely. More specifically, it is possible to adopt a configuration in which in the case where the B-lymphocyte ratio identified by the dispersion or the standard deviation has a value of 0 to 40%, this B-lymphocyte ratio is adopted, and in the case where the B-lymphocyte ratio identified by the dispersion or the standard deviation has a value of 40 to 100%, the B-lymphocyte ratio identified by the standard error is adopted. Likewise, it is possible to use the relationship between the dispersion or the standard deviation of the fluorescence intensity of lymphocytes and the T-lymphocyte ratio as well as the relationship between the standard error of the fluorescence intensity of lymphocytes and the T-lymphocyte ratio.

As described in Embodiment 5, the kurtosis of the fluorescence intensity of lymphocytes is changed mostly linearly in the region where the B-lymphocyte ratio is 30% or greater. Therefore, it is also possible to adopt a configuration in which the B-lymphocyte ratio is identified by combining the kurtosis and the standard deviation of the fluorescence intensity of lymphocytes.

Although Embodiments 2 to 5 have addressed a configuration in which an analysis result screen containing a B-lymphocyte ratio is displayed, the present invention is not limited thereto. It is possible that at least one of the T-lymphocyte ratio, B-lymphocyte count, and T-lymphocyte count is displayed in place of the B-lymphocyte ratio or displayed together with the B-lymphocyte ratio. Since the total B-lymphocyte and T-lymphocyte count can closely resemble the lymphocyte count, the B-lymphocyte count can be obtained by multiplying the lymphocyte count by the B-lymphocyte ratio. Also, the T-lymphocyte count can be obtained by multiplying the lymphocyte count by the T-lymphocyte ratio.

Although Embodiments 2 to 5 described above have addressed a configuration in which a B-lymphocyte ratio $R_B$ is obtained, and whether the B-lymphocyte ratio $R_B$ is in a predetermined normal range or not is determined in order to find out the presence or absence of an abnormal ratio of B-lymphocytes to T-lymphocytes, the present invention is not limited thereto. It is also possible that whether an indicator representing the particle size distribution of the fluorescence intensity of lymphocytes used to obtain the B-lymphocyte ratio $R_B$ is in a predetermined range or not is determined in order to find out the presence or absence of an abnormal ratio of B-lymphocytes to T-lymphocytes. That is, it is also possible that at least one value selected from a measure of central tendency, a dispersion value, and a value that indicates a distribution bias of the fluorescence intensity of lymphocytes is compared with a threshold value to determine whether the presence or absence of an abnormal ratio of B-lymphocytes to T-lymphocytes. For example, in the case of Embodiment 2, the mean value of the fluorescence intensity of lymphocytes with a threshold value is compared to determine the presence or absence an abnormal ratio of B-lymphocytes to T-lymphocytes.

The present invention shall be described in detail below by way of examples, but the present invention is not limited thereto.

EXAMPLES

Example 1

(Preparation of Measurement Sample)

Blood (50 mL) was collected from a healthy subject using a blood collecting tube containing EDTA-2K for use in hematological tests. 50 mL of the collected blood was centrifuged at 600 rpm for 15 minutes to remove supernatant (platelet concentrate layer). The blood after platelet concentrate removal was diluted with phosphate buffered saline so as to attain the total volume of 100 mL. Layers of lymphocyte separation solutions (d=1.119, d=1.077) manufactured by Nacalai Tesque, Inc., were formed according to the instruction manual, and then the diluted blood was added so as to form a layer. The sample having layers of lymphocyte separation solutions and diluted blood was subjected to specific gravity centrifugation (at 1900 rpm for 15 minutes) to collect a fraction (60 mL) containing lymphocytes and monocytes.

60 mL of the collected fraction (monocyte layer) containing lymphocytes and monocytes was divided into 10 mL portions, 40 mL of phosphate buffered saline was added to each portion, and the mixtures were centrifuged at 1900 rpm for 15 minutes to remove supernatant, thereby washing the monocyte layer. This washing was carried out twice.

Using the washed monocyte layer, magnetic cell sorting was carried out with a Human B cell Enrichment Kit and a Human T cell Enrichment Kit manufactured by StemCell Technologies according to the instruction manual. This magnetic cell sorting yielded 0.5 mL of a sample containing a large amount of B-lymphocytes (B-lymphocyte sample) and 0.5 mL of a sample containing a large amount of T-lymphocytes (T-lymphocyte sample).

5 µl of an FITC-labeled anti-CD19 antibody (manufactured by Dako) was added to 50 µl of the B-lymphocyte sample. Also, 5 µl of an FITC-labeled anti-CD3 antibody (manufactured by Dako) was added to 50 µl of the T-lymphocyte sample.

The labeled antibody-added B-lymphocyte sample (9 µl), Stromatolyser 4DL (442 µl), and Stromatolyser 4DS (9 µl) were mixed and incubated at room temperature for 2 minutes to prepare a B-lymphocyte measurement sample. Similarly, the labeled antibody-added T-lymphocyte sample (9 µl), Stromatolyser 4DL (442 µl), and Stromatolyser 4DS (9 µl) were mixed and incubated at room temperature for 2 minutes to prepare a T-lymphocyte measurement sample.

(Analysis of Measurement Samples by Flow Cytometry)

The B-lymphocyte measurement sample and the T-lymphocyte measurement sample obtained in the above-described measurement sample preparation were both analyzed by flow cytometry using a FACS Calibur (manufacture by BD) with the number of cell takeup being set to 2000.

Figure 19:
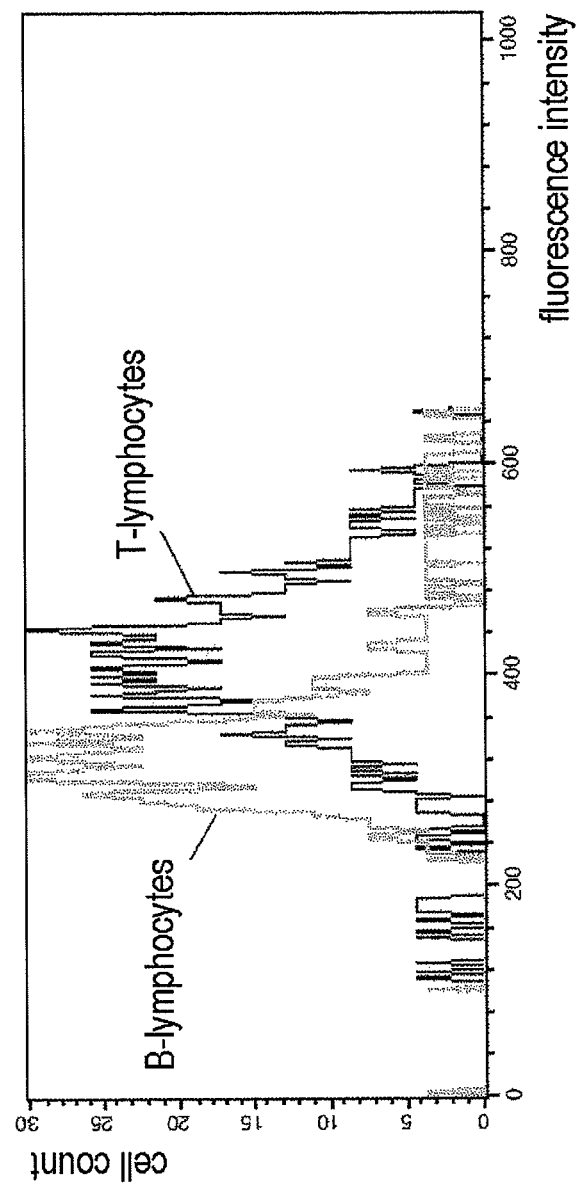
FIG. 19 is a histogram representing cell count and fluorescence intensity obtained from a flow cytometry analysis using a B-lymphocyte measurement sample and a T-lymphocyte measurement sample.
Figure 20:
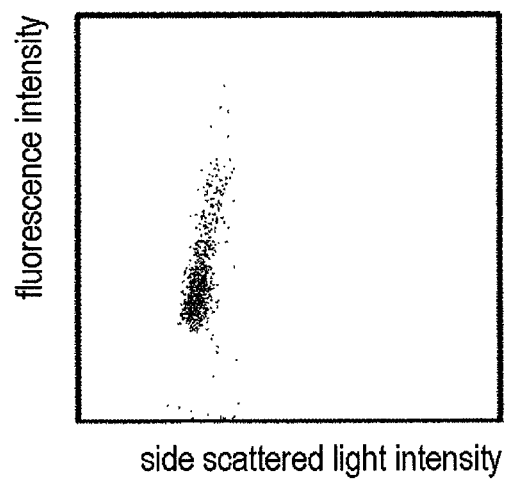
FIG. 20 is a scattergram representing side scattered light intensity and fluorescence intensity obtained from a flow cytometry analysis using a B-lymphocyte measurement sample.
Figure 21:
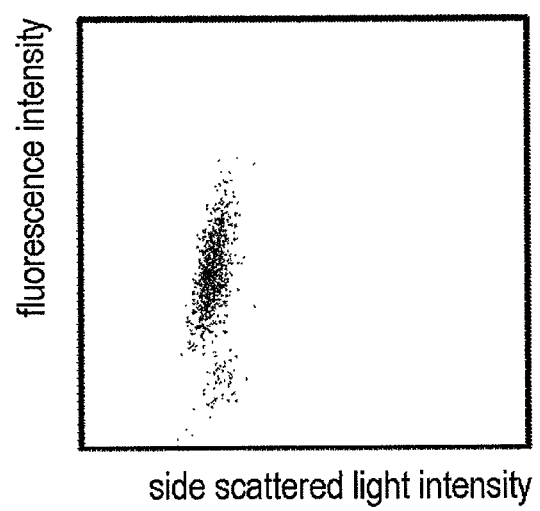
FIG. 21 is a scattergram representing side scattered light intensity and fluorescence intensity obtained from a flow cytometry analysis using a T-lymphocyte measurement sample.

FIG. 19 is a particle size distribution chart representing a cell count and fluorescence intensity obtained from the flow cytometry analysis using the B-lymphocyte measurement sample and the T-lymphocyte measurement sample. FIG. 20 is a scattergram representing side scattered light intensity and fluorescence intensity obtained from the flow cytometry analysis using the B-lymphocyte measurement sample. FIG. 21 is a scattergram representing side scattered light intensity and fluorescence intensity obtained from the flow cytometry analysis using the T-lymphocyte measurement sample. From FIGS. 19, 20, and 21, it is clear that B-lymphocytes are distributed on the lower fluorescence intensity side than T-lymphocytes are, and in contrast, T-lymphocytes are distributed on the higher fluorescence intensity side than B-lymphocytes are. This suggests that B-lymphocytes and T-lymphocytes can be detected based on the difference in fluorescence intensity.

(Analysis with Electron Microscopes)

The morphological change of B-lymphocytes and T-lymphocytes treated with a hemolyzing agent and a fluorescent dye that stains nucleic acid was analyzed using electron microscopes. B-lymphocytes treated with a hemolyzing agent and a fluorescent dye that stains nucleic acid were prepared by mixing a B-lymphocyte sample (9 µl) as obtained in Example 1, Stromatolyser 4DL (442 µl), and Stromatolyser 4DS (9 µl) and incubating the mixture at 35° C. for 22 seconds. Similarly, T-lymphocytes treated with a hemolyzing agent and a fluorescent dye that stains nucleic acid were prepared by mixing a T-lymphocyte sample (9 µl) as obtained in Example 1, Stromatolyser 4DL (442 µl), and Stromatolyser 4DS (9 µl) and incubating the mixture at 35° C. for 22 seconds.

B-lymphocytes contained in the B-lymphocyte sample treated with a hemolyzing agent and a fluorescent dye that stains nucleic acid were fixed by 1.5% glutaraldehyde, and analyzed using a scanning electron microscope (JEOL JSM-7500 TFEA) and a transmission electron microscope (Hitachi H-7500) according to an electron microscopic specimen preparation method (Mari Kono et al. (2009), "Morphological definition of CD71 positive reticulocytes by various staining techniques and electron microscopy compared to reticulocytes detected by an automated hematology analyzer", Clinica Chimica Acta, Vol. 404, p 105-110). T-lymphocytes contained in the T-lymphocyte sample treated with a hemolyzing agent and a fluorescent dye that stains nucleic acid were analyzed in the same manner using the scanning electron microscope and the transmission electron microscope.

As a control, B-lymphocytes and T-lymphocytes contained in the B-lymphocyte sample and the T-lymphocyte sample, respectively, before treatment with a hemolyzing agent and a fluorescent dye that stains nucleic acid were analyzed in the same manner using the electron microscopes.

Figure 22:
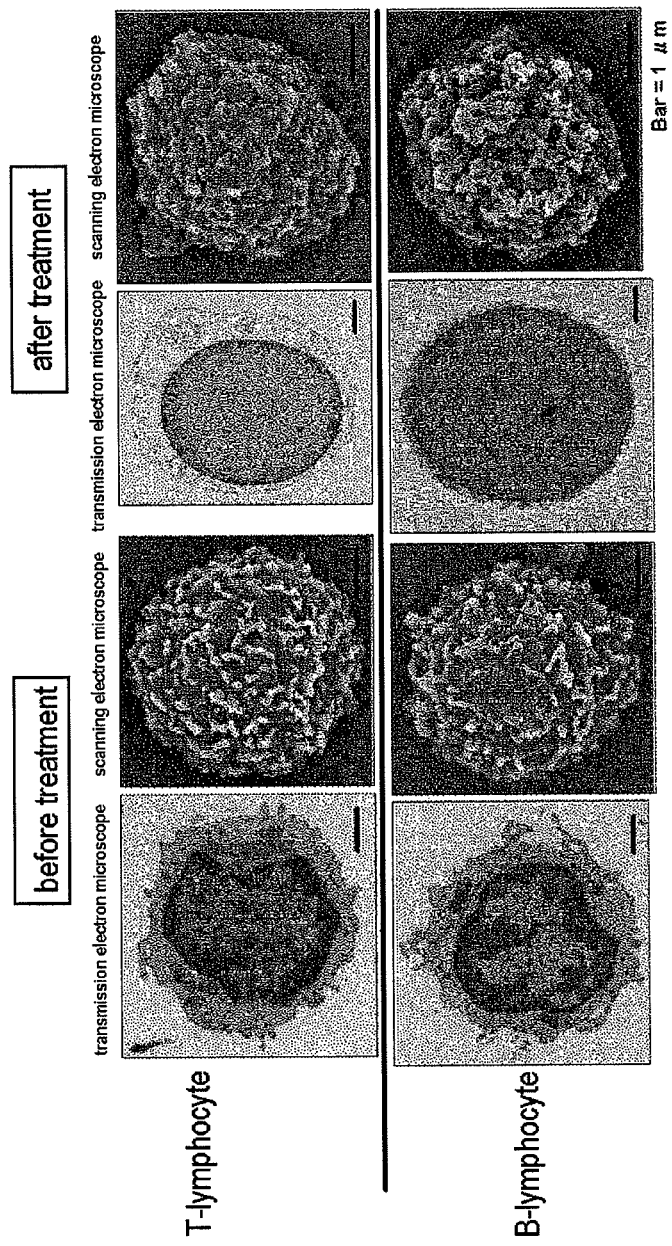
FIG. 22 shows micrographs showing results of an electron microscopic analysis.
Figure 23A:
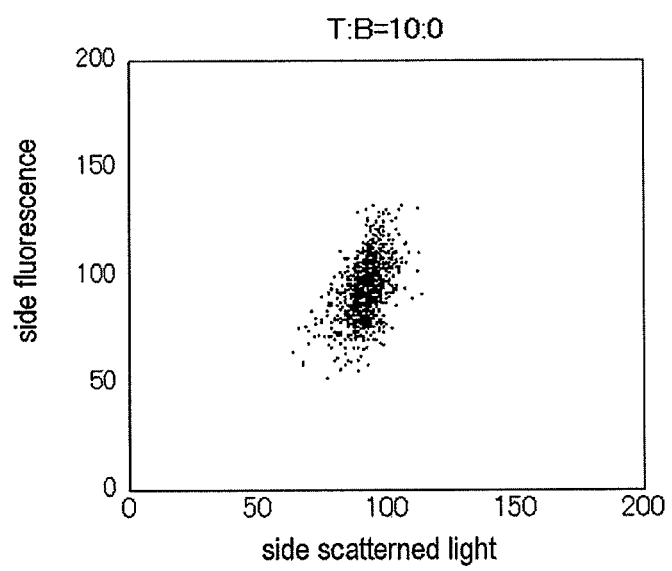
FIG. 23A is a scattergram representing fluorescence intensity and side scattered light information showing a lymphocyte particle size distribution when the T/B-lymphocyte ratio is 10:0.
Figure 23B:
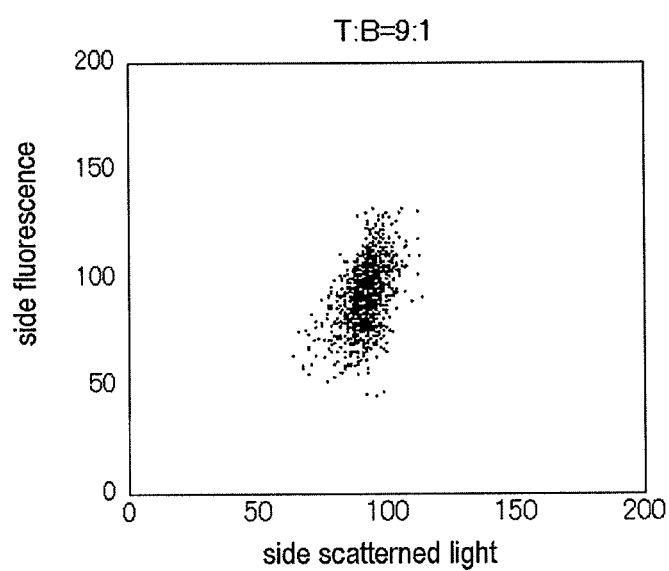
FIG. 23B is a scattergram representing fluorescence intensity and side scattered light information showing a lymphocyte particle size distribution when the T/B-lymphocyte ratio is 9:1.
Figure 23C:
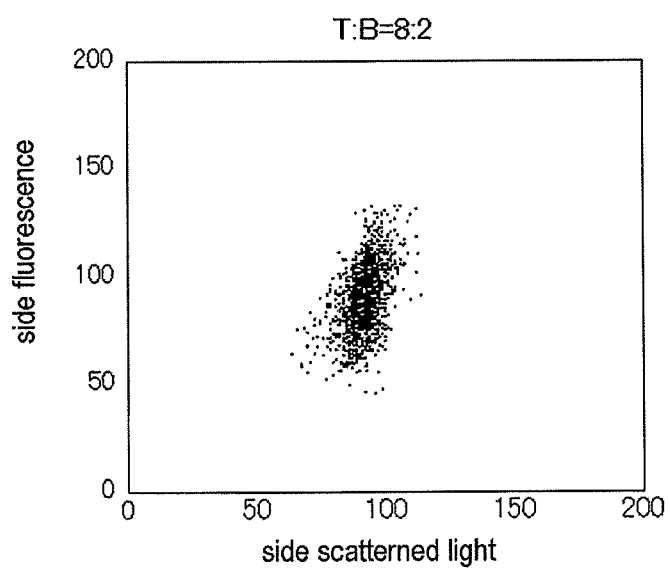
FIG. 23C is a scattergram representing fluorescence intensity and side scattered light information showing a lymphocyte particle size distribution when the T/B-lymphocyte ratio is 8:2.
Figure 23D:
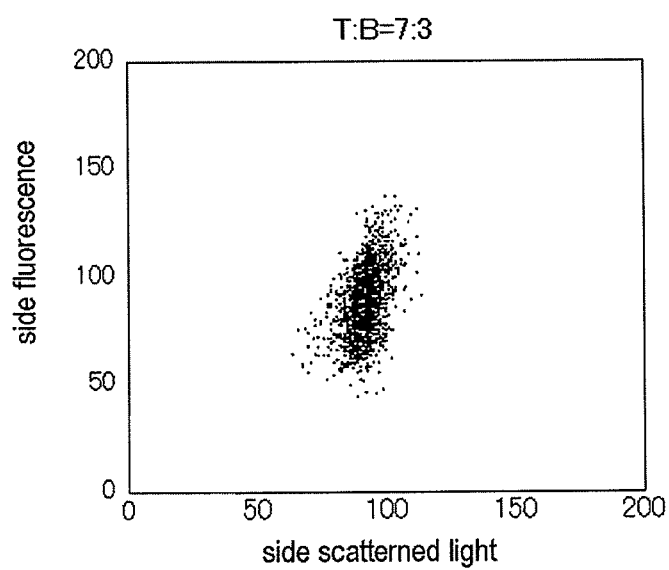
FIG. 23D is a scattergram representing fluorescence intensity and side scattered light information showing a lymphocyte particle size distribution when the T/B-lymphocyte ratio is 7:3.
Figure 23E:
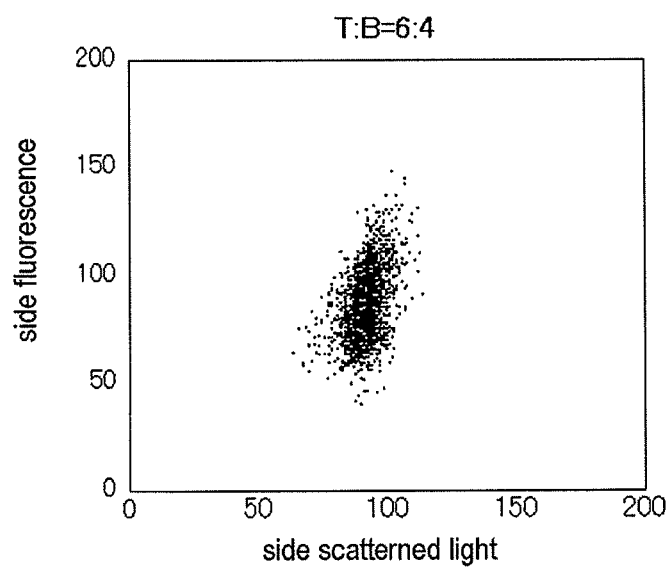
FIG. 23E is a scattergram representing fluorescence intensity and side scattered light information showing a lymphocyte particle size distribution when the T/B-lymphocyte ratio is 6:4.
Figure 23F:
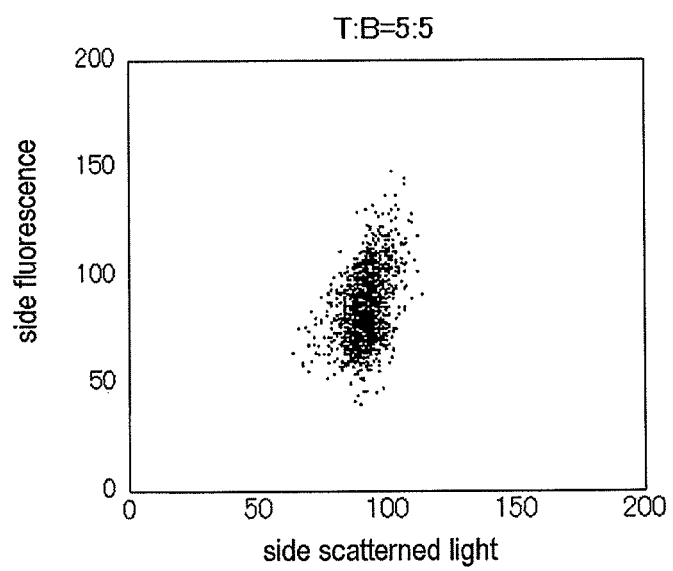
FIG. 23F is a scattergram representing fluorescence intensity and side scattered light information showing a lymphocyte particle size distribution when the T/B-lymphocyte ratio is 5:5.
Figure 23G:
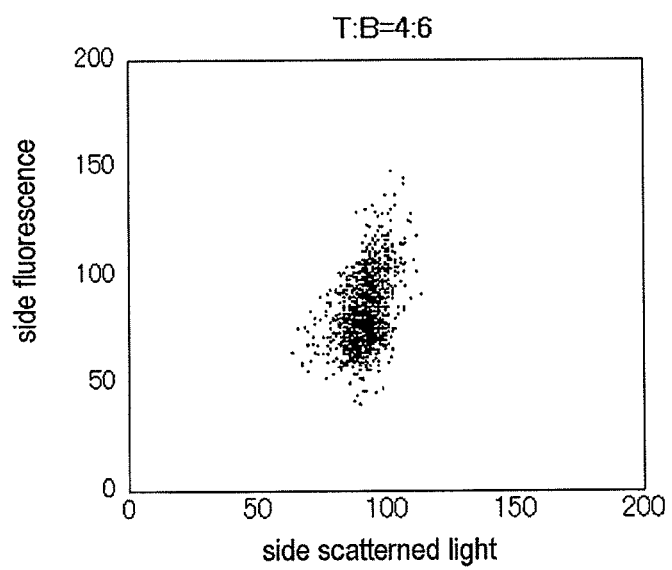
FIG. 23G is a scattergram representing fluorescence intensity and side scattered light information showing a lymphocyte particle size distribution when the T/B-lymphocyte ratio is 4:6.
Figure 23H:
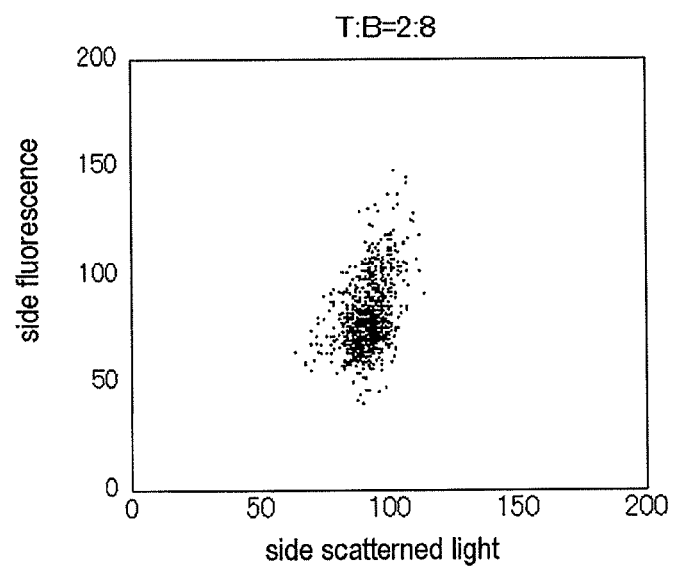
FIG. 23H is a scattergram representing fluorescence intensity and side scattered light information showing a lymphocyte particle size distribution when the T/B-lymphocyte ratio is 2:8.
Figure 23I:
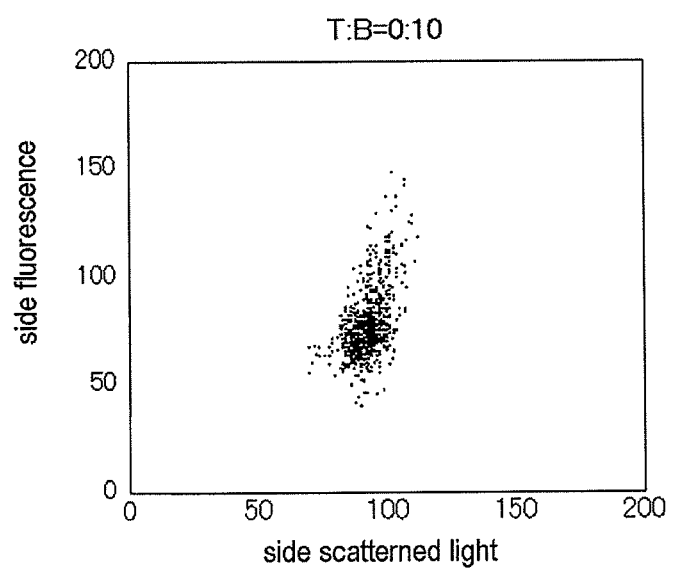
FIG. 23I is a scattergram representing fluorescence intensity and side scattered light information showing a lymphocyte particle size distribution when the T/B-lymphocyte ratio is 0:10.
Figure 24A:
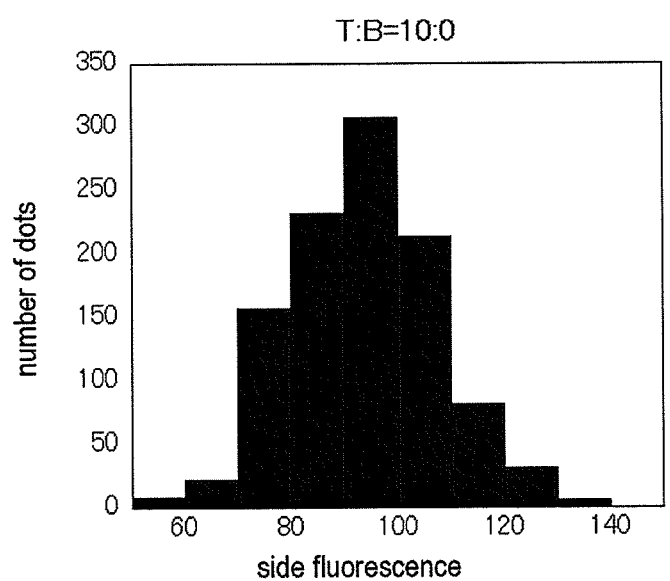
FIG. 24A is a particle size distribution chart of fluorescence intensity showing a lymphocyte distribution when the T/B-lymphocyte ratio is 10:0.
Figure 24B:
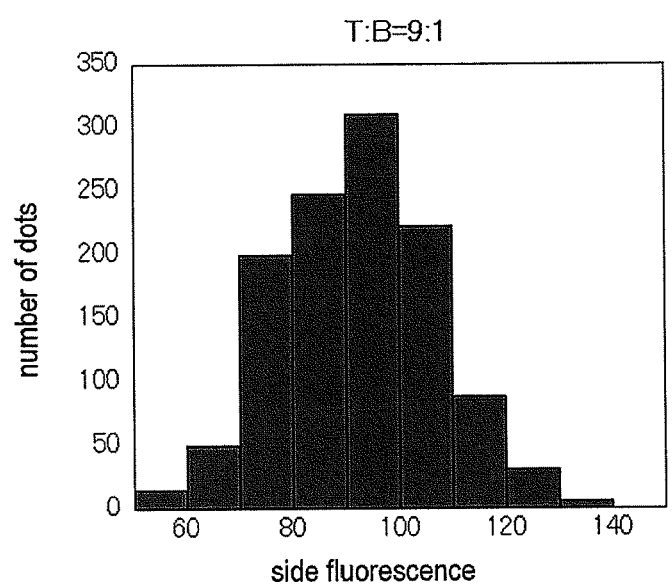
FIG. 24B is a particle size distribution chart of fluorescence intensity showing a lymphocyte distribution when the T/B-lymphocyte ratio is 9:1.
Figure 24C:
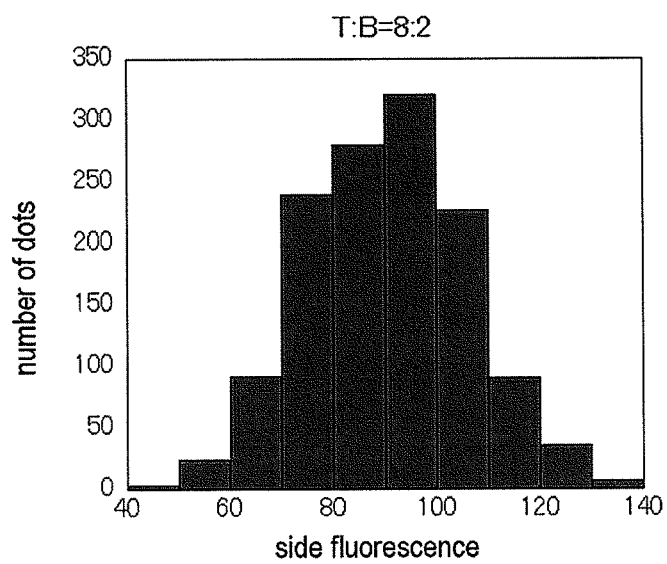
FIG. 24C is a particle size distribution chart of fluorescence intensity showing a lymphocyte distribution when the T/B-lymphocyte ratio is 8:2.
Figure 24D:
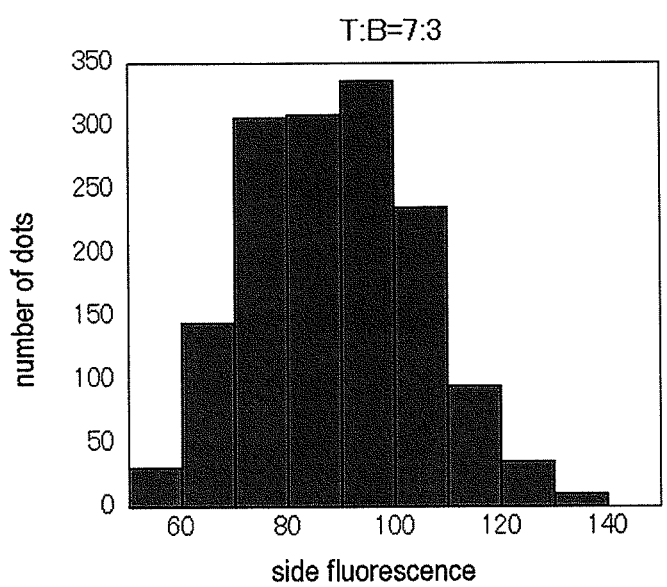
FIG. 24D is a particle size distribution chart of fluorescence intensity showing a lymphocyte distribution when the T/B-lymphocyte ratio is 7:3.
Figure 24E:
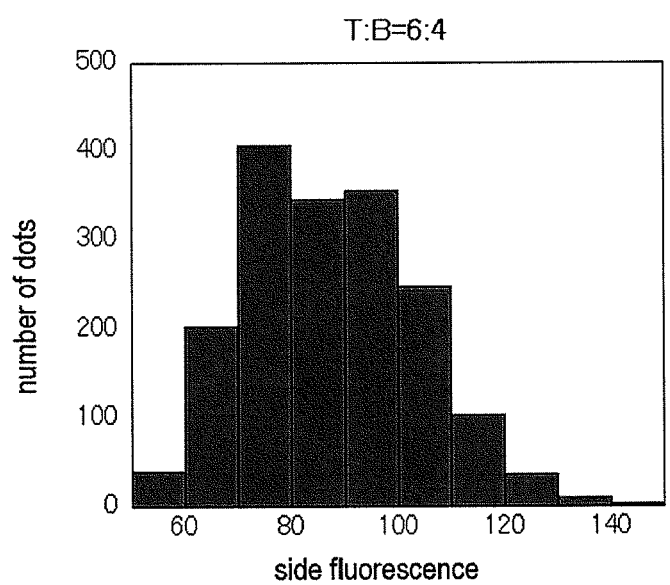
FIG. 24E is a particle size distribution chart of fluorescence intensity showing a lymphocyte distribution when the T/B-lymphocyte ratio is 6:4.
Figure 24F:
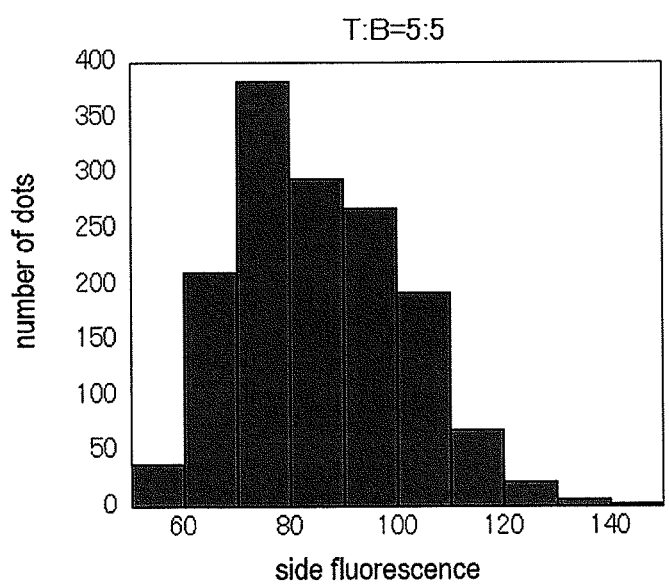
FIG. 24F is a particle size distribution chart of fluorescence intensity showing a lymphocyte distribution when the T/B-lymphocyte ratio is 5:5.
Figure 24G:
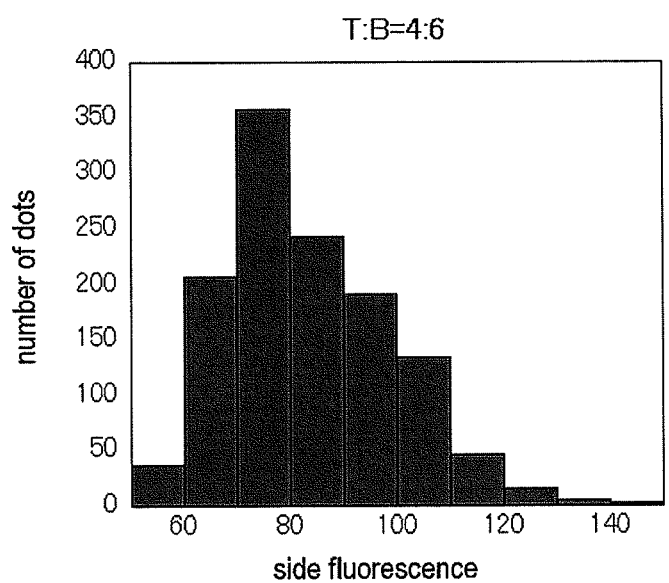
FIG. 24G is a particle size distribution chart of fluorescence intensity showing a lymphocyte distribution when the T/B-lymphocyte ratio is 4:6.
Figure 24H:
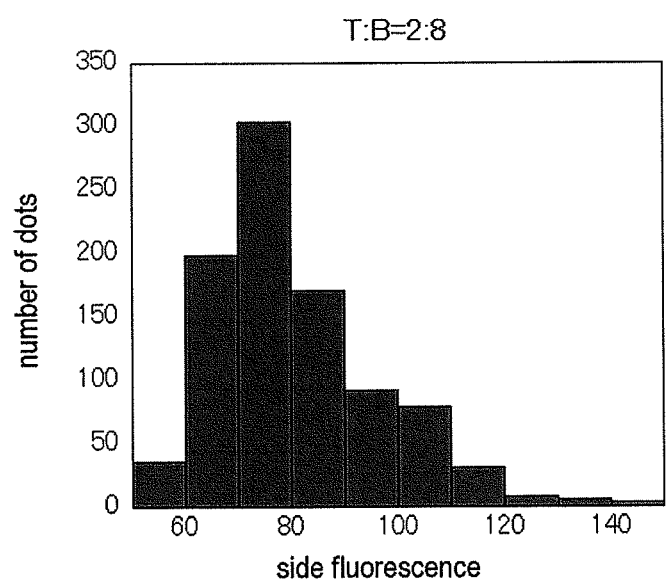
FIG. 24H is a particle size distribution chart of fluorescence intensity showing a lymphocyte distribution when the T/B-lymphocyte ratio is 2:8.
Figure 24I:
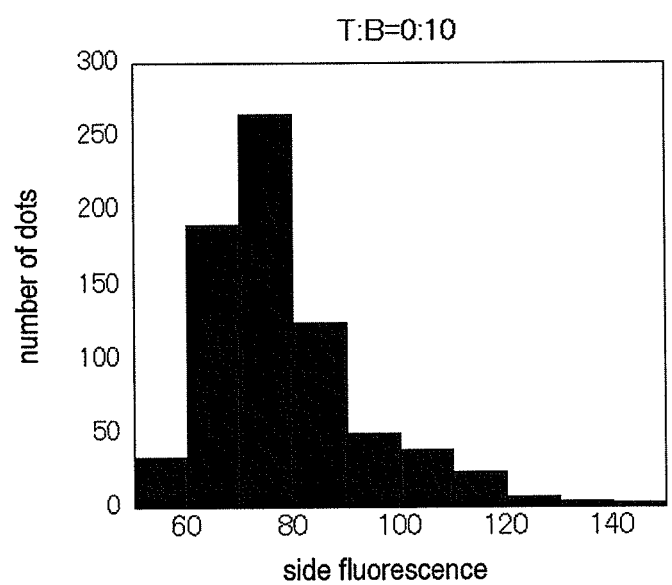
FIG. 24I is a particle size distribution chart of fluorescence intensity showing a lymphocyte distribution when the T/B-lymphocyte ratio is 0:10.

Results of the electron microscopic analysis are presented in FIG. 22. As shown in FIG. 22, a comparison of B-lymphocytes and T-lymphocytes after the treatment with Stromatolyser 4DL and Stromatolyser 4DS revealed that the amount of cytoplasm is more reduced in B-lymphocytes than in T-lymphocytes. Moreover, it was revealed that B-lymphocytes have more surface irregularities than T-lymphocytes do. This suggests that the morphological change of B-lymphocytes and T-lymphocytes caused by the treatment with a hemolyzing agent and a fluorescent dye that stains nucleic acid creates a difference in fluorescence intensity between B-lymphocytes and T-lymphocytes.

Example 2

<Preparation of B-Lymphocyte Sample and T-Lymphocyte Sample>

The present inventors prepared a B-lymphocyte sample and a T-lymphocyte sample according to the following procedure. First, 50 mL of blood was collected from a healthy subject using a blood collecting tube containing EDTA-2K for use in hematological tests. 49 mL of the collected blood was centrifuged at 600 rpm for 15 minutes to remove supernatant (platelet concentrate layer). The blood after platelet concentrate removal was diluted with phosphate buffered saline so as to attain the total volume of 98 mL. Layers of lymphocyte separation solutions (d=1.119, d=1.077) manufactured by Nacalai Tesque, Inc., were formed according to the instruction manual, and then the diluted blood was added so as to form a layer. The sample having layers of lymphocyte separation solutions and diluted blood was subjected to specific gravity centrifugation (at 1900 rpm for 15 minutes) to collect a fraction containing lymphocytes and monocytes.

Phosphate buffered saline (PBS) was added to the collected fraction (monocyte layer) containing lymphocytes and monocytes, and the mixture was centrifuged at 1900 rpm for 15 minutes to remove supernatant, thereby washing the monocyte layer. This washing was carried out twice.

Using the washed monocyte layer sample, magnetic cell sorting was carried out with a Human B cell Enrichment Kit and a Human T cell Enrichment Kit manufactured by StemCell Technologies according to the instruction manual. This magnetic cell sorting yielded 0.5 mL of a sample containing a large amount of B-lymphocytes (B-lymphocyte sample) and 0.5 mL of a sample containing a large amount of T-lymphocytes (T-lymphocyte sample).

<Investigation of State of Separation of B-Lymphocyte Sample and T-Lymphocyte Sample>

Two 50 μL B-lymphocyte samples were provided, and 1 μL of an FITC-labeled anti-CD19 antibody (manufactured by Dako) was added to one sample, and 1 μL of an FITC-labeled mouse IgG (manufactured by Dako) was added as a control to the other sample.

Also, two 50 μL T-lymphocyte samples were provided, and 1 μL of an FITC-labeled anti-CD3 antibody (manufactured by Dako) was added to one sample, and 1 μL of an FITC-labeled mouse IgG (manufactured by Dako) was added as a control to the other sample.

B-lymphocytes and T-lymphocytes were measured by analyzing the prepared samples using a flow cytometer (FACS Calibur (manufacture by BD)) with the number of cell takeup being set to 2000 to check the state of separation of B-lymphocytes and T-lymphocytes. Results showed that the B-lymphocyte samples had a B-lymphocyte purity of 86.7%, and the T-lymphocyte samples had a T-lymphocyte purity of 97.3%.

<Analysis of Measurement Samples>

The prepared B-lymphocyte samples and T-lymphocyte samples were subjected to measurement using an automatic hematology analyzer XE-2100 (manufactured by Sysmex Corporation) to classify leucocytes into four types. Stromatolyser 4DL and Stromatolyser 4DS (both manufactured by Sysmex Corporation) were used as measurement reagents.

(Data Acquisition at T/B-Lymphocyte Ratios of 10:0 and 0:10)

Next, information regarding fluorescence intensity and side scattered light obtained from the measurement was analyzed using a KaleidaGraph (manufactured by Hulinks Inc.). First, from information regarding fluorescence intensity and side scattered light obtained from the T-lymphocyte sample measurement, a scattergram of the T-lymphocyte samples was created. Similarly, from information regarding fluorescence intensity and side scattered light obtained from the B-lymphocyte sample measurement, a scattergram of the B-lymphocyte samples was created. Next, using the scattergram of the T-lymphocyte samples, dots appeared in the lymphocyte region were counted as T-lymphocytes, and the number of T-lymphocytes contained in the T-lymphocyte samples was obtained (1057). Similarly, using the scattergram of the B-lymphocyte samples, dots appeared in the lymphocyte region were counted as B-lymphocytes, and the number of B-lymphocytes contained in the B-lymphocyte samples was obtained (749). From the dots counted as T-lymphocytes and the information regarding their fluorescent intensity, a particle size distribution chart of the fluorescent intensity of T-lymphocytes was created. Similarly, from the dots counted as B-lymphocytes and the information regarding their fluorescent intensity, a particle size distribution chart of the fluorescent intensity of B-lymphocytes was created. Moreover, the mean value, the median value, the skewness, the kurtosis, the dispersion, the standard deviation, the standard error, the root-mean-square (RMS), and the mean-median value (value obtained by subtracting the median value from the mean value) of each of the particle size distribution charts of the fluorescent intensity of T-lymphocytes and B-lymphocytes were calculated. Here, the scattergram, the particle size distribution chart of fluorescence intensity, and the calculated values (mean value, median value, skewness, kurtosis, dispersion, standard deviation, standard error, root-mean-square (RMS), and mean-median value) obtained from the T-lymphocyte sample measurement were regarded as 10:0 T-lymphocyte to B-lymphocyte ratio (hereinafter referred to as a "T/B-lymphocyte ratio") data. The scattergram, the particle size distribution chart of fluorescence intensity, and the calculated values obtained from the B-lymphocyte sample measurement were regarded as 0:10 T/B-lymphocyte ratio data.

(Data Acquisition at T/B-Lymphocyte Ratios of 9:1, 8:2, 7:3, 6:4, 5:5, 4:6, and 2:8)

Next, data (scattergram, fluorescence intensity-based particle size distribution chart, and calculated values) at T/B-lymphocyte ratios of 9:1, 8:2, 7:3, 6:4, 5:5, 4:6, and 2:8 were acquired as follows.

Data Acquisition at T/B-Lymphocyte Ratio of 9:1

From each of the aforementioned 1057 dots counted as T-lymphocytes, the fluorescence intensity and the side scattered light information of each dot was extracted as T-lymphocyte information. Also, from each of the 118 dots randomly selected from the 749 dots counted as B-lymphocytes, the fluorescence intensity and the side scattered light information of each dot was extracted as B-lymphocyte information. Then, based on the information regarding the total 1175 dots, i.e., 1057 T-lymphocytes and 118 B-lymphocytes, data at a T/B-lymphocyte ratio of 9:1 was acquired.

Data Acquisition at T/B-Lymphocyte Ratio of 8:2

From each of the aforementioned 1057 dots counted as T-lymphocytes, the fluorescence intensity and the side scattered light information of each dot was extracted as T-lymphocyte information. Also, from each of the 265 dots randomly selected from the 749 dots counted as B-lymphocytes, the fluorescence intensity and the side scattered light information of each dot was extracted as B-lymphocyte information. Then, based on the information regarding the total 1322 dots, i.e., 1057 T-lymphocytes and 265 B-lymphocytes, data at a T/B-lymphocyte ratio of 8:2 was acquired.

Data Acquisition at T/B-Lymphocyte Ratio of 7:3

From each of the aforementioned 1057 dots counted as T-lymphocytes, the fluorescence intensity and the side scattered light information of each dot was extracted as T-lymphocyte information. Also, from each of the 454 dots randomly selected from the 749 dots counted as B-lymphocytes, the fluorescence intensity and the side scattered light information of each dot was extracted as B-lymphocyte information. Then, based on the information regarding the total 1511 dots, i.e., 1057 T-lymphocytes and 454 B-lymphocytes, data at a T/B-lymphocyte ratio of 7:3 was acquired.

Data Acquisition at T/B-Lymphocyte Ratio of 6:4

From each of the aforementioned 1057 dots counted as T-lymphocytes, the fluorescence intensity and the side scattered light information of each dot was extracted as T-lymphocyte information. Also, from each of the 703 dots randomly selected from the 749 dots counted as B-lymphocytes, the fluorescence intensity and the side scattered light information of each dot was extracted as B-lymphocyte information. Then, based on the information regarding the total 1760 dots, i.e., 1057 T-lymphocytes and 703 B-lymphocytes, data at a T/B-lymphocyte ratio of 6:4 was acquired.

Data Acquisition at T/B-Lymphocyte Ratio of 5:5

From each of the 750 dots randomly selected from the aforementioned 1057 dots counted as T-lymphocytes, the fluorescence intensity and the side scattered light information of each dot was extracted as T-lymphocyte information. Also, from each of the 749 dots counted as B-lymphocytes, the fluorescence intensity and the side scattered light information of each dot was extracted as B-lymphocyte information. Then, based on the information regarding the total 1499 dots, i.e., 750 T-lymphocytes and 749 B-lymphocytes, data at a T/B-lymphocyte ratio of 5:5 was acquired.

Data Acquisition at T/B-Lymphocyte Ratio of 4:6

From each of the 500 dots randomly selected from the aforementioned 1057 dots counted as T-lymphocytes, the fluorescence intensity and the side scattered light information of each dot was extracted as T-lymphocyte information. Also, from each of the 749 dots counted as B-lymphocytes, the fluorescence intensity and the side scattered light information of each dot was extracted as B-lymphocyte information. Then, based on the information regarding the total 1249 dots, i.e., 500 T-lymphocytes and 749 B-lymphocytes, data at a T/B-lymphocyte ratio of 4:6 was acquired.

Data Acquisition at T/B-Lymphocyte Ratio of 2:8

From each of the 188 dots randomly selected from the aforementioned 1057 dots counted as T-lymphocytes, the fluorescence intensity and the side scattered light information of each dot was extracted as T-lymphocyte information. Also, from each of the 749 dots counted as B-lymphocytes, the fluorescence intensity and the side scattered light information of each dot was extracted as B-lymphocyte information. Then, based on the information regarding the total 937 dots, i.e., 188 T-lymphocytes and 749 B-lymphocytes, data at a T/B-lymphocyte ratio of 2:8 was acquired.

FIGS. 23A to 23I are scattergrams representing fluorescence intensity and side scattered light information showing the particle size distribution of lymphocytes at the respective T/B-lymphocyte ratios. FIGS. 24A to 24I are fluorescence intensity-based particle size distribution charts (histograms) showing the particle size distribution of lymphocytes at the respective T/B-lymphocyte ratios. The mean value, the median value, the skewness, the kurtosis, the dispersion, the standard deviation, the standard error, the root-mean-square (RMS), and the mean-median value at the respective T/B-lymphocyte ratios are presented in Table 1. FIGS. 25A to 25I are graphs showing the change of the mean value, the median value, the skewness, the kurtosis, the dispersion, the standard deviation, the standard error, the root-mean-square (RMS), and the mean-median value of the fluorescence intensity of lymphocytes according to the respective T/B-lymphocyte ratios.

TABLE 1

| T/B lymphocyte ratio | 10:0 | 9:1 | 8:2 | 7:3 | 6:4 | 5:5 | 4:6 | 2:8 | 0:10 |
|---|---|---|---|---|---|---|---|---|---|
| Number of T lymphocyte dots | 1057 | 1057 | 1057 | 1057 | 1057 | 750 | 500 | 188 | 0 |
| Number of B lymphocyte dots | 0 | 118 | 265 | 454 | 703 | 749 | 749 | 749 | 749 |
| Total number of dots | 1057 | 1175 | 1322 | 1511 | 1760 | 1499 | 1249 | 937 | 749 |
| B cell ratio | 0% | 10% | 20% | 30% | 40% | 50% | 60% | 80% | 100% |
| Mean | 93.1712 | 91.605 | 89.998 | 88.371 | 86.898 | 84.873 | 82.884 | 80.064 | 77.652 |
| Median value | 93 | 92 | 90 | 88 | 86 | 83 | 80 | 77 | 74 |
| Kurtosis | 0.11031 | 0.0072 | 0.0616 | 0.1649 | 0.2974 | 0.4178 | 0.6075 | 0.9235 | 1.2573 |
| Skewness | −0.024 | −0.096 | −0.26 | −0.32 | −0.178 | −0.005 | 0.3631 | 1.109 | 2.287 |
| Variance | 186.21 | 216.31 | 239.74 | 255.64 | 266.27 | 260.79 | 256.24 | 253.52 | 240.54 |
| Standard deviation | 13.6459 | 14.707 | 15.483 | 15.989 | 16.318 | 16.149 | 16.008 | 15.922 | 15.509 |
| Standard error | 0.41972 | 0.4291 | 0.4258 | 0.4113 | 0.389 | 0.4171 | 0.4529 | 0.5202 | 0.5667 |
| RMS | 94.1643 | 92.777 | 91.319 | 89.804 | 88.416 | 86.395 | 84.414 | 81.63 | 79.183 |
| Mean-median value | 0.17124 | −0.395 | −0.002 | 0.3706 | 0.8977 | 1.8732 | 2.8839 | 3.064 | 3.6515 |

From FIGS. 24A to 24I, it can be understood that the higher the T-lymphocyte ratio, the further the peak of the fluorescence intensity-based particle size distribution shifts toward the right-hand side (direction toward higher fluorescence intensity). In contrast, it can be understood that the higher the B-lymphocyte ratio, the further the peak of the fluorescence intensity-based particle size distribution shifts toward the left-hand side (direction toward lower fluorescence intensity). Moreover, Table 1 and FIGS. 25A to 25I suggest that use of the mean value, the median value, the skewness, the kurtosis, the dispersion, the standard deviation, the standard error, the root-mean-square (RMS), and/or the mean-median value of the fluorescence intensity of lymphocytes enables the T/B-lymphocyte ratio of a sample to be measured.

Figure 25I:
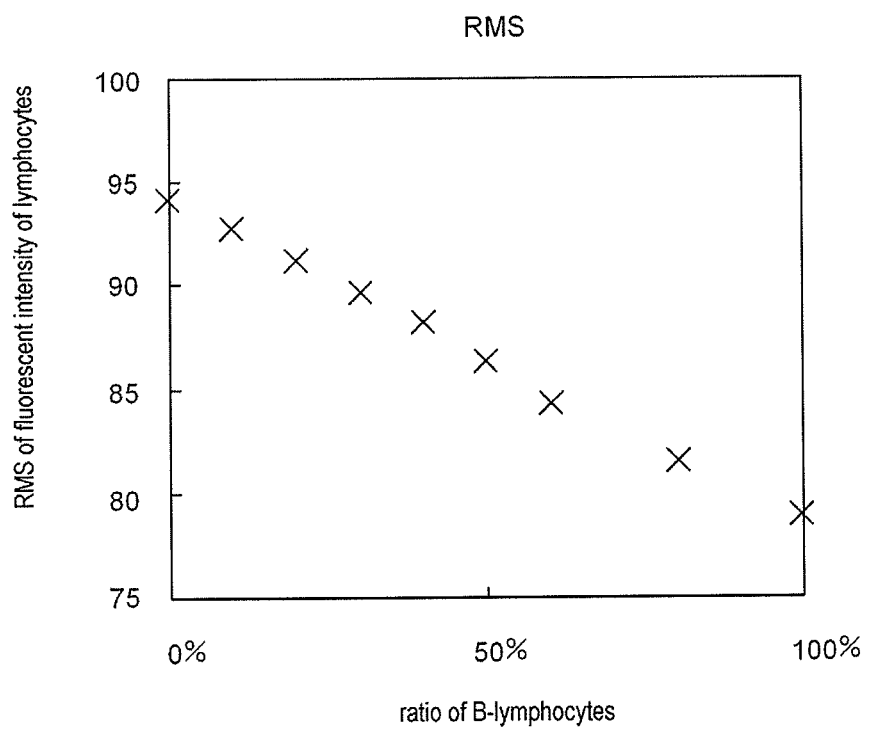
FIG. 25I is a graph showing the root-mean-square of the fluorescence intensity of lymphocytes at the respective T/B-lymphocyte ratios.

From FIGS. 25A, 25B, and 25I, it can be understood that the mean value, the median value, and the root-mean-square (RMS) of fluorescence intensity are decreased as the B-lymphocyte ratio of a sample is increased. From FIGS. 25C and 25D, it can be understood that the mean-median value and the skewness of fluorescence intensity are increased as the B-lymphocyte ratio of a sample is increased. Therefore, this suggests that the B-lymphocyte ratio of a blood specimen treated with a fluorescent dye that stains nucleic acid can be obtained from the mean value, the median value, and the root-mean-square (RMS) or the mean-median value of the fluorescence intensity of lymphocytes in the blood specimen. Also, this suggests that in the case where the obtained lymphocyte ratio is not in a normal range (5 to 20%), it is possible to determine that the B-lymphocyte ratio of the blood specimen is abnormal.

From FIG. 25E, it can be understood that when the B-lymphocyte ratio of a sample is about 30 to 100%, the value of the kurtosis of fluorescent intensity is increased as the B-lymphocyte ratio of the sample is increased. Therefore, this suggests that the B-lymphocyte ratio of a blood specimen treated with a fluorescent dye that stains nucleic acid can be obtained from the kurtosis of the fluorescence intensity of lymphocytes in the blood specimen when the B-lymphocyte ratio is in the range of about 30 to 100%. From FIG. 25H, it can be understood that when the B-lymphocyte ratio of a sample is about 40 to 100%, the value of the standard error of fluorescent intensity is increased as the B-lymphocyte ratio of the sample is increased. Therefore, this suggests that the B-lymphocyte ratio of a blood specimen treated with a fluorescent dye that stains nucleic acid can be obtained from the standard error of the fluorescence intensity of lymphocytes in the blood specimen when the B-lymphocyte ratio is in the range of about 40 to 100%.

From FIGS. 25F and 25G, it can be understood that when the B-lymphocyte ratio of a sample is in the range of 0 to about 40%, the values of the dispersion and the standard deviation of fluorescent intensity are increased as the B-lymphocyte ratio of the sample is increased. Therefore, this suggests that the B-lymphocyte ratio of a blood specimen treated with a fluorescent dye that stains nucleic acid can be obtained from the dispersion and the standard deviation of the fluorescence intensity of lymphocytes in the blood specimen when the B-lymphocyte ratio is in the range of 0 to about 40%. Also, this suggests that in the case where the obtained lymphocyte ratio is not in a normal range (5 to 20%), it is possible to determine that the B-lymphocyte ratio of the blood specimen is abnormal. Also, this suggests that combining the dispersion or standard deviation of the fluorescence intensity of lymphocytes and the skewness, kurtosis, or standard error of the fluorescence intensity of lymphocytes enables the B-lymphocyte ratio of a blood specimen over the 0 to 100% range to be obtained.

Example 3

<Analysis of Healthy Subject's Blood>
(Investigation of T/B-Lymphocyte Ratio)
Three 50 μL monocyte layer samples were provided. 1 μL of an FITC-labeled anti-CD19 antibody (manufactured by Dako) was added to the first sample, 1 μL of an FITC-labeled anti-CD3 antibody (manufactured by Dako) was added to the second sample, and 1 μL of an FITC-labeled mouse IgG (manufactured by Dako) was added as a control to the third sample.

The prepared samples were analyzed using a flow cytometer (FACS Calibur (manufactured by BD)) with the number of cell takeup being set to 2000 to measure B-lymphocytes and T-lymphocytes. Results showed that the monocyte layer samples had CD3 positive cells, i.e., T-lymphocytes, in a proportion of 20.7% and CD19 positive cells, i.e., B-lymphocytes, in a proportion of 2.59%. From this result, it was found that the T/B-lymphocyte ratio of healthy subject's blood in Example 2 was 8:1 (that is, the B-lymphocyte ratio was about 11%).

(Investigation of Lymphocyte Count)
Healthy person's blood collected in Example 2 was subjected to measurement using an XE-2100 to classify leucocytes into 4 types. Stromatolyser 4DL and Stromatolyser 4DS (both manufactured by Sysmex Corporation) were used as measuring reagents. Measurement results showed that the number of lymphocytes contained in healthy subject's blood was 1550/μL.

(Calculation of Mean-Median Value)
Fluorescence intensity and side scattered light information obtained from the measurement was analyzed using a KaleidaGraph (manufactured by Hulinks Inc.). First, from fluorescence intensity and side scattered light information obtained from the measurement, a scattergram of a whole blood sample was prepared. Next, using the scattergram of the whole blood sample, dots appeared in the lymphocyte region were counted as lymphocytes, and the number of the dots was 1004. Regarding these 1004 dots, from their fluorescence intensity information, the mean-median value of the fluorescence intensity-based particle size distribution of the lymphocytes in the whole bood sample was calculated. The mean-median value of the fluorescence intensity-based particle size distribution was 0.502488. Meanwhile, the B-lymphocyte ratio in healthy subject's blood was 11%. Therefore, the measured mean-median value of the fluorescence intensity-based particle size distribution when the B-lymphocyte ratio is 11% will be 0.502488.

<Analysis of Model Blood>
(Preparation of Model Blood)
Healthy subject's blood collected in Example 2 was diluted 10-fold with phosphate buffered saline (PBS) to prepare a 10-fold diluted whole blood sample. 400 μL of a B-lymphocyte sample as prepared in Example 2 was centrifuged at 1000 rpm for 3 minutes. After centrifugation, supernatant was removed, and B-lymphocyte pellets were obtained. The obtained B-lymphocyte pellets were dispersed in 200 μL of the 10-fold diluted whole blood sample to prepare model blood.

(Investigation of Lymphocyte Count)
The lymphocyte count of the prepared model blood was measured in the same manner as the lymphocyte count investigation in the analysis of healthy subject's blood described above. Measurement results showed that the number of lymphocytes contained in the model blood was 5230/μL.

(Calculation of Mean-Median Value)
The mean-median value of the fluorescence intensity-based particle size distribution of the prepared model blood was calculated in the same manner as the mean-median value calculation in the analysis of healthy subject's blood described above. The mean-median value of the fluorescence intensity-based particle size distribution was 3.166529. Note that 4038 dots appeared in the lymphocyte region.

Meanwhile, the number of lymphocytes contained in healthy subject's blood was 1550/μL. Therefore, the number of lymphocytes in the 10-fold diluted whole blood sample will be 155/μL. In addition, the number of lymphocytes in the model blood was 5230/μL. The number of lymphocytes derived from the 10-fold diluted whole blood sample was 155/μL. Therefore, the number of B-lymphocytes in the model blood derived from the B-lymphocyte sample will be 5075/μL. Moreover, the proportion of B-lymphocytes in healthy subject's blood was 11%. Theoretically, the proportion of B-lymphocytes in the 10-fold diluted whole blood sample is the same. Therefore, the proportion of B-lymphocytes in the 10-fold diluted whole blood sample will be 11% of 155/μL, or 17/μL. In the model blood, the number of B-lymphocytes derived from the B-lymphocyte sample will be 5075/μL, and the number of B-lymphocytes derived from the 10-fold diluted whole blood sample will be 17/μL. Therefore, the total number of B-lymphocytes in the model blood will be 5092/μL. Since the number of lymphocytes in the model blood was 5230/μL, the proportion of B-lymphocytes will be 97%. The measured mean-median value of the particle size distribution of fluorescence intensity when the B-lymphocyte proportion is 97% will be 3.166529.

<Investigation of Correlation Between Graph Showing Change of Mean-Median Value and Measured Value>

Figure 26:
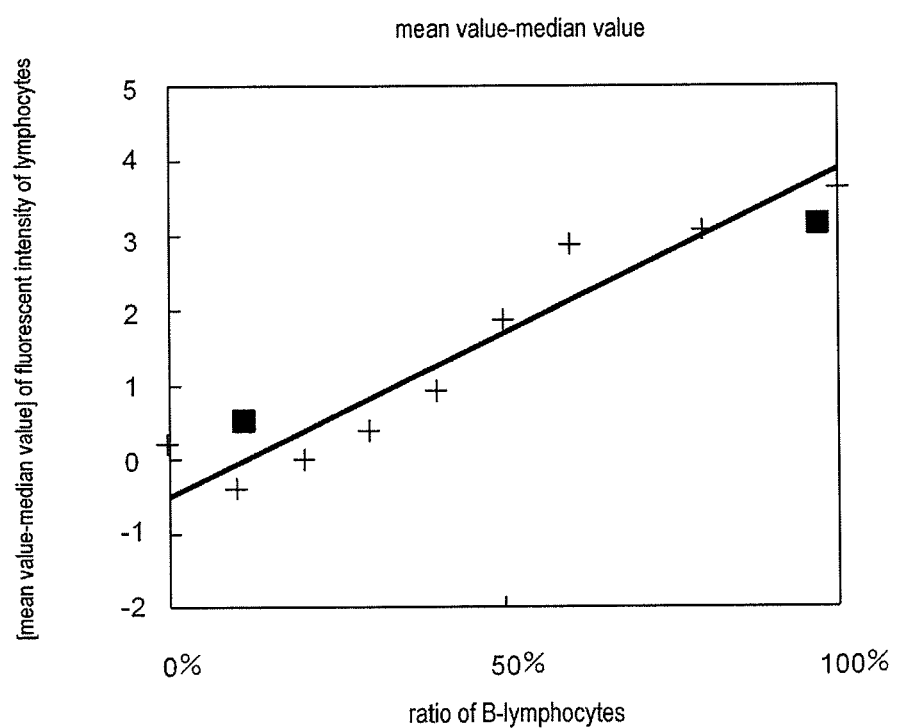
FIG. 26 is a graph illustrating the correlation between a graph showing the relationship between the mean-median value of fluorescence intensity and the B-lymphocyte ratio and the measured values representing the particle size distribution of fluorescence intensity.

FIG. 26 shows a graph in which measured values representing the particle size distribution of the fluorescence intensity of healthy subject's blood and the model blood are plotted over the graph obtained in Example 2 showing the relationship between the mean-median value of fluorescence intensity and the B-lymphocyte ratio presented in FIG. 25C. In FIG. 26, "■" shows a plot of a measured value. It can be understood from FIG. 26 that there is a correlation between the graph showing the relationship between the mean-median value of fluorescence intensity and the B-lymphocyte ratio and the measured values representing the particle size distribution of fluorescence intensity.

INDUSTRIAL APPLICABILITY

The blood analyzer and the blood analyzing method of the present invention are useful respectively as a blood analyzer and a blood analyzing method that optically measure a blood specimen and classify cell groups contained in the blood specimen into a plurality of types.

DESCRIPTION OF REFERENCE NUMERALS

| | |
|---|---|
| 1 | Blood analyzer |
| 2 | Measurement unit |
| 22 | Sample preparation portion |
| 221, 222, 223 | Reagent container |
| 23 | Detecting portion |
| 231 | Flow cell |
| 237 | Semiconductor laser |
| 243 | Photodiode |
| 246 | Photodiode |
| 248 | Avalanche photodiode |
| 5 | Information processing unit |
| 5a | Computer |
| 51 | Main body |
| 51a | CPU |
| 51b | ROM |
| 51c | RAM |
| 51d | Hard disk |
| 51h | Image output interface |
| 52 | Image display portion |
| 54a | Computer program |
| MC | Mixing chamber |
| H | Heater |
| D | Optical detector |
| R1, R2, R3 | Analysis result screen |
| SL1, SL2 | Scattergram representing side scattered light intensity and fluorescence intensity |
| SN1, SN2 | Histogram representing fluorescence intensity of lymphocytes and cell count |

The invention claimed is:

1. A blood analyzer comprising:
a blood specimen supplying portion for supplying a blood specimen;
a sample preparation portion for preparing a measurement sample without using a fluorescence-labeled antibody by mixing the blood specimen supplied from the blood specimen supplying portion, a hemolyzing agent that contains a cationic surfactant and a nonionic surfactant, and a fluorescent dye that stains nucleic acid;
a light source for irradiating light onto the measurement sample prepared by the sample preparation portion;
a first detector for detecting fluorescence emitted from each of cells contained in the measurement sample irradiated with light by the light source to output fluorescence intensity of each of the cells;
a second detector for detecting scattered light emitted from each of the cells contained in the measurement sample irradiated with light by the light source to output scattered light intensity of each of the cells;
an information processing portion configured to:
  a) distinguish lymphocytes from leucocytes contained in the cells based on fluorescence intensities outputted from the first detector and scattered light intensities outputted from the second detector;
  b) obtain an indicator selected from the group consisting of a measure of central tendency of fluorescence intensities of the distinguished lymphocytes, a dispersion of fluorescence intensities of the distinguished lymphocytes, a kurtosis of a particle distribution of fluorescence intensities of the distinguished lymphocytes and a skewness of the particle distribution of fluorescence intensities of the distinguished lymphocytes; and
  c) obtain a ratio between a B-lymphocyte count and a T-lymphocyte count based on the obtained indicator in b) and a predetermined relationship value between B-lymphocyte and T-lymphocyte, wherein the relationship value directs one-to-one relationship between the indicator and the ratio; and
an output portion for outputting the ratio obtained by the information processing portion.

2. The blood analyzer according to claim 1, wherein the ratio includes at least one of a ratio of a B-lymphocyte count to a total B-lymphocyte and T-lymphocyte count and; a ratio of a T-lymphocyte count to a total B-lymphocyte and T-lymphocyte count.

3. The blood analyzer according to claim 1, wherein
the information processing portion is configured to compare the indicator with a predetermined threshold value to determine whether the ratio is abnormal or not, and
the output portion is configured to, in the case where the ratio is determined to be abnormal by the information processing portion, output that the ratio is abnormal.

4. The blood analyzer according to claim 1, wherein
the information processing portion is configured to:
  obtain a ratio of a B-lymphocyte count to a total B-lymphocyte and T-lymphocyte count based on the indicator and the predetermined relationship value; and
  compare the obtained ratio of a B-lymphocyte count to a total B-lymphocyte and T-lymphocyte count with a predetermined threshold value to determine whether the ratio between the B-lymphocyte count and the T-lymphocyte count is abnormal or not, and
the output portion is configured to, in the case where the ratio between the B-lymphocyte count and the T-lymphocyte count is determined to be abnormal by the information processing portion, output that the ratio between the B-lymphocyte count and the T-lymphocyte count is abnormal.

5. The blood analyzer according to claim 1, wherein
the information processing portion is configured to:
  obtain a ratio of a T-lymphocyte count to a total B-lymphocyte and T-lymphocyte count based on the indicator and the predetermined relationship value; and
  compare the obtained ratio of a T-lymphocyte count to a total B-lymphocyte and T-lymphocyte count with a predetermined threshold value to determine whether the ratio between the B-lymphocyte count and the T-lymphocyte count is abnormal or not, and
the output portion is configured to, in the case where the ratio between the B-lymphocyte count and T-lymphocyte count is determined to be abnormal by the information processing portion, output that the ratio between the B-lymphocyte count and the T-lymphocyte count is abnormal.

6. The blood analyzer according to claim 1, wherein
the information processing portion is configured to distinguish lymphocytes from leucocytes contained in the cells by classifying the leucocytes, and
the output portion is configured to output a result of leucocyte classification performed by the information processing portion.

7. The blood analyzer according to claim 6, wherein
the information processing portion is configured to classify the leucocytes contained in the cells into at least four groups including one group of lymphocytes.

8. A blood analyzing method comprising the steps of:
  preparing a measurement sample without using a fluorescence-labeled antibody by mixing a blood specimen, a hemolyzing agent containing a cationic surfactant and a nonionic surfactant, and a fluorescent dye that stains nucleic acid;
  irradiating light onto the prepared measurement sample;
  detecting fluorescence and scattered light emitted from each of cells contained in the measurement sample irradiated with light to output fluorescence intensity and scattered light intensity of each of the cells;
  distinguishing lymphocytes from leucocytes contained in the cells based on outputted fluorescence intensities and outputted scattered light intensities;
  obtaining an indicator selected from the group consisting of a measure of central tendency of fluorescence intensities of the distinguished lymphocytes, a dispersion of fluorescence intensities of the distinguished lymphocytes, a kurtosis of the particle distribution of fluorescence intensities of the distinguished lymphocytes and a skewness of the particle distribution of fluorescence intensities of the distinguished lymphocytes;
  obtaining a ratio between a B-lymphocyte count and a T-lymphocyte count based on the obtained indicator and a predetermined relationship value between B-lymphocyte and T-lymphocyte, wherein the relationship information directs one-to-one relationship between the indicator and the ratio; and
  outputting the obtained ratio.

9. The blood analyzing method according to claim 8, wherein the ratio between the B-lymphocyte count and the T-lymphocyte count includes at least one of a ratio of a B-lymphocyte count to a total B-lymphocyte and T-lymphocyte count and a ratio of a T-lymphocyte count to a total B-lymphocyte and T-lymphocyte count.

10. A blood analyzer comprising:
  a blood specimen supplying portion for supplying a blood specimen;
  a sample preparation portion for preparing a measurement sample without using a fluorescence-labeled antibody by mixing the blood specimen supplied from the blood specimen supplying portion, a hemolyzing agent that contains a cationic surfactant and a nonionic surfactant, and a fluorescent dye that stains nucleic acid;
  a light source for irradiating light onto the measurement sample prepared by the sample preparation portion;
  a first detector for detecting fluorescence emitted from each of cells contained in the measurement sample irradiated with light by the light source to output fluorescence intensity of each of the cells;
  a second detector for detecting scattered light emitted from each of cells contained in the measurement sample irradiated with light by the light source to output scattered light intensity of each of the cells;
  an information processing portion configured to:
    a) distinguish lymphocytes from leucocytes contained in the cells based on fluorescence intensities outputted from the first detector and scattered light intensities outputted from the second detector;
    b) obtain an indicator selected from the group consisting of a measure of central tendency of fluorescence intensities of the distinguished lymphocytes, a dispersion of fluorescence intensities of the distinguished lymphocytes, a kurtosis of a particle distribution of fluorescence intensities of the distinguished lymphocytes and a skewness of the particle distribution of fluorescence intensities of the distinguished lymphocytes;
    c) obtain a ratio between a B-lymphocyte count and a T-lymphocyte count based on the obtained indicator and a predetermined relationship value between B-lymphocyte and T-lymphocyte, wherein the relationship value directs one-to-one relationship between the indicator and the ratio; and
    d) compare the indicator with a predetermined threshold value to determine whether the ratio is abnormal or not; and
  an output portion for outputting that the ratio is abnormal, in the case where the ratio is determined to be abnormal by the information processing portion.

11. The blood analyzer according to claim 10, wherein the ratio includes at least one of a ratio of a B-lymphocyte count to a total B-lymphocyte and T-lymphocyte count, and a ratio of a T-lymphocyte count to a total B-lymphocyte and T-lymphocyte count.

12. The blood analyzer according to claim 10, wherein the information processing portion is configured to distinguish lymphocytes from leucocytes contained in the cells by classifying the leucocytes, and the output portion is configured to output a result of leucocyte classification performed by the information processing portion.

13. The blood analyzer according to claim 10, wherein the information processing portion is configured to classify the leucocytes contained in the cells into at least four groups including one group of lymphocytes.

* * * * *